US007785854B2

(12) United States Patent
St-Pierre et al.

(10) Patent No.: US 7,785,854 B2
(45) Date of Patent: Aug. 31, 2010

(54) MODIFIED CELLULASES WITH INCREASED THERMOSTABILITY, THERMOPHILICITY, AND ALKALOPHILICITY

(75) Inventors: Patrick St-Pierre, Gatineau (CA); Nabil Masri, Gatineau (CA); Marie-Christine Fournier, Ottawa (CA); Theresa C. White, Ottawa (CA)

(73) Assignee: Iogen Energy Corporation, Ontario (CA)

( * ) Notice: Subject to any disclaimer, the term of this patent is extended or adjusted under 35 U.S.C. 154(b) by 0 days.

(21) Appl. No.: 11/846,663

(22) Filed: Aug. 29, 2007

(65) Prior Publication Data

US 2008/0076152 A1 Mar. 27, 2008

Related U.S. Application Data

(60) Provisional application No. 60/841,507, filed on Aug. 31, 2006, provisional application No. 60/846,970, filed on Sep. 25, 2006.

(51) Int. Cl.
*C12N 9/00* (2006.01)
*C12N 9/24* (2006.01)
*C12N 1/20* (2006.01)
*C12N 15/00* (2006.01)
*C07H 21/04* (2006.01)

(52) U.S. Cl. ............... 435/200; 435/183; 435/252.3; 435/320.1; 536/23.2

(58) Field of Classification Search ............ None
See application file for complete search history.

(56) References Cited

U.S. PATENT DOCUMENTS

| 5,677,151 | A | 10/1997 | Wilson et al. |
| 6,114,158 | A | 9/2000 | Li et al. |
| 7,348,168 | B2 | 3/2008 | Wu et al. |
| 2006/0105914 | A1 | 5/2006 | Taylor et al. |
| 2006/0205042 | A1 | 9/2006 | Aehle et al. |

FOREIGN PATENT DOCUMENTS

WO 98/14597 4/1998

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Al et al., "Mutation and expression of N233C-D506C of cellulase Cel6B from *Thermobifida fusca* in *Escherichia coli*", Enzyme and Microbial Technology, vol. 30 (2002) 804-8.
Chica et al., "Semi-rational approaches to engineering enzyme activity: combining the benefits of directed evolution and rational design", Current Opinion in Biotechnology, vol. 16 (2005) 378-84.
Davies et al., "Structure and function of *Humicola insolens* family 6 cellulases: structure of the endoglucanase, Cel6B, at 1.6 A Resolution", Biochem J., vol. 348 (2000) 201-7.

Eijsink et al., "Directed evolution of enzyme stability", Biomolecular Engineering, vol. 22 (2005) 21-30.
Eijsink et al., "Rational engineering of enzyme stability", Journal of Biotechnology, vol. 113 (2004) 105-20.
Foreman et al. "Transcriptional Regulation of Biomass-degrading Enzymes in the Filamentous Fungus *Trichoderma reesei*", J. Biol. Chem., vol. 278, No. 34 (2003) 31988-997.
Gray et al., "Bioethanol", Current Opinion in Chemical Biology, vol. 10 (2006) 141-46.
Henrissat et al. "A scheme for designating enzymes that hydrolyse the polysaccharides in the cell walls of plants", FEBS Letters, vol. 425 (1998) 352-54.
Hughes et al., "High-throughput screening of cellulase F mutants from multiplexed plasmid sets using an automated plate assay on a functional proteomic robotic workcell", Proteome Science, vol. 4, No. 10 (2006) 10-23.
Lehtio et al., "The binding specificity and affinity determinants of family 1 and family 3 cellulose binding modules", Proc. Natl. Acad. Sci., vol. 100, No. 2 (2003) 484-89.
Rouvinen et al., "Three-Dimensional Structure of Cellobiohydrolase II from *Trichoderma reesei*", Science, vol. 249 (1990) 380-86.
Spezio et al., "Crystal Structure of the Catalytic Domain of a Thermophilic Endocellulase", Biochemistry, vol. 32 (1993) 9906-16.
Srisodsuk et al. "Role of the Interdomain Linker Peptide of *Trichoderma reesei* Cellobiohydrolase I in Its Interaction with Crystalline Cellulose", J. Biol. Chem, vol. 268, No. 28 (1993) 20756-61.
Tomme et al. "Studies of the cellulolytic system of *Trichoderma reesei* QM 9414; Analysis of domain function in two cellobiohydrolases by limited proteolysis", Eur. J. Biochem, vol. 170 (1988) 575-81.
Varrot et al. "Crystal structure of the catalytic core domain of the family 6 cellobiohydrolase II, Cel6A, from *Humicola insolens*, at 1.92 A Resolution", Biochem. J., vol. 337 (1999) 297-304.
Varrot et al. "*Mycobacterium tuberculosis* Strains Possess Functional Cellulases", J. Biol. Chem., vol. 280, No. 21 (2005) 20181-84.
von Ossowski et al., "Engineering the Exo-loop of *Trichoderma reesei* Cellobiohydrolase, Cel7A. A Comparison with *Phanerochaete chrysosporium* Cel7D", J. Mol. Biol., No. 333 (2003) 817-29.
Wohlfahrt et al., "Probing pH-Dependent Functional Elements in Proteins: Modification of Carboxylic Acid Pairs in *Trichoderma reesei* Cellobiohydrolase Cel6A", Biochemistry, vol. 42 (2003) 10095-103.

(Continued)

*Primary Examiner*—Christian L Fronda
(74) *Attorney, Agent, or Firm*—Fitzpatrick, Cella, Harper & Scinto

(57) ABSTRACT

A modified Family 6 cellulase enzyme comprising a proline residue at position 413 is provided. Genetic constructs and genetically modified microbes comprising DNA sequences encoding the modified Family 6 cellulase are also provided. Family 6 cellulases of the invention display improved thermostability, thermophilicity, alkalophilicity, or a combination thereof, relative to the parent Family 6 cellulases. Such cellulases find use in a variety of applications in industry that require cellulase stability and activities at temperatures, pH values, or both, above that of the native enzyme.

17 Claims, 15 Drawing Sheets

OTHER PUBLICATIONS

Zhang et al. "Site-directed mutation of noncatalytic residues of *Thermobifida fusca* exocellulase Cel6B", Eur. J. Biochem, vol. 267 (2000) 3101-115.

Moriya, et al. "Cloning and Overexpression of the avi2 Gene Encoding a Major Cellulase Produced by *Humicola insolens* FERM BP-5977", Biosci. Biotechnol. Biochem., vol. 67, No. 6 (2003) 1434-37.

Arnold, "Combinatorial and computational challenges for biocatalyst design", Nature, vol. 409 (2001) 253-57.

Cantarel, et al., "The Carbohydrate-Active EnZymes database (CAZy): an expert resource for Glycogenomics" Nucleic Acids Research, vol. 37 (2009) D233-38.

Sigrist, et al., "PROSITE: A documented database using patterns and profiles as motif descriptors", Brief Bioinform., vol. 3, No. 3 (2002) 265-74.

* cited by examiner

SEQUENCE LISTING

<160> NUMBER OF SEQ ID NOS: 50

<210> SEQ ID NO 1
<211> LENGTH: 447
<212> TYPE: PRT
<213> ORGANISM: Trichoderma reesei

<400> SEQUENCE: 1

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

```
Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
        260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 2
<211> LENGTH: 832
<212> TYPE: PRT
<213> ORGANISM: Cellulomonas fimi

<400> SEQUENCE: 2

Ala Pro Val His Val Asp Asn Pro Tyr Ala Gly Ala Val Gln Tyr Val
1               5                   10                  15

Asn Pro Thr Trp Ala Ala Ser Val Asn Ala Ala Ala Gly Arg Gln Ser
            20                  25                  30

Ala Asp Pro Ala Leu Ala Ala Lys Met Arg Thr Val Ala Gly Gln Pro
        35                  40                  45

Thr Ala Val Trp Met Asp Arg Ile Ser Ala Ile Thr Gly Asn Ala Asp
    50                  55                  60

Gly Asn Gly Leu Lys Phe His Leu Asp Asn Ala Val Ala Gln Lys
65                  70                  75                  80

Ala Ala Gly Val Pro Leu Val Phe Asn Leu Val Ile Tyr Asp Leu Pro
                85                  90                  95

Gly Arg Asp Cys Phe Ala Leu Ala Ser Asn Gly Glu Leu Pro Ala Thr
            100                 105                 110

Asp Ala Gly Leu Ala Arg Tyr Lys Ser Glu Tyr Ile Asp Pro Ile Ala
        115                 120                 125

Asp Leu Leu Asp Asn Pro Glu Tyr Glu Ser Ile Arg Ile Ala Ala Thr
    130                 135                 140

Ile Glu Pro Asp Ser Leu Pro Asn Leu Thr Thr Asn Ile Ser Glu Pro
145                 150                 155                 160

Ala Cys Gln Gln Ala Ala Pro Tyr Tyr Arg Gln Gly Val Lys Tyr Ala
                165                 170                 175
```

```
Leu Asp Lys Leu His Ala Ile Pro Asn Val Tyr Asn Tyr Ile Asp Ile
            180                 185                 190

Gly His Ser Gly Trp Leu Gly Trp Asp Ser Asn Ala Gly Pro Ser Ala
        195                 200                 205

Thr Leu Phe Ala Glu Val Ala Lys Ser Thr Thr Ala Gly Phe Ala Ser
        210                 215                 220

Ile Asp Gly Phe Val Ser Asp Val Ala Asn Thr Thr Pro Leu Glu Glu
225                 230                 235                 240

Pro Leu Leu Ser Asp Ser Ser Leu Thr Ile Asn Asn Thr Pro Ile Arg
                245                 250                 255

Ser Ser Lys Phe Tyr Glu Trp Asn Phe Asp Phe Asp Glu Ile Asp Tyr
                260                 265                 270

Thr Ala His Met His Arg Leu Leu Val Ala Ala Gly Phe Pro Ser Ser
            275                 280                 285

Ile Gly Met Leu Val Asp Thr Ser Arg Asn Gly Trp Gly Gly Pro Asn
        290                 295                 300

Arg Pro Thr Ser Ile Thr Ala Ser Thr Asp Val Asn Ala Tyr Val Asp
305                 310                 315                 320

Ala Asn Arg Val Asp Arg Arg Val His Arg Gly Ala Trp Cys Asn Pro
                325                 330                 335

Leu Gly Ala Gly Ile Gly Arg Phe Pro Glu Ala Thr Pro Ser Gly Tyr
            340                 345                 350

Ala Ala Ser His Leu Asp Ala Phe Val Trp Ile Lys Pro Pro Gly Glu
        355                 360                 365

Ser Asp Gly Ala Ser Thr Asp Ile Pro Asn Asp Gln Gly Lys Arg Phe
    370                 375                 380

Asp Arg Met Cys Asp Pro Thr Phe Val Ser Pro Lys Leu Asn Asn Gln
385                 390                 395                 400

Leu Thr Gly Ala Thr Pro Asn Ala Pro Leu Ala Gly Gln Trp Phe Glu
                405                 410                 415

Glu Gln Phe Val Thr Leu Val Lys Asn Ala Tyr Pro Val Ile Gly Gly
                420                 425                 430

Thr Thr Pro Val Glu Asp Leu Val Ala Pro Thr Val Pro Thr Gly Leu
            435                 440                 445

Thr Ala Gly Thr Thr Ala Thr Ser Val Pro Leu Ser Trp Thr Ala
        450                 455                 460

Ser Thr Asp Asn Val Ala Val Thr Gly Tyr Asp Val Tyr Arg Gly Thr
465                 470                 475                 480

Thr Leu Val Gly Thr Thr Ala Ala Thr Ser Tyr Thr Val Thr Gly Leu
                485                 490                 495

Thr Pro Ala Thr Ala Tyr Ser Phe Thr Val Arg Ala Lys Asp Ala Ala
            500                 505                 510

Gly Asn Val Ser Ala Ala Ser Ala Ala Ala Ala Thr Thr Gln Ser
            515                 520                 525

Gly Thr Val Thr Asp Thr Thr Ala Pro Ser Val Pro Ala Gly Leu Thr
    530                 535                 540

Ala Gly Thr Thr Thr Thr Thr Val Pro Leu Ser Trp Thr Ala Ser
545                 550                 555                 560

Thr Asp Asn Ala Gly Gly Ser Gly Val Ala Gly Tyr Glu Val Leu Arg
                565                 570                 575

Gly Thr Val Val Gly Thr Thr Thr Ala Thr Ser Tyr Thr Val Thr
            580                 585                 590
```

```
Gly Leu Thr Ala Gly Thr Thr Tyr Ser Phe Ser Val Arg Ala Lys Asp
            595                 600                 605

Val Ala Gly Asn Thr Ser Ala Ala Ser Ala Ala Val Ser Ala Thr Thr
        610                 615                 620

Gln Thr Gly Thr Val Val Asp Thr Thr Ala Pro Ser Val Pro Thr Gly
625                 630                 635                 640

Leu Thr Ala Gly Thr Thr Thr Ser Ser Val Pro Leu Thr Trp Thr
                645                 650                 655

Ala Ser Thr Asp Asn Ala Gly Gly Ser Gly Val Ala Gly Tyr Glu Val
                660                 665                 670

Phe Asn Gly Thr Thr Arg Val Ala Thr Val Thr Ser Thr Ser Tyr Thr
            675                 680                 685

Val Thr Gly Leu Ala Ala Asp Thr Ala Tyr Ser Phe Thr Val Lys Ala
        690                 695                 700

Lys Asp Val Ala Gly Asn Val Ser Ala Ser Ala Ala Val Ser Ala
705                 710                 715                 720

Arg Thr Gln Ala Ala Thr Ser Gly Gly Cys Thr Val Lys Tyr Ser Ala
                725                 730                 735

Ser Ser Trp Asn Thr Gly Phe Thr Gly Thr Val Glu Val Lys Asn Asn
            740                 745                 750

Gly Thr Ala Ala Leu Asn Gly Trp Thr Leu Gly Phe Ser Phe Ala Asp
        755                 760                 765

Gly Gln Lys Val Ser Gln Gly Trp Ser Ala Glu Trp Ser Gln Ser Gly
    770                 775                 780

Thr Ala Val Thr Ala Lys Asn Ala Pro Trp Asn Gly Thr Leu Ala Ala
785                 790                 795                 800

Gly Ser Ser Val Ser Ile Gly Phe Asn Gly Thr His Asn Gly Thr Asn
                805                 810                 815

Thr Ala Pro Thr Ala Phe Thr Leu Asn Gly Val Ala Cys Thr Leu Gly
            820                 825                 830

<210> SEQ ID NO 3
<211> LENGTH: 558
<212> TYPE: PRT
<213> ORGANISM: Thermobifida fusca

<400> SEQUENCE: 3

Ala Gly Cys Ser Val Asp Tyr Thr Val Asn Ser Trp Gly Thr Gly Phe
1               5                   10                  15

Thr Ala Asn Val Thr Ile Thr Asn Leu Gly Ser Ala Ile Asn Gly Trp
                20                  25                  30

Thr Leu Glu Trp Asp Phe Pro Gly Asn Gln Gln Val Thr Asn Leu Trp
            35                  40                  45

Asn Gly Thr Tyr Thr Gln Ser Gly Gln His Val Ser Val Ser Asn Ala
        50                  55                  60

Pro Tyr Asn Ala Ser Ile Pro Ala Asn Gly Thr Val Glu Phe Gly Phe
65                  70                  75                  80

Asn Gly Ser Tyr Ser Gly Ser Asn Asp Ile Pro Ser Ser Phe Lys Leu
                85                  90                  95

Asn Gly Val Thr Cys Asp Gly Ser Asp Asp Pro Asp Pro Glu Pro Ser
            100                 105                 110

Pro Ser Pro Ser Pro Ser Pro Ser Pro Thr Asp Pro Asp Glu Pro Gly
        115                 120                 125

Gly Pro Thr Asn Pro Pro Thr Asn Pro Gly Glu Lys Val Asp Asn Pro
    130                 135                 140
```

```
Phe Glu Gly Ala Lys Leu Tyr Val Asn Pro Val Trp Ser Ala Lys Ala
145                 150                 155                 160

Ala Ala Glu Pro Gly Ser Ala Val Ala Asn Glu Ser Thr Ala Val
            165                 170                 175

Trp Leu Asp Arg Ile Gly Ala Ile Glu Gly Asn Asp Ser Pro Thr Thr
            180                 185                 190

Gly Ser Met Gly Leu Arg Asp His Leu Glu Glu Ala Val Arg Gln Ser
            195                 200                 205

Gly Gly Asp Pro Leu Thr Ile Gln Val Val Ile Tyr Asn Leu Pro Gly
210                 215                 220

Arg Asp Cys Ala Ala Leu Ala Ser Asn Gly Glu Leu Gly Pro Asp Glu
225                 230                 235                 240

Leu Asp Arg Tyr Lys Ser Glu Tyr Ile Asp Pro Ile Ala Asp Ile Met
            245                 250                 255

Trp Asp Phe Ala Asp Tyr Glu Asn Leu Arg Ile Val Ala Ile Ile Glu
            260                 265                 270

Ile Asp Ser Leu Pro Asn Leu Val Thr Asn Val Gly Gly Asn Gly Gly
            275                 280                 285

Thr Glu Leu Cys Ala Tyr Met Lys Gln Asn Gly Gly Tyr Val Asn Gly
            290                 295                 300

Val Gly Tyr Ala Leu Arg Lys Leu Gly Glu Ile Pro Asn Val Tyr Asn
305                 310                 315                 320

Tyr Ile Asp Ala Ala His His Gly Trp Ile Gly Trp Asp Ser Asn Phe
            325                 330                 335

Gly Pro Ser Val Asp Ile Phe Tyr Glu Ala Ala Asn Ala Ser Gly Ser
            340                 345                 350

Thr Val Asp Tyr Val His Gly Phe Ile Ser Asn Thr Ala Asn Tyr Ser
            355                 360                 365

Ala Thr Val Glu Pro Tyr Leu Asp Val Asn Gly Thr Val Asn Gly Gln
            370                 375                 380

Leu Ile Arg Gln Ser Lys Trp Val Asp Trp Asn Gln Tyr Val Asp Glu
385                 390                 395                 400

Leu Ser Phe Val Gln Asp Leu Arg Gln Ala Leu Ile Ala Lys Gly Phe
            405                 410                 415

Arg Ser Asp Ile Gly Met Leu Ile Asp Thr Ser Arg Asn Gly Trp Gly
            420                 425                 430

Gly Pro Asn Arg Pro Thr Gly Pro Ser Ser Ser Thr Asp Leu Asn Thr
            435                 440                 445

Tyr Val Asp Glu Ser Arg Ile Asp Arg Arg Ile His Pro Gly Asn Trp
450                 455                 460

Cys Asn Gln Ala Gly Ala Gly Leu Gly Glu Arg Pro Thr Val Asn Pro
465                 470                 475                 480

Ala Pro Gly Val Asp Ala Tyr Val Trp Val Lys Pro Pro Gly Glu Ser
            485                 490                 495

Asp Gly Ala Ser Glu Glu Ile Pro Asn Asp Glu Gly Lys Gly Phe Asp
            500                 505                 510

Arg Met Cys Asp Pro Thr Tyr Gln Gly Asn Ala Arg Asn Gly Asn Asn
            515                 520                 525

Pro Ser Gly Ala Leu Pro Asn Ala Pro Ile Ser Gly His Trp Phe Ser
            530                 535                 540

Ala Gln Phe Arg Glu Leu Leu Ala Asn Ala Tyr Pro Pro Leu
545                 550                 555
```

<210> SEQ ID NO 4
<211> LENGTH: 453
<212> TYPE: PRT
<213> ORGANISM: Humicola insolens

<400> SEQUENCE: 4

```
Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
        35                  40                  45

Thr Ser Thr Ser Ser Ser Ser Thr Thr Ser Arg Ala Thr Ser Thr Thr
    50                  55                  60

Ser Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
            260                 265                 270

Gly His Ala Gly Trp Leu Gly Trp Pro Ala Asn Ile Gln Pro Ala Ala
        275                 280                 285

Glu Leu Phe Ala Lys Ile Tyr Glu Asp Ala Gly Lys Pro Arg Ala Val
    290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
            340                 345                 350

Gln Phe Ile Val Asp Gln Gly Arg Ser Gly Lys Gln Pro Thr Gly Gln
        355                 360                 365

Lys Glu Trp Gly His Trp Cys Asn Ala Ile Gly Thr Gly Phe Gly Met
    370                 375                 380
```

```
Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
                420                 425                 430

Glu Ala Gly Gln Trp Phe Gln Ala Tyr Phe Glu Gln Leu Leu Arg Asn
                435                 440                 445

Ala Asn Pro Pro Phe
    450

<210> SEQ ID NO 5
<211> LENGTH: 408
<212> TYPE: PRT
<213> ORGANISM: Neocallimastix patriciarum

<400> SEQUENCE: 5

Ala Cys Gly Gly Ala Trp Ala Gln Cys Gly Gly Asn Phe His Gly
1               5                   10                  15

Asp Lys Cys Cys Val Ser Gly His Thr Cys Val Ser Ile Asn Gln Trp
                20                  25                  30

Tyr Ser Gln Cys Gln Pro Gly Gly Ala Pro Ser Asn Asn Ala Ser Asn
            35                  40                  45

Asn Asn Asn Asn Asn Asn Asn Asn Asn Asn Asn Asn Asn Asn Asn
    50                  55                  60

Asn Asn His Asn Asn Asn Asn Asn Asn Asn Asn Asn Asn Asn Gly
65                  70                  75                  80

Gly Ser Gly Ser Thr Lys Asn Phe Phe Asp Asn Gln Ile Tyr Ala Asn
                85                  90                  95

Pro Lys Phe Ile Glu Glu Val Asn Ser Ser Ile Pro Arg Leu Ser Tyr
                100                 105                 110

Asp Leu Gln Gln Lys Ala Gln Lys Val Lys Asn Val Pro Thr Ala Val
            115                 120                 125

Trp Leu Ala Trp Asp Gly Ala Thr Gly Glu Val Ala Gln His Leu Lys
130                 135                 140

Ala Ala Gly Ser Lys Thr Val Val Phe Ile Met Tyr Met Ile Pro Thr
145                 150                 155                 160

Arg Asp Cys Asn Ala Asn Ala Ser Ala Gly Gly Ala Gly Asn Leu Asn
                165                 170                 175

Thr Tyr Lys Gly Tyr Val Asp Asn Ile Ala Arg Thr Ile Arg Ser Tyr
                180                 185                 190

Pro Asn Ser Lys Val Val Met Ile Leu Glu Pro Asp Thr Leu Gly Asn
            195                 200                 205

Leu Val Thr Ala Asn Ser Ala Asn Cys Gln Asn Val Arg Asn Leu His
    210                 215                 220

Lys Asn Ala Leu Ser Tyr Gly Val Asn Val Phe Gly Ser Met Ser Asn
225                 230                 235                 240

Val Ser Val Tyr Leu Asp Ala Ala His Gly Ala Trp Leu Gly Ser Ser
                245                 250                 255

Thr Asp Lys Val Ala Ser Val Val Lys Glu Ile Leu Asn Asn Ala Pro
            260                 265                 270

Asn Gly Lys Ile Arg Gly Leu Ser Thr Asn Ile Ser Asn Tyr Gln Ser
        275                 280                 285

Ile Ser Ser Glu Tyr Gln Tyr His Gln Lys Leu Ala Ser Ala Leu Ala
```

```
                290                 295                 300
Ala Val Gly Val Pro Asn Met His Phe Ile Val Asp Thr Gly Arg Asn
305                 310                 315                 320

Gly Val Thr Ile Asn Ser Gly Thr Trp Cys Asn Leu Val Gly Thr Gly
                325                 330                 335

Leu Gly Glu Arg Pro Arg Gly Asn Pro Asn Ala Gly Met Pro Leu Leu
                340                 345                 350

Asp Ala Tyr Met Trp Leu Lys Thr Pro Gly Glu Ser Asp Gly Ser Ser
                355                 360                 365

Ser Gly Ser Arg Ala Asp Pro Asn Cys Ser Ser Asn Asp Ser Leu Arg
370                 375                 380

Gly Ala Pro Asp Ala Gly Gln Trp Phe His Asp Tyr Phe Ala Gln Leu
385                 390                 395                 400

Val Arg Asn Ala Arg Pro Ser Phe
                405

<210> SEQ ID NO 6
<211> LENGTH: 412
<212> TYPE: PRT
<213> ORGANISM: Orpinomyces sp. PC-2

<400> SEQUENCE: 6

Ala Cys Gly Gly Ala Tyr Ala Gln Cys Gly Gly Glu Asn Phe Tyr Gly
1               5                   10                  15

Glu Lys Cys Cys Val Ser Gly Tyr Lys Cys Val Tyr Met Asn Gln Trp
                20                  25                  30

Tyr Ser Gln Cys Gln Pro Gly Ala Ser Ser Ser Asn Pro Pro Ser Asn
            35                  40                  45

Asn Ala Ser Asn Asn Asn Asn Asp Asn Asn Asn Asn Asn Asn Asn Asn
    50                  55                  60

Asn Asn Asn Asn Asn Asn Asn Asn Asn Asn Asn Asn Asn Ser Gly
65                  70                  75                  80

Ser Gly Ser Thr Gln Asn Phe Phe Thr Asn Gln Ile Tyr Ala Asn Pro
                85                  90                  95

Lys Phe Ile Glu Glu Val Asn Ser Ser Ile Pro Lys Leu Ser Trp Asp
                100                 105                 110

Leu Gln Gln Lys Ala Gln Lys Val Lys Asp Val Pro Thr Ala Val Trp
            115                 120                 125

Leu Ala Trp Glu Gly Ala Pro Gly Glu Val Glu Gln His Leu Lys Ala
130                 135                 140

Ala Gly Ser Lys Thr Val Val Phe Ile Leu Tyr Met Ile Pro Thr Arg
145                 150                 155                 160

Asp Cys Asn Ser Asn Ala Ser Ala Gly Gly Ala Gly Ser Leu Asn Thr
                165                 170                 175

Tyr Lys Gly Tyr Val Asp Asn Ile Ser Arg Thr Ile Arg Ser Tyr Pro
            180                 185                 190

Asn Ser Lys Val Val Met Val Leu Glu Pro Asp Thr Leu Gly Asn Leu
        195                 200                 205

Val Thr Gly Asn Ser Ala Asn Cys Gln Asn Val Arg Gln Leu His Lys
210                 215                 220

Asn Ala Leu Ser Tyr Ala Val Asn Val Tyr Gly Ala Met Asn Asn Val
225                 230                 235                 240

Ser Val Tyr Leu Asp Ala Ala His Gly Lys Trp Leu Gly Gly Val Thr
                245                 250                 255
```

```
Asp Lys Val Ala Ala Val Val Lys Glu Ile Leu Asn Asn Ala Pro Asn
            260                 265                 270
Gly Lys Ile Arg Gly Leu Ser Thr Asn Val Ser Asn Tyr Gln Pro Ile
        275                 280                 285
Ala Ser Glu Tyr Ser Tyr His Gln Lys Leu Ala Ser Ser Leu Ser Ala
    290                 295                 300
Val Gly Ile Pro Asn Met His Phe Ile Val Asp Thr Gly Arg Asn Gly
305                 310                 315                 320
Val Asp Val Ser Ala Ala Phe Asn Thr Ser Glu Thr Trp Cys Asn Phe
                325                 330                 335
Val Gly Thr Gly Phe Gly Glu Arg Pro Arg Gly Asn Pro Asn Ser Gly
            340                 345                 350
Met Pro Leu Leu Asp Ala Tyr Met Trp Leu Lys Thr Pro Arg Glu Ser
        355                 360                 365
Asp Gly Ser Ser Gly Ser Arg Ala Asp Pro Val Cys Ser Arg Ser
370                 375                 380
Asp Ser Leu Arg Gly Ala Pro Asp Ala Gly Gln Trp Phe His Asp Tyr
385                 390                 395                 400
Phe Val Gln Leu Leu Arg Asn Ala Arg Pro Gly Phe
                405                 410

<210> SEQ ID NO 7
<211> LENGTH: 440
<212> TYPE: PRT
<213> ORGANISM: Phanerochaete chrysosporium

<400> SEQUENCE: 7

Ala Ser Ser Glu Trp Gly Gln Cys Gly Gly Ile Gly Trp Thr Gly Pro
1               5                   10                  15
Thr Thr Cys Val Ser Gly Thr Thr Cys Thr Val Leu Asn Pro Tyr Tyr
            20                  25                  30
Ser Gln Cys Leu Pro Gly Ser Ala Val Thr Thr Thr Ser Val Ile Thr
        35                  40                  45
Ser His Ser Ser Val Ser Ser Val Ser Ser His Ser Gly Ser Ser
    50                  55                  60
Thr Ser Thr Ser Ser Pro Thr Gly Pro Thr Gly Thr Asn Pro Pro
65                  70                  75                  80
Pro Pro Ser Ala Asn Asn Pro Trp Thr Gly Phe Gln Ile Phe Leu Ser
                85                  90                  95
Pro Tyr Tyr Ala Asn Glu Val Ala Ala Ala Lys Gln Ile Thr Asp
            100                 105                 110
Pro Thr Leu Ser Ser Lys Ala Ala Ser Val Ala Asn Ile Pro Thr Phe
        115                 120                 125
Thr Trp Leu Asp Ser Val Ala Lys Ile Pro Asp Leu Gly Thr Tyr Leu
    130                 135                 140
Ala Ser Ala Ser Ala Leu Gly Lys Ser Thr Gly Thr Lys Gln Leu Val
145                 150                 155                 160
Gln Ile Val Ile Tyr Asp Leu Pro Asp Arg Asp Cys Ala Ala Lys Ala
                165                 170                 175
Ser Asn Gly Glu Phe Ser Ile Ala Asn Asn Gly Gln Ala Asn Tyr Glu
            180                 185                 190
Asn Tyr Ile Asp Gln Ile Val Ala Gln Ile Gln Gln Phe Pro Asp Val
        195                 200                 205
Arg Val Val Ala Val Ile Glu Pro Asp Ser Leu Ala Asn Leu Val Thr
    210                 215                 220
```

-continued

```
Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
            245                 250                 255

Tyr Met Asp Ala Gly His Ala Gly Trp Leu Gly Trp Pro Ala Asn Leu
        260                 265                 270

Ser Pro Ala Ala Gln Leu Phe Thr Gln Val Trp Gln Asn Ala Gly Lys
    275                 280                 285

Ser Pro Phe Ile Lys Gly Leu Ala Thr Asn Val Ala Asn Tyr Asn Ala
290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
            325                 330                 335

Gly Trp Asp Ala Thr Phe Ile Val Asp Gln Gly Arg Ser Gly Val Gln
        340                 345                 350

Asn Ile Arg Gln Gln Trp Gly Asp Trp Cys Asn Ile Lys Gly Ala Gly
    355                 360                 365

Phe Gly Thr Arg Pro Thr Thr Asn Thr Gly Ser Gln Phe Ile Asp Ser
370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
            405                 410                 415

Pro Ala Pro Glu Ala Gly Thr Trp Phe Gln Ala Tyr Phe Gln Thr Leu
        420                 425                 430

Val Ser Ala Ala Asn Pro Pro Leu
    435                 440

<210> SEQ ID NO 8
<211> LENGTH: 471
<212> TYPE: PRT
<213> ORGANISM: Piromyces sp. E2

<400> SEQUENCE: 8

Cys Phe Ser Glu Arg Leu Gly Tyr Pro Cys Cys Arg Gly Asn Glu Val
1               5                   10                  15

Phe Tyr Thr Asp Asn Asp Gly Asp Trp Gly Val Glu Asn Gly Asn Trp
            20                  25                  30

Cys Gly Ile Gly Gly Ala Ser Ala Thr Thr Cys Trp Ser Gln Ala Leu
        35                  40                  45

Gly Tyr Pro Cys Cys Thr Ser Thr Ser Asp Val Ala Tyr Val Asp Gly
    50                  55                  60

Asp Gly Asn Trp Gly Val Glu Asn Gly Asn Trp Cys Gly Ile Ile Ala
65                  70                  75                  80

Gly Gly Asn Ser Ser Asn Asn Asn Ser Gly Ser Thr Ile Asn Val Gly
            85                  90                  95

Asp Val Thr Ile Gly Asn Gln Tyr Thr His Thr Gly Asn Pro Phe Ala
        100                 105                 110

Gly His Lys Phe Phe Ile Asn Pro Tyr Tyr Thr Ala Glu Val Asp Gly
    115                 120                 125

Ala Ile Ala Gln Ile Ser Asn Ala Ser Leu Arg Ala Lys Ala Glu Lys
130                 135                 140

Met Lys Glu Phe Ser Asn Ala Ile Trp Leu Asp Thr Ile Lys Asn Met
```

```
                145                 150                 155                 160
Asn Glu Trp Leu Glu Lys Asn Leu Lys Tyr Ala Leu Ala Glu Gln Asn
                165                 170                 175
Glu Thr Gly Lys Thr Val Leu Thr Val Phe Val Val Tyr Asp Leu Pro
            180                 185                 190
Gly Arg Asp Cys His Ala Leu Ala Ser Asn Gly Glu Leu Leu Ala Asn
            195                 200                 205
Asp Ser Asp Trp Ala Arg Tyr Gln Ser Glu Tyr Ile Asp Val Ile Glu
        210                 215                 220
Glu Lys Leu Lys Thr Tyr Lys Ser Gln Pro Val Val Leu Val Val Glu
225                 230                 235                 240
Pro Asp Ser Leu Ala Asn Met Val Thr Asn Leu Asp Ser Thr Pro Ala
                245                 250                 255
Cys Arg Asp Ser Glu Lys Tyr Tyr Met Asp Gly His Ala Tyr Leu Ile
                260                 265                 270
Lys Lys Leu Gly Val Leu Pro His Val Ala Met Tyr Leu Asp Ile Gly
            275                 280                 285
His Ala Phe Trp Leu Gly Trp Asp Asp Asn Arg Leu Lys Ala Gly Lys
        290                 295                 300
Val Tyr Ser Lys Val Ile Gln Ser Gly Ala Pro Gly Asn Val Arg Gly
305                 310                 315                 320
Phe Ala Ser Asn Val Ala Asn Tyr Thr Pro Trp Glu Asp Pro Thr Leu
                325                 330                 335
Ser Arg Gly Pro Asp Thr Glu Trp Asn Pro Cys Pro Asp Glu Lys Arg
            340                 345                 350
Tyr Ile Glu Ala Met Tyr Lys Asp Phe Lys Ser Ala Gly Ile Lys Ser
        355                 360                 365
Val Tyr Phe Ile Asp Asp Thr Ser Arg Asn Gly His Lys Thr Asp Arg
    370                 375                 380
Thr His Pro Gly Glu Trp Cys Asn Gln Thr Gly Val Gly Ile Gly Ala
385                 390                 395                 400
Arg Pro Gln Ala Asn Pro Ile Ser Gly Met Asp Tyr Leu Asp Ala Phe
                405                 410                 415
Tyr Trp Val Lys Pro Leu Gly Glu Ser Asp Gly Tyr Ser Asp Thr Thr
            420                 425                 430
Ala Val Arg Tyr Asp Gly Tyr Cys Gly His Ala Thr Ala Met Lys Pro
        435                 440                 445
Ala Pro Glu Ala Gly Gln Trp Phe Gln Lys His Phe Glu Gln Gly Leu
    450                 455                 460
Glu Asn Ala Asn Pro Pro Leu
465                 470

<210> SEQ ID NO 9
<211> LENGTH: 380
<212> TYPE: PRT
<213> ORGANISM: Mycobacterium tuberculosis

<400> SEQUENCE: 9

Met Thr Arg Arg Thr Gly Gln Arg Trp Arg Gly Thr Leu Pro Gly Arg
1               5                   10                  15
Arg Pro Trp Thr Arg Pro Ala Pro Ala Thr Cys Arg Arg His Leu Ala
            20                  25                  30
Phe Val Glu Leu Arg His Tyr Phe Ala Arg Val Met Ser Ser Ala Ile
        35                  40                  45
```

```
Gly Ser Val Ala Arg Trp Ile Val Pro Leu Leu Gly Val Ala Val
 50                  55                  60

Ala Ser Ile Gly Val Ile Ala Asp Pro Val Arg Val Val Arg Ala Pro
 65                  70                  75                  80

Ala Leu Ile Leu Val Asp Ala Ala Asn Pro Leu Ala Gly Lys Pro Phe
                 85                  90                  95

Tyr Val Asp Pro Ala Ser Ala Ala Met Val Ala Arg Asn Ala Asn
                100                 105                 110

Pro Pro Asn Ala Glu Leu Thr Ser Val Ala Asn Thr Pro Gln Ser Tyr
            115                 120                 125

Trp Leu Asp Gln Ala Phe Pro Pro Ala Thr Val Gly Gly Thr Val Ala
    130                 135                 140

Arg Tyr Thr Gly Ala Ala Gln Ala Ala Gly Ala Met Pro Val Leu Thr
145                 150                 155                 160

Leu Tyr Gly Ile Pro His Arg Asp Cys Gly Ser Tyr Ala Ser Gly Gly
                165                 170                 175

Phe Ala Thr Gly Thr Asp Tyr Arg Gly Trp Ile Asp Ala Val Ala Ser
                180                 185                 190

Gly Leu Gly Ser Ser Pro Ala Thr Ile Ile Val Glu Pro Asp Ala Leu
                195                 200                 205

Ala Met Ala Asp Cys Leu Ser Pro Asp Gln Arg Gln Glu Arg Phe Asp
    210                 215                 220

Leu Val Arg Tyr Ala Val Asp Thr Leu Thr Arg Asp Pro Ala Ala Ala
225                 230                 235                 240

Val Tyr Val Asp Ala Gly His Ser Arg Trp Leu Ser Ala Glu Ala Met
                245                 250                 255

Ala Ala Arg Leu Asn Asp Val Gly Val Gly Arg Ala Arg Gly Phe Ser
                260                 265                 270

Leu Asn Val Ser Asn Phe Tyr Thr Thr Asp Glu Glu Ile Gly Tyr Gly
                275                 280                 285

Glu Ala Ile Ser Gly Leu Thr Asn Gly Ser His Tyr Val Ile Asp Thr
    290                 295                 300

Ser Arg Asn Gly Ala Gly Pro Ala Pro Asp Ala Pro Leu Asn Trp Cys
305                 310                 315                 320

Asn Pro Ser Gly Arg Ala Leu Gly Ala Pro Pro Thr Thr Ala Thr Ala
                325                 330                 335

Gly Ala His Ala Asp Ala Tyr Leu Trp Ile Lys Arg Pro Gly Glu Ser
                340                 345                 350

Asp Gly Thr Cys Gly Arg Gly Glu Pro Gln Ala Gly Arg Phe Val Ser
    355                 360                 365

Gln Tyr Ala Ile Asp Leu Ala His Asn Ala Gly Gln
    370                 375                 380

<210> SEQ ID NO 10
<211> LENGTH: 410
<212> TYPE: PRT
<213> ORGANISM: Thermobifida fusca

<400> SEQUENCE: 10

Asn Asp Ser Pro Phe Tyr Val Asn Pro Asn Met Ser Ser Ala Glu Trp
 1               5                  10                  15

Val Arg Asn Asn Pro Asn Asp Pro Arg Thr Pro Val Ile Arg Asp Arg
                 20                  25                  30

Ile Ala Ser Val Pro Gln Gly Thr Trp Phe Ala His His Asn Pro Gly
                 35                  40                  45
```

```
Gln Ile Thr Gly Gln Val Asp Ala Leu Met Ser Ala Gln Ala Ala
         50                  55                  60

Gly Lys Ile Pro Ile Leu Val Val Tyr Asn Ala Pro Gly Arg Asp Cys
 65                  70                  75                  80

Gly Asn His Ser Ser Gly Gly Ala Pro Ser His Ser Ala Tyr Arg Ser
                 85                  90                  95

Trp Ile Asp Glu Phe Ala Ala Gly Leu Lys Asn Arg Pro Ala Tyr Ile
                100                 105                 110

Ile Val Glu Pro Asp Leu Ile Ser Leu Met Ser Ser Cys Met Gln His
            115                 120                 125

Val Gln Gln Glu Val Leu Glu Thr Met Ala Tyr Ala Gly Lys Ala Leu
        130                 135                 140

Lys Ala Gly Ser Ser Gln Ala Arg Ile Tyr Phe Asp Ala Gly His Ser
145                 150                 155                 160

Ala Trp His Ser Pro Ala Gln Met Ala Ser Trp Leu Gln Gln Ala Asp
                165                 170                 175

Ile Ser Asn Ser Ala His Gly Ile Ala Thr Asn Thr Ser Asn Tyr Arg
            180                 185                 190

Trp Thr Ala Asp Glu Val Ala Tyr Ala Lys Ala Val Leu Ser Ala Ile
        195                 200                 205

Gly Asn Pro Ser Leu Arg Ala Val Ile Asp Thr Ser Arg Asn Gly Asn
210                 215                 220

Gly Pro Ala Gly Asn Glu Trp Cys Asp Pro Ser Gly Arg Ala Ile Gly
225                 230                 235                 240

Thr Pro Ser Thr Thr Asn Thr Gly Asp Pro Met Ile Asp Ala Phe Leu
                245                 250                 255

Trp Ile Lys Leu Pro Gly Glu Ala Asp Gly Cys Ile Ala Gly Ala Gly
            260                 265                 270

Gln Phe Val Pro Gln Ala Ala Tyr Glu Met Ala Ile Ala Ala Gly Gly
        275                 280                 285

Thr Asn Pro Asn Pro Asn Pro Asn Pro Thr Pro Thr Pro Thr Pro Thr
290                 295                 300

Pro Thr Pro Pro Gly Ser Ser Gly Ala Cys Thr Ala Thr Tyr Thr
305                 310                 315                 320

Ile Ala Asn Glu Trp Asn Asp Gly Phe Gln Ala Thr Val Thr Val Thr
                325                 330                 335

Ala Asn Gln Asn Ile Thr Gly Trp Thr Val Thr Trp Thr Phe Thr Asp
            340                 345                 350

Gly Gln Thr Ile Thr Asn Ala Trp Asn Ala Asp Val Ser Thr Ser Gly
        355                 360                 365

Ser Ser Val Thr Ala Arg Asn Val Gly His Asn Gly Thr Leu Ser Gln
370                 375                 380

Gly Ala Ser Thr Glu Phe Gly Phe Val Gly Ser Lys Gly Asn Ser Asn
385                 390                 395                 400

Ser Val Pro Thr Leu Thr Cys Ala Ala Ser
                405                 410

<210> SEQ ID NO 11
<211> LENGTH: 348
<212> TYPE: PRT
<213> ORGANISM: Humicola insolens

<400> SEQUENCE: 11

Gln Ser Gly Asn Pro Phe Ser Gly Arg Thr Leu Leu Val Asn Ser Asp
```

```
                  1               5                  10                 15
Tyr Ser Ser Lys Leu Asp Gln Thr Arg Gln Ala Phe Leu Ser Arg Gly
                 20                 25                 30

Asp Gln Thr Asn Ala Ala Lys Val Lys Tyr Val Gln Glu Lys Val Gly
                 35                 40                 45

Thr Phe Tyr Trp Ile Ser Asn Ile Phe Leu Leu Arg Asp Ile Asp Val
         50                 55                 60

Ala Ile Gln Asn Ala Arg Ala Ala Lys Ala Arg Gly Glu Asn Pro Ile
 65                 70                 75                 80

Val Gly Leu Val Leu Tyr Asn Leu Pro Asp Arg Asp Cys Ser Ala Gly
                 85                 90                 95

Glu Ser Ser Gly Glu Leu Lys Leu Ser Gln Asn Gly Leu Asn Arg Tyr
                100                105                110

Lys Asn Glu Tyr Val Asn Pro Phe Ala Gln Lys Leu Lys Ala Ala Ser
            115                120                125

Asp Val Gln Phe Ala Val Ile Leu Glu Pro Asp Ala Ile Gly Asn Met
        130                135                140

Val Thr Gly Thr Ser Ala Phe Cys Arg Asn Ala Arg Gly Pro Gln Gln
145                150                155                160

Glu Ala Ile Gly Tyr Ala Ile Ser Gln Leu Gln Ala Ser His Ile His
                165                170                175

Leu Tyr Leu Asp Val Ala Asn Gly Gly Trp Leu Gly Trp Ala Asp Lys
            180                185                190

Leu Glu Pro Thr Ala Gln Glu Val Ala Thr Ile Leu Gln Lys Ala Gly
            195                200                205

Asn Asn Ala Lys Ile Arg Gly Phe Ser Ser Asn Val Ser Asn Tyr Asn
210                215                220

Pro Tyr Ser Thr Ser Asn Pro Pro Tyr Thr Ser Gly Ser Pro Ser
225                230                235                240

Pro Asp Glu Ser Arg Tyr Ala Thr Asn Ile Ala Asn Ala Met Arg Gln
                245                250                255

Arg Gly Leu Pro Thr Gln Phe Ile Ile Asp Gln Ser Arg Val Ala Leu
            260                265                270

Ser Gly Ala Arg Ser Glu Trp Gly Gln Trp Cys Asn Val Asn Pro Ala
        275                280                285

Gly Phe Gly Gln Pro Phe Thr Thr Asn Thr Asn Asn Pro Asn Val Asp
    290                295                300

Ala Ile Val Trp Val Lys Pro Gly Gly Glu Ser Asp Gly Gln Cys Gly
305                310                315                320

Met Gly Gly Ala Pro Ala Ala Gly Met Trp Phe Asp Ala Tyr Ala Gln
                325                330                335

Met Leu Thr Gln Asn Ala His Asp Glu Ile Ala Arg
            340                345

<210> SEQ ID NO 12
<211> LENGTH: 447
<212> TYPE: PRT
<213> ORGANISM: Trichoderma reesei

<400> SEQUENCE: 12

Gln Ala Cys Ser Ser Val Trp Gly Gln Cys Gly Gly Gln Asn Trp Ser
1               5                  10                 15

Gly Pro Thr Cys Cys Ala Ser Gly Ser Thr Cys Val Tyr Ser Asn Asp
                20                 25                 30
```

```
Tyr Tyr Ser Gln Cys Leu Pro Gly Ala Ala Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                    85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                    165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
    195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                    245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
    275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                    325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Trp Gly Asp Trp Cys
    355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                    405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
    435                 440                 445
```

<210> SEQ ID NO 13
<211> LENGTH: 447
<212> TYPE: PRT
<213> ORGANISM: Trichoderma reesei

<400> SEQUENCE: 13

```
Gln Ala Cys Ser Ser Val Trp Gly Gln Cys Gly Gly Gln Asn Trp Ser
  1               5                  10                  15

Gly Pro Thr Cys Cys Ala Ser Gly Ser Thr Cys Val Tyr Ser Asn Asp
             20                  25                  30

Tyr Tyr Ser Gln Cys Leu Pro Gly Ala Ala Ser Ser Ser Ser Ser Thr
         35                  40                  45

Arg Ala Ala Ser Thr Thr Ser Arg Val Ser Pro Thr Thr Ser Arg Ser
 50                  55                  60

Ser Ser Ala Thr Pro Pro Gly Ser Thr Thr Thr Arg Val Pro Pro Val
 65                  70                  75                  80

Glu Ser Gly Thr Ala Thr Tyr Ser Gly Asn Pro Phe Val Gly Val Thr
                 85                  90                  95

Pro Trp Ala Asn Ala Tyr Tyr Ala Ser Glu Val Ser Ser Leu Ala Ile
            100                 105                 110

Pro Ser Leu Thr Gly Ala Met Ala Thr Ala Ala Ala Ala Val Ala Lys
        115                 120                 125

Val Pro Ser Phe Met Trp Leu Asp Thr Leu Asp Lys Thr Pro Leu Met
130                 135                 140

Glu Gln Thr Leu Ala Asp Ile Arg Thr Ala Asn Lys Asn Gly Gly Asn
145                 150                 155                 160

Tyr Ala Gly Gln Phe Val Val Tyr Asp Leu Pro Asp Arg Asp Cys Ala
                165                 170                 175

Ala Leu Ala Ser Asn Gly Glu Tyr Ser Ile Ala Asp Gly Gly Val Ala
            180                 185                 190

Lys Tyr Lys Asn Tyr Ile Asp Thr Ile Arg Gln Ile Val Val Glu Tyr
        195                 200                 205

Ser Asp Ile Arg Thr Leu Leu Val Ile Glu Pro Asp Ser Leu Ala Asn
    210                 215                 220

Leu Val Thr Asn Leu Ser Thr Pro Lys Cys Ala Asn Ala Gln Ser Ala
225                 230                 235                 240

Tyr Leu Glu Cys Ile Asn Tyr Ala Val Thr Gln Leu Asn Leu Pro Asn
                245                 250                 255

Val Ala Met Tyr Leu Asp Ala Gly His Ala Gly Trp Leu Gly Trp Pro
            260                 265                 270

Ala Asn Gln Asp Pro Ala Ala Gln Leu Phe Ala Asn Val Tyr Lys Asn
        275                 280                 285

Ala Ser Ser Pro Arg Ala Leu Arg Gly Leu Ala Thr Asn Val Ala Ser
    290                 295                 300

Tyr Asn Gly Trp Asn Ile Thr Ser Pro Pro Ser Tyr Thr Gln Gly Asn
305                 310                 315                 320

Ala Val Tyr Asn Glu Lys Leu Tyr Ile His Ala Ile Gly Pro Leu Leu
                325                 330                 335

Ala Asn His Gly Trp Ser Asn Ala Phe Phe Ile Thr Asp Gln Gly Arg
            340                 345                 350

Ser Gly Lys Gln Pro Thr Gly Gln Gln Gln Trp Gly Asp Trp Cys Asn
        355                 360                 365

Val Ile Gly Thr Gly Phe Gly Ile Arg Pro Ser Ala Asn Thr Gly
    370                 375                 380
```

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 14
<211> LENGTH: 447
<212> TYPE: PRT
<213> ORGANISM: Trichoderma reesei

<400> SEQUENCE: 14

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Ser Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

```
Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 15
<211> LENGTH: 447
<212> TYPE: PRT
<213> ORGANISM: Trichoderma reesei

<400> SEQUENCE: 15

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
```

```
                        245                 250                 255
Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Ser Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Trp Cys
                355                 360                 365

Asn Val Ile Gly Thr Gly Phe Gly Ile Arg Pro Ser Ala Asn Thr Gly
                370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 16
<211> LENGTH: 447
<212> TYPE: PRT
<213> ORGANISM: Trichoderma reesei

<400> SEQUENCE: 16

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175
```

```
Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 17
<211> LENGTH: 447
<212> TYPE: PRT
<213> ORGANISM: Trichoderma reesei

<400> SEQUENCE: 17

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro Val
65                  70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
            100                 105                 110
```

```
Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Ser Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Ser Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 18
<211> LENGTH: 447
<212> TYPE: PRT
<213> ORGANISM: Trichoderma reesei

<400> SEQUENCE: 18

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
```

```
                35                  40                  45
Arg Ala Ala Ser Thr Thr Ser Arg Val Ser Pro Thr Thr Ser Arg Ser
 50                  55                  60

Ser Ser Ala Thr Pro Pro Gly Ser Thr Thr Thr Arg Val Pro Pro
 65                  70                  75                  80

Val Gly Ser Gly Thr Ala Thr Tyr Ser Gly Asn Pro Phe Val Gly Val
                 85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
195                 200                 205

Tyr Ser Asp Ile Arg Thr Leu Leu Val Ile Glu Pro Asp Ser Leu Ala
210                 215                 220

Asn Leu Val Thr Asn Leu Ser Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 19
```

<211> LENGTH: 447
<212> TYPE: PRT
<213> ORGANISM: Trichoderma reesei

<400> SEQUENCE: 19

```
Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Ser Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
```

```
                385                 390                 395                 400
Asp Gly Thr Ser Asp Ser Ala Pro Gln Phe Asp Pro His Cys Ala
                405                 410                 415
Leu Pro Asp Ala Leu Gln Pro Ala Pro Gln Ala Gly Ala Trp Phe Gln
                420                 425                 430
Ala Tyr Phe Val Gln Leu Leu Thr Asn Ala Asn Pro Ser Phe Leu
        435                 440                 445

<210> SEQ ID NO 20
<211> LENGTH: 447
<212> TYPE: PRT
<213> ORGANISM: Trichoderma reesei

<400> SEQUENCE: 20

Gln Ala Cys Ser Ser Val Trp Gly Gln Cys Gly Gly Gln Asn Trp Ser
1               5                   10                  15
Gly Pro Thr Cys Cys Ala Ser Gly Ser Thr Cys Val Tyr Ser Asn Asp
                20                  25                  30
Tyr Tyr Ser Gln Cys Leu Pro Gly Ala Ala Ser Ser Ser Ser Thr
        35                  40                  45
Arg Ala Ala Ser Thr Thr Ser Arg Val Ser Pro Thr Thr Ser Arg Ser
    50                  55                  60
Ser Ser Ala Thr Pro Pro Pro Gly Ser Thr Thr Thr Arg Val Pro Pro
65                  70                  75                  80
Val Gly Ser Gly Thr Ala Thr Tyr Ser Gly Asn Pro Phe Val Gly Val
                85                  90                  95
Thr Pro Trp Ala Asn Ala Tyr Tyr Ala Ser Glu Val Ser Ser Leu Ala
                100                 105                 110
Ile Pro Ser Leu Thr Gly Ala Met Ala Thr Ala Ala Ala Val Ala
            115                 120                 125
Lys Val Pro Ser Phe Met Trp Leu Asp Thr Leu Asp Lys Thr Pro Leu
            130                 135                 140
Met Glu Gln Thr Leu Ala Asp Ile Arg Thr Ala Asn Lys Asn Gly Gly
145                 150                 155                 160
Asn Tyr Ala Gly Gln Phe Val Val Tyr Asp Leu Pro Asp Arg Asp Cys
                165                 170                 175
Ala Ala Leu Ala Ser Asn Gly Glu Tyr Ser Ile Ala Asp Gly Gly Val
            180                 185                 190
Ala Lys Tyr Lys Asn Tyr Ile Asp Thr Ile Arg Gln Ile Val Val Glu
        195                 200                 205
Tyr Ser Asp Ile Arg Thr Leu Leu Val Ile Glu Pro Asp Ser Leu Ala
    210                 215                 220
Asn Leu Val Thr Asn Leu Ser Thr Pro Lys Cys Ala Asn Ala Gln Ser
225                 230                 235                 240
Ala Tyr Leu Glu Cys Ile Asn Tyr Ala Val Thr Gln Leu Asn Leu Pro
                245                 250                 255
Asn Val Ala Met Tyr Leu Asp Ala Gly His Ala Gly Trp Leu Gly Trp
                260                 265                 270
Pro Ala Asn Gln Asp Pro Ala Ala Gln Leu Phe Ala Asn Val Tyr Lys
            275                 280                 285
Asn Ala Ser Ser Pro Arg Ala Leu Arg Gly Leu Ala Thr Asn Val Ala
        290                 295                 300
Ser Tyr Asn Gly Trp Asn Ile Thr Ser Pro Pro Ser Tyr Thr Gln Gly
305                 310                 315                 320
```

```
Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
        340                 345                 350

Arg Ser Gly Lys Gln Pro Thr Gly Gln Gln Trp Gly Asp Trp Cys
            355                 360                 365

Asn Val Ile Gly Thr Gly Phe Gly Ile Arg Pro Ser Ala Asn Thr Gly
        370                 375                 380

Asp Ser Leu Leu Asp Ser Phe Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
        435                 440                 445

<210> SEQ ID NO 21
<211> LENGTH: 453
<212> TYPE: PRT
<213> ORGANISM: Humicola insolens

<400> SEQUENCE: 21

Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
        35                  40                  45

Thr Ser Thr Ser Ser Ser Ser Thr Ser Arg Ala Thr Ser Thr Thr
    50                  55                  60

Ser Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255
```

```
Ala Leu Lys Gln Leu Asp Leu Pro His Val Ala Met Tyr Met Asp Ala
                260                 265                 270
Gly His Ala Gly Trp Leu Gly Trp Pro Ala Asn Ile Gln Pro Ala Ala
            275                 280                 285
Glu Leu Phe Ala Lys Ile Tyr Glu Asp Ala Gly Lys Pro Arg Ala Val
        290                 295                 300
Arg Gly Leu Ala Thr Asn Val Ala Asn Tyr Asn Ala Trp Ser Ile Ser
305                 310                 315                 320
Ser Pro Pro Pro Tyr Thr Ser Pro Asn Pro Asn Tyr Asp Glu Lys His
                325                 330                 335
Tyr Ile Glu Ala Phe Arg Pro Leu Leu Glu Ala Arg Gly Phe Pro Ala
            340                 345                 350
Gln Phe Ile Val Asp Gln Gly Arg Ser Gly Lys Gln Pro Thr Gly Gln
        355                 360                 365
Lys Glu Trp Gly His Trp Cys Asn Ala Ile Gly Thr Gly Phe Gly Met
370                 375                 380
Arg Pro Thr Ala Asn Thr Gly His Gln Tyr Val Asp Ala Phe Val Trp
385                 390                 395                 400
Val Lys Pro Gly Gly Glu Cys Asp Gly Thr Ser Asp Thr Thr Ala Ala
                405                 410                 415
Arg Tyr Asp Pro His Cys Gly Leu Glu Asp Ala Leu Lys Pro Ala Pro
            420                 425                 430
Glu Ala Gly Gln Trp Phe Gln Ala Tyr Phe Glu Gln Leu Leu Arg Asn
        435                 440                 445
Ala Asn Pro Pro Phe
        450

<210> SEQ ID NO 22
<211> LENGTH: 440
<212> TYPE: PRT
<213> ORGANISM: Phanerochaete chrysosporium

<400> SEQUENCE: 22

Ala Ser Ser Glu Trp Gly Gln Cys Gly Gly Ile Gly Trp Thr Gly Pro
1               5                   10                  15
Thr Thr Cys Val Ser Gly Thr Thr Cys Thr Val Leu Asn Pro Tyr Tyr
                20                  25                  30
Ser Gln Cys Leu Pro Gly Ser Ala Val Thr Thr Ser Val Ile Thr
            35                  40                  45
Ser His Ser Ser Ser Val Ser Ser Val Ser Ser His Ser Gly Ser Ser
        50                  55                  60
Thr Ser Thr Ser Ser Pro Thr Gly Pro Thr Gly Thr Asn Pro Pro Pro
65                  70                  75                  80
Pro Pro Ser Ala Asn Asn Pro Trp Thr Gly Phe Gln Ile Phe Leu Ser
                85                  90                  95
Pro Tyr Tyr Ala Asn Glu Val Ala Ala Ala Lys Gln Ile Thr Asp
            100                 105                 110
Pro Thr Leu Ser Ser Lys Ala Ala Ser Val Ala Asn Ile Pro Thr Phe
        115                 120                 125
Thr Trp Leu Asp Ser Val Ala Lys Ile Pro Asp Leu Gly Thr Tyr Leu
    130                 135                 140
Ala Ser Ala Ser Ala Leu Gly Lys Ser Thr Gly Thr Lys Gln Leu Val
145                 150                 155                 160
Gln Ile Val Ile Tyr Asp Leu Pro Asp Arg Asp Cys Ala Ala Lys Ala
```

-continued

```
                165                 170                 175
Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
        435                 440

<210> SEQ ID NO 23
<211> LENGTH: 459
<212> TYPE: PRT
<213> ORGANISM: Trichoderma reesei

<400> SEQUENCE: 23

Asp Tyr Lys Asp Asp Asp Asp Lys Glu Phe Leu Glu Ala Ser Cys Ser
1               5                   10                  15

Ser Val Trp Gly Gln Cys Gly Gly Gln Asn Trp Ser Gly Pro Thr Cys
            20                  25                  30

Cys Ala Ser Gly Ser Thr Cys Val Tyr Ser Asn Asp Tyr Tyr Ser Gln
        35                  40                  45

Cys Leu Pro Gly Ala Ala Ser Ser Ser Ser Thr Arg Ala Ala Ser
    50                  55                  60

Thr Thr Ser Arg Val Ser Pro Thr Thr Ser Arg Ser Ser Ser Ala Thr
65                  70                  75                  80

Pro Pro Pro Gly Ser Thr Thr Thr Arg Val Pro Pro Val Gly Ser Gly
                85                  90                  95
```

-continued

```
Thr Ala Thr Tyr Ser Gly Asn Pro Phe Val Gly Val Thr Pro Trp Ala
            100                 105                 110
Asn Ala Tyr Tyr Ala Ser Glu Val Ser Ser Leu Ala Ile Pro Ser Leu
        115                 120                 125
Thr Gly Ala Met Ala Thr Ala Ala Ala Val Ala Lys Val Pro Ser
    130                 135                 140
Phe Met Trp Leu Asp Thr Leu Asp Lys Thr Pro Leu Met Glu Gln Thr
145                 150                 155                 160
Leu Ala Asp Ile Arg Thr Ala Asn Lys Asn Gly Gly Asn Tyr Ala Gly
                165                 170                 175
Gln Phe Val Val Tyr Asp Leu Pro Asp Arg Asp Cys Ala Ala Leu Ala
            180                 185                 190
Ser Asn Gly Glu Tyr Ser Ile Ala Asp Gly Gly Val Ala Lys Tyr Lys
        195                 200                 205
Asn Tyr Ile Asp Thr Ile Arg Gln Ile Val Val Glu Tyr Ser Asp Ile
    210                 215                 220
Arg Thr Leu Leu Val Ile Glu Pro Asp Ser Leu Ala Asn Leu Val Thr
225                 230                 235                 240
Asn Leu Gly Thr Pro Lys Cys Ala Asn Ala Gln Ser Ala Tyr Leu Glu
                245                 250                 255
Cys Ile Asn Tyr Ala Val Thr Gln Leu Asn Leu Pro Asn Val Ala Met
            260                 265                 270
Tyr Leu Asp Ala Gly His Ala Gly Trp Leu Gly Trp Pro Ala Asn Gln
        275                 280                 285
Asp Pro Ala Ala Gln Leu Phe Ala Asn Val Tyr Lys Asn Ala Ser Ser
    290                 295                 300
Pro Arg Ala Leu Arg Gly Leu Ala Thr Asn Val Ala Asn Tyr Asn Gly
305                 310                 315                 320
Trp Asn Ile Thr Ser Pro Pro Ser Tyr Thr Gln Gly Asn Ala Val Tyr
                325                 330                 335
Asn Glu Lys Leu Tyr Ile His Ala Ile Gly Pro Leu Leu Ala Asn His
            340                 345                 350
Gly Trp Ser Asn Ala Phe Phe Ile Thr Asp Gln Gly Arg Ser Gly Lys
        355                 360                 365
Gln Pro Thr Gly Gln Gln Gln Trp Gly Asp Trp Cys Asn Val Ile Gly
    370                 375                 380
Thr Gly Phe Gly Ile Arg Pro Ser Ala Asn Thr Gly Asp Ser Leu Leu
385                 390                 395                 400
Asp Ser Phe Val Trp Val Lys Pro Gly Gly Glu Cys Asp Gly Thr Ser
                405                 410                 415
Asp Ser Ser Ala Pro Arg Phe Asp Ser His Cys Ala Leu Pro Asp Ala
            420                 425                 430
Leu Gln Pro Ala Pro Gln Ala Gly Ala Trp Phe Gln Ala Tyr Phe Val
        435                 440                 445
Gln Leu Leu Thr Asn Ala Asn Pro Ser Phe Leu
    450                 455
```

<210> SEQ ID NO 24
<211> LENGTH: 33
<212> TYPE: DNA
<213> ORGANISM: Artificial sequence
<220> FEATURE:
<223> OTHER INFORMATION: Primer sequence

<400> SEQUENCE: 24

-continued gataggcctg ctagctgctc aagcgtctgg ggc        33

<210> SEQ ID NO 25
<211> LENGTH: 36
<212> TYPE: DNA
<213> ORGANISM: Artificial sequence
<220> FEATURE:
<223> OTHER INFORMATION: Primer sequence

<400> SEQUENCE: 25
atcaggccta gatctggtac cttacaggaa cgatgg        36

<210> SEQ ID NO 26
<211> LENGTH: 31
<212> TYPE: DNA
<213> ORGANISM: Artificial sequence
<220> FEATURE:
<223> OTHER INFORMATION: Primer sequence

<400> SEQUENCE: 26
gatcagatct atggtctcct tcacctccct c        31

<210> SEQ ID NO 27
<211> LENGTH: 31
<212> TYPE: DNA
<213> ORGANISM: Artificial sequence
<220> FEATURE:
<223> OTHER INFORMATION: Primer sequence
<220> FEATURE:
<221> NAME/KEY: misc_feature
<222> LOCATION: (15)..(17)
<223> OTHER INFORMATION: n is a, c, g, or t

<400> SEQUENCE: 27
ccaacaaaag ggttnnntga atacgtagcg g        31

<210> SEQ ID NO 28
<211> LENGTH: 29
<212> TYPE: DNA
<213> ORGANISM: Artificial sequence
<220> FEATURE:
<223> OTHER INFORMATION: Primer sequence
<220> FEATURE:
<221> NAME/KEY: misc_feature
<222> LOCATION: (14)..(16)
<223> OTHER INFORMATION: n is a, c, g, or t

<400> SEQUENCE: 28
cccaaggagt gacnnnaaca aaagggttg        29

<210> SEQ ID NO 29
<211> LENGTH: 29
<212> TYPE: DNA
<213> ORGANISM: Artificial sequence
<220> FEATURE:
<223> OTHER INFORMATION: Primer sequence
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 29
ggtgaccaac ctcncnactc caaagtgtg        29

```
<210> SEQ ID NO 30
<211> LENGTH: 26
<212> TYPE: DNA
<213> ORGANISM: Artificial sequence
<220> FEATURE:
<223> OTHER INFORMATION: Primer sequence
<220> FEATURE:
<221> NAME/KEY: misc_feature
<222> LOCATION: (12)..(14)
<223> OTHER INFORMATION: n is a, c, g, or t

<400> SEQUENCE: 30
ccgcaaacac tnnngactcg ttgctg                                          26

<210> SEQ ID NO 31
<211> LENGTH: 35
<212> TYPE: DNA
<213> ORGANISM: Artificial sequence
<220> FEATURE:
<223> OTHER INFORMATION: Primer sequence

<400> SEQUENCE: 31
ctaaagaaga agggtacat ttggataaaa gagac                                 35

<210> SEQ ID NO 32
<211> LENGTH: 35
<212> TYPE: DNA
<213> ORGANISM: Artificial sequence
<220> FEATURE:
<223> OTHER INFORMATION: Primer sequence

<400> SEQUENCE: 32
gtctctttta tccaaatgta ccccttcttc tttag                                35

<210> SEQ ID NO 33
<211> LENGTH: 25
<212> TYPE: DNA
<213> ORGANISM: Artificial sequence
<220> FEATURE:
<223> OTHER INFORMATION: Primer sequence

<400> SEQUENCE: 33
gatagaattc gctagctgct caagc                                           25

<210> SEQ ID NO 34
<211> LENGTH: 27
<212> TYPE: DNA
<213> ORGANISM: Artificial sequence
<220> FEATURE:
<223> OTHER INFORMATION: Primer sequence

<400> SEQUENCE: 34
gataggatcc ggtaccttta caggaac                                         27

<210> SEQ ID NO 35
<211> LENGTH: 29
<212> TYPE: DNA
<213> ORGANISM: Artificial sequence
<220> FEATURE:
<223> OTHER INFORMATION: Primer sequence

<400> SEQUENCE: 35
ggtgaccaac ctctctactc caaagtgtg                                       29

<210> SEQ ID NO 36
<211> LENGTH: 22
<212> TYPE: DNA
```

<213> ORGANISM: Artificial sequence
<220> FEATURE:
<223> OTHER INFORMATION: Primer sequence

<400> SEQUENCE: 36
caatgtcgcc agctacaacg gg                                           22

<210> SEQ ID NO 37
<211> LENGTH: 22
<212> TYPE: DNA
<213> ORGANISM: Artificial sequence
<220> FEATURE:
<223> OTHER INFORMATION: Primer sequence

<400> SEQUENCE: 37
cacaatttga cccccactgt gc                                           22

<210> SEQ ID NO 38
<211> LENGTH: 27
<212> TYPE: DNA
<213> ORGANISM: Artificial sequence
<220> FEATURE:
<223> OTHER INFORMATION: Primer sequence

<400> SEQUENCE: 38
gtacctccag tcggatcggg aaccgct                                      27

<210> SEQ ID NO 39
<211> LENGTH: 55
<212> TYPE: DNA
<213> ORGANISM: Artificial sequence
<220> FEATURE:
<223> OTHER INFORMATION: Primer sequence

<400> SEQUENCE: 39
agagactaca aggatgacga tgacaaggaa ttcctcgagg ctagctgctc aagcg       55

<210> SEQ ID NO 40
<211> LENGTH: 55
<212> TYPE: DNA
<213> ORGANISM: Artificial sequence
<220> FEATURE:
<223> OTHER INFORMATION: Primer sequence

<400> SEQUENCE: 40
gacggatcag cggccgctta ccgcgggtcg acgggcccgg taccttacag gaacg       55

<210> SEQ ID NO 41
<211> LENGTH: 35
<212> TYPE: DNA
<213> ORGANISM: Artificial sequence
<220> FEATURE:
<223> OTHER INFORMATION: Primer sequence

<400> SEQUENCE: 41
ctattgctag ctcggagtgg ggacagtgcg gtggc                             35

<210> SEQ ID NO 42
<211> LENGTH: 44
<212> TYPE: DNA
<213> ORGANISM: Artificial sequence
<220> FEATURE:
<223> OTHER INFORMATION: Primer sequence

<400> SEQUENCE: 42
ctattgaatt cggtacccta cagcggcggg ttggcagcag aaac                   44

<210> SEQ ID NO 43
<211> LENGTH: 54
<212> TYPE: DNA
<213> ORGANISM: Artificial sequence
<220> FEATURE:
<223> OTHER INFORMATION: Primer sequence

<400> SEQUENCE: 43
aaggatgacg atgacaagga attcctcgag gctagctcgg agtggggaca gtgc        54

<210> SEQ ID NO 44
<211> LENGTH: 54
<212> TYPE: DNA
<213> ORGANISM: Artificial sequence
<220> FEATURE:
<223> OTHER INFORMATION: Primer sequence

<400> SEQUENCE: 44
tgggacgctc gacggatcag cggccgctta ccgcggctac agcggcgggt tggc        54

<210> SEQ ID NO 45
<211> LENGTH: 27
<212> TYPE: DNA
<213> ORGANISM: Artificial sequence
<220> FEATURE:
<223> OTHER INFORMATION: Primer sequence

<400> SEQUENCE: 45
ccccgctacg accctacttg ttctctg                                      27

<210> SEQ ID NO 46
<211> LENGTH: 35
<212> TYPE: DNA
<213> ORGANISM: Artificial sequence
<220> FEATURE:
<223> OTHER INFORMATION: Primer sequence

<400> SEQUENCE: 46
ctattgctag ctgtgccccg acttggggcc agtgc                             35

<210> SEQ ID NO 47
<211> LENGTH: 44
<212> TYPE: DNA
<213> ORGANISM: Artificial sequence
<220> FEATURE:
<223> OTHER INFORMATION: Primer sequence

<400> SEQUENCE: 47
ctattgaatt cggtacctca gaacggcgga ttggcattac gaag                   44

<210> SEQ ID NO 48
<211> LENGTH: 54
<212> TYPE: DNA
<213> ORGANISM: Artificial sequence
<220> FEATURE:
<223> OTHER INFORMATION: Primer sequence

<400> SEQUENCE: 48
aaggatgacg atgacaagga attcctcgag gctagctgtg ccccgacttg gggc        54

<210> SEQ ID NO 49
<211> LENGTH: 54
<212> TYPE: DNA
<213> ORGANISM: Artificial sequence
<220> FEATURE:

-continued

```
<223> OTHER INFORMATION: Primer sequence

<400> SEQUENCE: 49
agcggccgct taccgcgggt cgacgggccc ggtacctcag aacggcggat tggc        54

<210> SEQ ID NO 50
<211> LENGTH: 27
<212> TYPE: DNA
<213> ORGANISM: Artificial sequence
<220> FEATURE:
<223> OTHER INFORMATION: Primer sequence

<400> SEQUENCE: 50
gcccgctacg accctcactg cggtctc                                      27
```

MODIFIED CELLULASES WITH INCREASED THERMOSTABILITY, THERMOPHILICITY, AND ALKALOPHILICITY

TECHNICAL FIELD

The present invention relates to modified cellulases. More specifically, the invention relates to modified Family 6 cellulases with improved thermostability, alkalophilicity and/or thermophilicity. The present invention also relates to genetic constructs comprising nucleotide sequences encoding for modified Family 6 cellulases, methods for the production of the modified Family 6 cellulase from host strains and the use of the modified Family 6 cellulases in the hydrolysis of cellulose.

BACKGROUND OF THE INVENTION

The most abundant polysaccharide in the biosphere, cellulose, consists of D-glucose units linked together in linear chains via β-1,4 glycosidic bonds. These chains can vary in length and often consist of many thousands of units. Cellulose chains form numerous intra- and intermolecular hydrogen bonds, which result in the formation of insoluble cellulose microfibrils. This crystalline cellulose is a recalcitrant material with a natural half-life of over five million years.

In order to access this important renewable carbon source, microorganisms, such as bacteria and fungi, produce a cocktail of enzymes to break down crystalline cellulose into glucose. Three general classes of cellulase enzymes act synergistically to hydrolyze the crystalline cellulose into the simple energy source glucose. Endo-β-1,4-glucanases (EC 3.2.1.4) randomly hydrolyze amorphous regions of crystalline cellulose generating oligosaccharides of various lengths and consequently new chain ends. Cellobiohydrolases (or exo-β-1,4-cellobiohydrolase, EC 3.2.1.91) hydrolyze processively cellobiose units from one end of the cellulose chain. Finally, β-1,4-glucosidases (EC 3.2.1.21) hydrolyze cellobiose into glucose.

Most cellobiohydrolases and endo-β-1,4-glucanases are multidomain proteins consisting of a catalytic core domain and a cellulose-binding domain separated by a flexible linker region. The cellulose-binding domain promotes adsorption of the enzyme to regions of the cellulosic substrate (Tomme, P., et al. 1988. *Eur. J. Biochem* 170:575-581; Lehtio J., et al. 2003 *Proc. Natl. Acad. Sci. USA.* 100:484-489), while the catalytic core domain is responsible for the cleavage of cellulose. The linker region may ensure an optimal interdomain distance between the core domain and the cellulose-binding domain (Srisodsuk M., et al. 1993. *J. Biol. Chem.* 268:20756-20761).

The catalytic domains are classified into the glycoside hydrolase families based on amino acid sequence similarities whereby a family comprises enzymes having similar fold and hydrolytic mechanisms but may differ in their substrate specificity. *Trichoderma reesei* contains known cellulase genes for two cellobiohydrolases, i.e., Cel7A (also known as CBH1, which is a member of Family 7) and Cel6A (CBH2), at least eight endo-β-1,4-glucanases, i.e., Cel7B (EG1), Cel5A (EG2), Cel12A (EG3), Cel61A (EG4), Cel45A (EG5), Cel74A (EG6), Cel61B (EG7), and Cel5B (EG8), and at least seven β-1,4-glucosidase, i.e., Cel3A (BG1), CellA (BG2), Cel3B (BG3), Cel3C (BG4), CellB (BG5), Cel3D, and Cel3E (Foreman, P. K., et al. 2003. *J. Biol. Chem.* 278:31988-31997).

*T. reesei* Cel6A (or TrCel6A) is one of the two major cellobiohydrolases secreted by this fungus and has been shown to be efficient in the enzymatic hydrolysis of crystalline cellulose. TrCel6A is a member of glycoside hydrolase Family 6, which comprises enzymes that hydrolyse β-1,4 glycosidic bonds with inversion of anomeric configuration and includes cellobiohydrolases as well as endo-β-1,4-glucanases. The three dimensional structures of TrCel6A (Rouvinen J., et al. 1990. *Science* 249:380-386. Erratum in: Science 1990 249:1359), *Thermobifida fusca* endo-β-1,4-glucanase Cel6A (TfCel6A, Spezio M., et al. 1993. *Biochemistry.* 32:9906-9916), *Humicola insolens* cellobiohydrolase Cel6A (HiCel6A, Varrot, A., et al. 1999 *Biochem. J.* 337:297-304), *Humicola insolens* endo-β-1,4-glucanase Cel6B (HiCel6B, Davies, G. J., et al. 2000. *Biochem. J.* 348: 201-207), and *Mycobacterium tuberculosis* H37Rv Cel6A (MtCel6A, Varrot. A., et al. 2005. *J. Biol. Chem.* 280:20181-20184) are known.

Applications of cellulase enzymes in industrial processes are numerous and have proven commercially useful within the textile industry for denim finishing and cotton softening; in the household and industrial detergents for color brightening, softening, and soil removal; in the pulp and paper industries for smoothing fiber, enhancing drainage, and de-inking; in the food industry for extracting and clarifying juice from fruits and vegetables, and for mashing; in the animal feed industry to improve their nutritional quality; and also, in the conversion of plant fibers into glucose that are fermented and distilled to make low $CO_2$ cellulose ethanol to reduce fossil fuel consumption, which is an emerging industry around the world (e.g. Gray K. A., et al. 2006. *Curr. Opin. Chem. Biol.* 10:141-146).

In order to obtain enzyme variants with improved stability properties, three strategies have generally been used within the art: 1) isolation of thermophilic enzymes from extremophiles, residing in severe environments such as extreme heat or cold, high salt concentrations or high or low pH conditions (e.g. U.S. Pat. No. 5,677,151 U.S. Pat. Appl. No. 20060053514); 2) protein engineering by rational design or site-directed mutagenesis, which relies on sequence homology and structural alignment within a family of proteins to identify potentially beneficial mutations using the principles of protein stability known in the art (reviewed in: Eijsink, V. G., et al. 2004. *J. Biotechnol.* 113:105-20.); and 3) directed evolution involving the construction of a mutant library with selection or screening to identify improved variants and involves a process of iterative cycles of producing variants with the desired properties (recently reviewed in: Eijsink V G, et al. 2005. *Biomol. Eng.* 22:21-30). This approach requires no structural or mechanistic information and can uncover unexpected beneficial mutations. Combining the above strategies has proven to be an efficient way to identify improved enzymes (Chica R. A., et al. 2005. *Curr. Opin. Biotechnol.* 16:378-384).

Using rational design, Zhang et al. (Zhan S et al., 2000. *Eur. J. Biochem.* 267:3101-15), introduced a new disulfide bond across the N- and C-terminal loops from TfCel6B using two double mutations, and four glycine residue mutations were chosen to improve thermostability. None of the mutations increased thermostability of this cellobiohydrolase and most mutations reduced thermostability by 5-10° C. Surprisingly, the double mutation N233C-D506C showed a decrease of 10° C. for the $T_{50}$ (Zhang S et al., 2000. *Eur. J. Biochem.* 267: 3101-15), or a slight increase of about 2° C. for the $T_{50}$ (Ai, Y. C. and Wilson, D. B. 2002. Enzyme Microb. Technol. 30:804-808). Wohlfahrt (Wohlfahrt, G., et al. 2003. *Biochemistry.* 42:10095-10103) disclosed an increase in the thermostability of TrCel6A, at an alkaline pH range, by replacing carboxyl-carboxylate pairs into amide-carboxylate pairs. A single mutant, E107Q, and a triple mutant, E107Q/D170N/D366N, have an improved $T_m$ above pH 7 but a lower $T_m$ at pH 5, which is the optimal pH of the wild-type TrCel6A. These mutations are found in, or close to, the N- and C-terminal loops. Hughes et al (Hughes, S. R., et al. 2006. *Proteome Sci.* 4:10-23) disclose a directed evolution strategy to screen mutagenized clones of the *Orpinomyces* PC-2 cellulase F (OPC2Cel6F) with targeted variations in the last four codons for improved activity at lower pH, and identified two mutants having improved activity at lower pH and improved thermostability.

The above reports describing rational design of Family 6 cellulases suggest that the introduction of hydrogen or disulfide bonds into the C-terminal loops is not a good strategy to increase the thermostability at optimal hydrolysis conditions. Furthermore, stabilizing the exo-loop of the *T. reesei* Family 7 cellobiohydrolase Cel7A, which forms the roof of the active site tunnel, by introducing a disulfide bond with mutation D241C/D249C showed no improvement in thermostability (von Ossowski I., et al. 2003. *J. Mol. Biol.* 333:817-829).

TrCel6A variants with improved thermostability are described in US Patent Publication No. 20060205042. Mutations were identified based alignment of TrCel6A amino acid sequence with those of eight Family 6 members using structural information and a modeling program. This alignment served as basis for the determination of a so-called consensus sequence. Those mutations that, according to the 3D-structure model of TrCel6A, fit into the structure without disturbance and were likely to improve the thermostability of the enzyme were selected as replacement for improved thermostability of TrCel6A. Among those identified as improving the thermostability of TrCel6A was the mutation of the serine at position 413 to a tyrosin (S413Y). This mutation increased the retention of enzymatic activity after a 1 hour pre-incubation at 61° C. from 20-23% for the parental TrCel6A to 39-43% for TrCel6A-S413Y; however, after a 1 hour pre-incubation at 65° C., the parent TrCel6A retained 5-9% of its activity while TrCel6A-S413Y retained 6-8% of its activity. The melting temperature, or Tm, improved by 0.2-0.3° C., from 66.5° C. for the parental TrCel6A to 66.7-66.8° C. for TrCel6A-S413Y.

Despite knowledge of the mechanisms of and desirable attributes for cellulases in the above and related industrial applications, the development of thermostable cellulases with improved stability, catalytic properties, or both improved stability and catalytic properties, would be advantageous. Although thermophilic and thermostable enzymes may be found in nature, the difficulty in achieving cost-effective large-scale production of these enzymes has limited their penetration into markets for industrial use. Therefore, a need exists for improved stable cellulases which can be economically produced at a high-level of expression by industrial micro-organisms such as *T. reesei*.

SUMMARY OF THE INVENTION

The present invention relates to modified Family 6 cellulases. More specifically, the invention relates to modified Family 6 cellulases that exhibit enhanced thermostability, alkalophilicity and/or thermophilicity. The present invention also relates to genetic constructs comprising nucleotide sequences encoding for modified Family 6 cellulases, methods for the production of the modified Family 6 cellulase from host strains and the use of the modified Family 6 cellulases in the hydrolysis of cellulose.

It is an object of the invention to provide an improved cellulase with increased thermostability, thermophilicity and alklophilicity.

This invention relates to a modified Family 6 cellulase produced by substitution of an amino acid at position 413 with a proline. The position(s) of the amino acid substitution(s) are determined from sequence alignment of the modified cellulase with a *Trichoderma reesei* Cel6A amino acid sequence as defined in SEQ ID NO: 1. The modified Family 6 cellulase exhibits enhanced thermostability, alkalophilicity, thermophilicity, or a combination thereof, relative to a parent Family 6 cellulase from which the Family 6 cellulase is derived.

The modified Family 6 cellulase may be derived from a filamentous fungus, such as *Trichoderma reesei*. In one embodiment of the invention, the modified cellulase is not derived from a cellulase which has a naturally-occurring proline residue at position 413 (TrCel6A numbering), for example a native Family 6 cellulase (CelF from *Orpinomyces* sp PC-2) which contains a proline residue at position 413.

This invention also includes a modified Family 6 cellulase comprising a proline residue at position 413 and further comprising polar amino acids at positions selected from 231, 305, 410 or a combination thereof.

The present invention also pertains to the modified Family 6 cellulase comprising a proline at position 413 and further comprising a substituted amino acid at position 231 selected from the group consisting of Ser, or Thr. The substituted amino acid at position 231 may be Ser.

The present invention also pertains to the modified Family 6 cellulase comprising a proline at position 413 and further comprising a substituted amino acid at position 305 selected from the group consisting of Ser and Thr.

The present invention also pertains to the modified Family 6 cellulase comprising a proline residue at position 413 and further comprising a substituted amino acid at position 410 selected from the group consisting of Gln and Asn.

The present invention also includes a Family 6 cellulase comprising a proline residue at position 413 and further comprising substituted amino acids at positions 231 and 305 with Ser residues (i.e. 231S, 305S), and substitution of an amino acid at position 410 with Gln. The modified Family 6 cellulase comprising these mutations may be from a filamentous fungus, such as *Trichoderma reesei*.

The present invention also relates to a modified Family 6 cellulase comprising a proline residue a position 413 and having an increase in thermostability relative to a parent cellulase, as measured by the "$T_{50}$", from about 5° C. to about 30° C. higher, or from about 9° C. to about 20° C. higher than the corresponding parent cellulase.

The present invention also relates to a modified Family 6 cellulase comprising a proline residue at position 413 and having an increase in its temperature for maximal activity ($T_{opt}$) of from about 1.5° C. to about 30° C. higher, or from about or 2.5° C. to about 20° C. higher, that the $T_{opt}$ of a parent Family 6 celulase. The present invention also relates to a modified Family 6 cellulase comprising a proline residue at position 413 and having an increase in its pH for maximal activity ($pH_{opt}$) of about 0.5 units to about 6.0 units higher, relative to a parent cellulase.

The present invention also relates to a modified Family 6 cellulase selected from the group consisting of:

TrCel6A-S413P;    (SEQ ID NO: 12)

TrCel6A-G82E-G231S-N305S-R410Q-S413P;    (SEQ ID NO: 13)

-continued

TrCel6A-G231S-S413P; (SEQ ID NO: 14)

TrCel6A-N305S-S413P; (SEQ ID NO: 15)

TrCel6A-R410Q-S413P; (SEQ ID NO: 16)

TrCel6A-G231S-N305S-S413P; (SEQ ID NO: 17)

TrCel6A-G231S-R410Q-S413P; (SEQ ID NO: 18)

TrCel6A-N305S-R410Q-S413P; (SEQ ID NO: 19)

TrCel6A-G231S-N305S-R410Q-S413P; (SEQ ID NO: 20)

HiCel6A-Y420P; and (SEQ ID NO: 21)

PcCel6A-S407P. (SEQ ID NO: 22)

The invention also relates to genetic constructs for directing expression and secretion of the modified Family 6 cellulase from a host microbe including, but not limited to, strains of *Trichoderma reesei*.

The present invention relates to a genetic construct comprising a DNA sequence encoding a modified Family 6 cellulase comprising a proline residue at position 413, which DNA sequence is operably linked to DNA sequences regulating its expression and secretion from a host microbe. Preferably, the DNA sequences regulating the expression and secretion of the modified Family 6 cellulase are derived from the host microbe used for expression of the modified cellulase. The host microbe may be a yeast, such as *Saccharomyces cerevisiae*, or a filamentous fungus, such as *Trichoderma reesei*.

The invention also relates to a genetic construct comprising a DNA sequence encoding a modified Family 6 cellulase comprising a proline residue at position 413 and further comprising substituted amino acids at positions 231 and 305 with Ser and substitution of an amino acid at position 410 with Gln. The DNA sequence is operably linked to DNA sequences regulating its expression and secretion from a host microbe. Preferably, the DNA sequences regulating the expression and secretion of the modified Family 6 cellulase are derived from a filamentous fungus, including, but not limited to, *Trichoderma reesei*.

The invention also relates to a genetically modified microbe capable of expression and secretion of a modified Family 6 cellulase comprising a proline residue at position 413 and comprising a genetic construct encoding the modified Family 6 cellulase. In one embodiment, the modified Family 6 cellulase further comprises Ser residues at positions 231 and 305 and a Gln residue at position 410. Preferably, the genetically modified microbe is a yeast or filamentous fungus. The genetically modified microbe may be a species of *Saccharomyces, Pichia, Hansenula, Trichoderma, Aspergillus, Fusarium, Humicola, Neurospora* or *Phanerochaete*.

The present invention also relates to the use of a modified Family 6 cellulase comprising a proline residue at position 413 for treatment of a cellulosic substrate.

The invention also relates to the process of producing the modified Family 6 cellulase, including transformation of a yeast or fungal host, selection of recombinant yeast or fungal strains expressing the modified Family 6 cellulase, and culturing the selected recombinant strains in submerged liquid fermentations under conditions that induce the expression of the modified Family 6 cellulase.

Family 6 cellulases of the present invention comprising a proline residue at position 413 display improved thermostability and thermophilicity or alkalophilicity relative to wild-type Family 6 cellulases. Without wishing to be bound by theory, improved thermostability of the modified Family 6 cellulase results from amino acid substitutions that stabilize the C-terminal loop of Family 6 cellobiohydrolases by increasing the stability of the small $\alpha$-helix.

Such cellulases find use in a variety of applications in industry that require enzyme stability and activities at temperatures and/or pH values above that of the native enzyme. For example, modified Family 6 cellulases, as described herein, may be used for the purposes of saccharification of lignocellulosic feedstocks for the production of fermentable sugars and fuel alcohol, improving the digestibility of feeds in ruminant and non-ruminant animals, pulp and paper processing, releasing dye from and softening denim.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows an amino acid sequence alignment among Family 6 cellulases. The amino acid numbering for each cellulase is compared with that of the *Trichoderma reesei* Cel6A (TrCel6A; SEQ ID NO:1) as indicated at the left and right of each sequences. The residues at positions 213, 305, 410 and 413 (relative to TrCel6A) are indicated with an asterisk. The residues identical with the corresponding amino acid in TrCel6A are in bold. For cellulases with a cellulose-binding domain, only the catalytic core sequences are presented. CfCel6B (SEQ ID NO:2); HiCel6A (SEQ ID NO:4); HiCel6B (SEQ ID NO:11); MtCel6A (SEQ ID NO:9); NpCel6A (SEQ ID NO:5); OpC2Cel6F (SEQ ID NO:6); PE2Cel6A (SEQ ID NO:8); TfCel6A (SEQ ID NO:10); TfCel6B (SEQ ID NO:3).

DESCRIPTION OF PREFERRED EMBODIMENT

Figure 2:
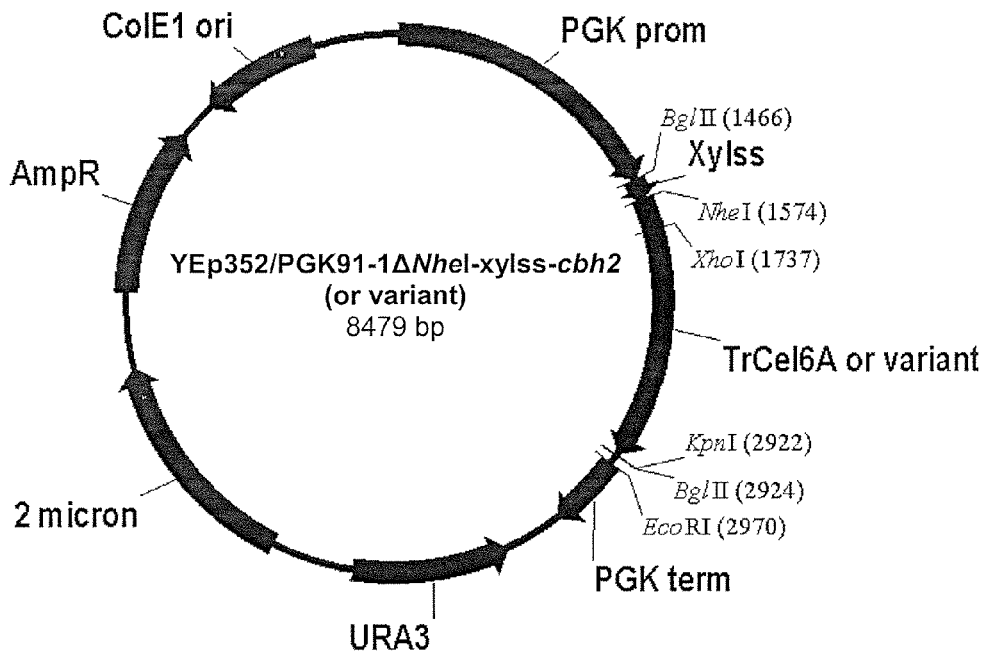
FIG. 2 depicts plasmid vectors a) YEp352/PGK91-1ΔN-heI-xyl$_{SS}$-cbh2 vector, b) YEpFLAGΔKpn10-cbh2 directing the expression and secretion of native and modified TrCel6A from recombinant *Saccharomyces cerevisiae* (The same organization if found for the TrCel6 variants cloned in the same vectors), c) YEpFLAGΔKpn10-PcCel6A directing the expression and secretion of native and modified PcCel6A from recombinant *Saccharomyces cerevisiae* (The same organization if found for the PcCel6 variants cloned in the same vectors), d) YEpFLAGΔKpn10-HiCel6A directing the expression and secretion of native and modified HiCel6A from recombinant *Saccharomyces cerevisiae* (The same organization if found for the HiCel6 variants cloned in the same vectors).
Figure 2:
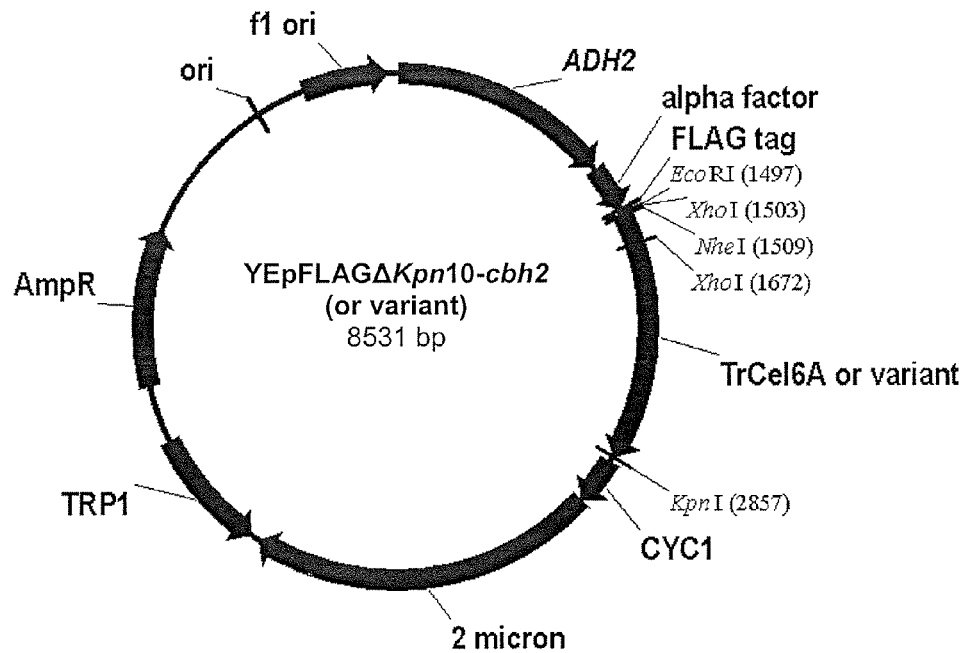
Figure 2:
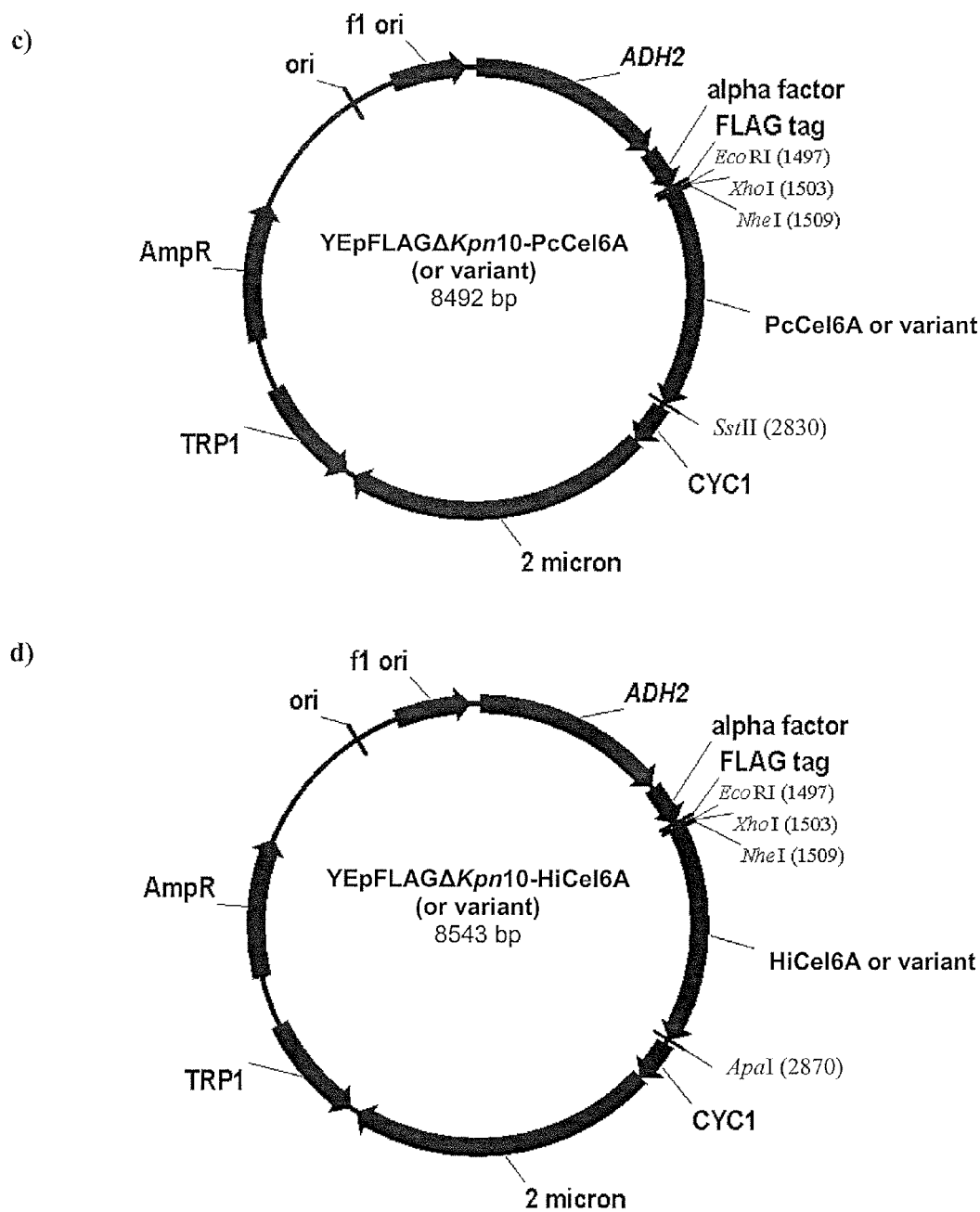
Figure 3:
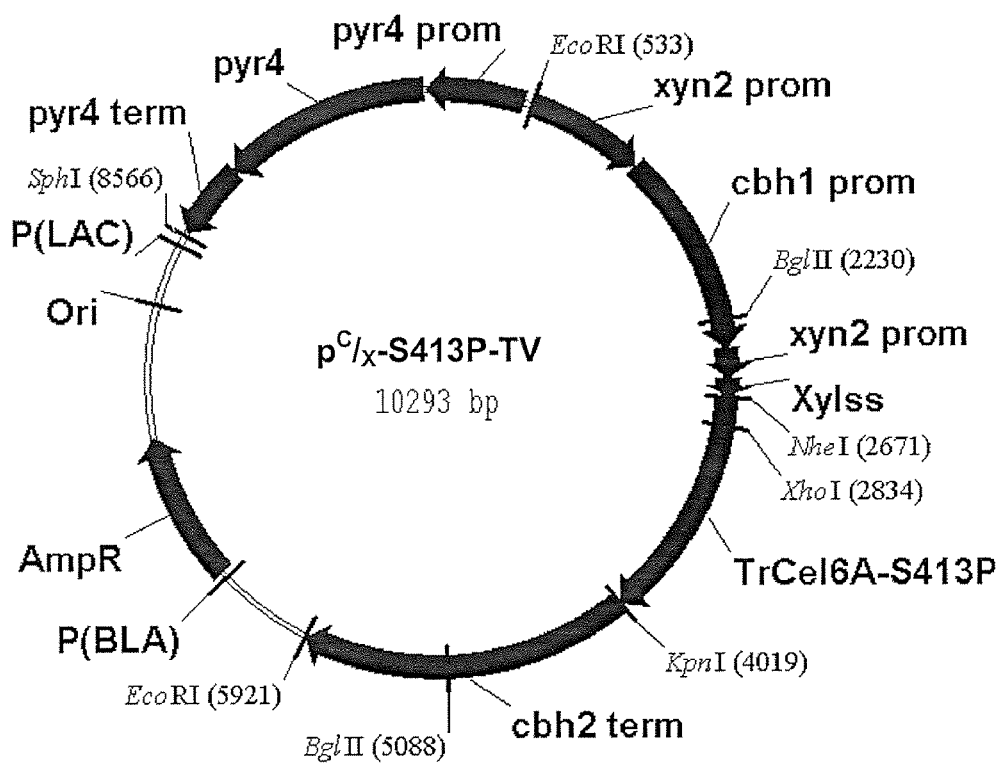
FIG. 3 depicts the vector pC/X—S413P-TV used to transform and direct the expression and secretion of modified TrCel6A from recombinant *Trichoderma reesei*. As shown, the TrCel6A-S413P gene is operable linked to the promoter of the cbh1 (TrCel7A) gene, the secretion signal peptide of the xln2 (TrXyl11B) genes and the transcriptional terminator of the native cbh2 (TrCel6A) gene. The selection marker is the *Neurospora crassa* pyr4 gene.

The present invention relates to modified cellulase. More specifically, the invention relates to modified Family 6 cellulases with enhanced thermostability, alkalophilicity and/or thermophilicity. The present invention also relates to genetic constructs comprising nucleotide sequences encoding for modified Family 6 cellulases, methods for the production of the modified Family 6 cellulase from host strains and the use of the modified Family 6 cellulases in the hydrolysis of cellulose.

The following description is of a preferred embodiment by way of example only and without limitation to the combination of features necessary for carrying the invention into effect.

Modified Family 6 Cellulases

Figure 1:
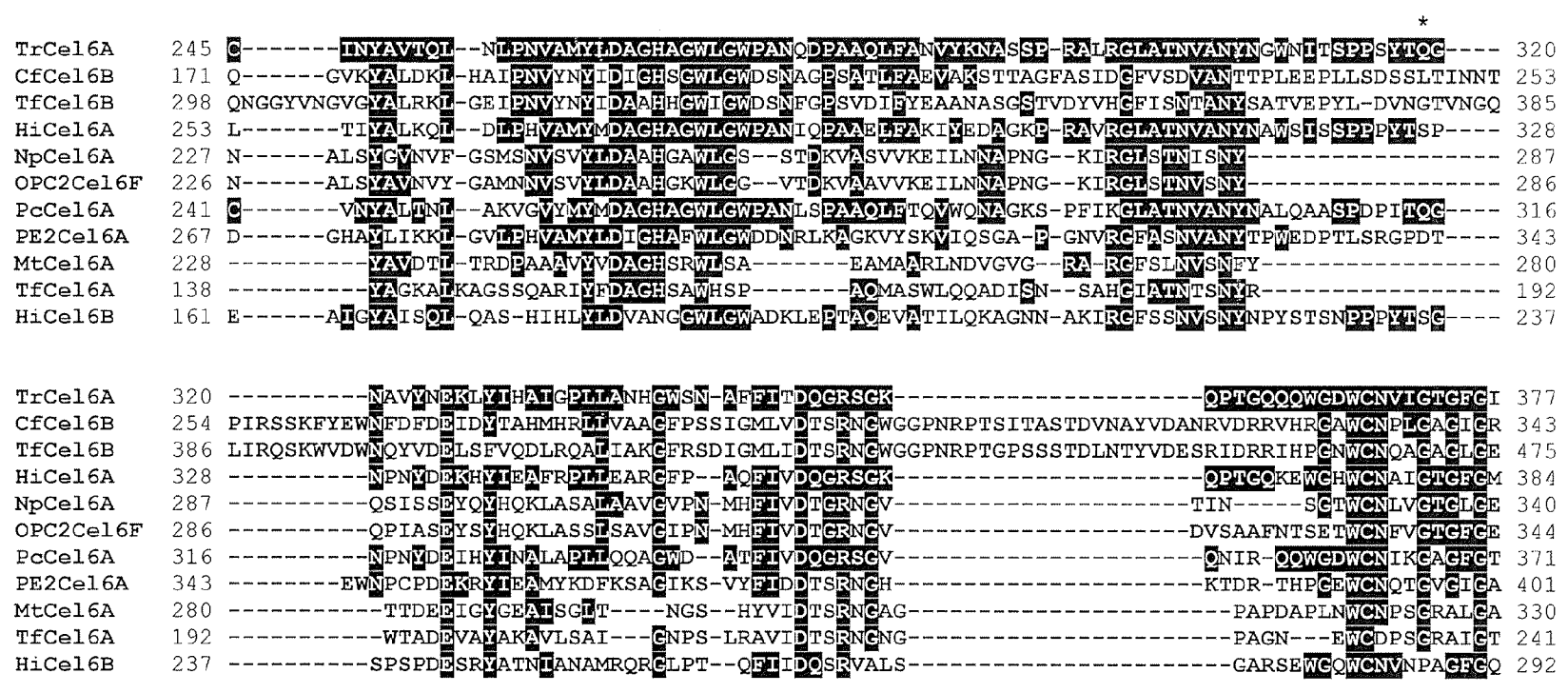
Figure 1:
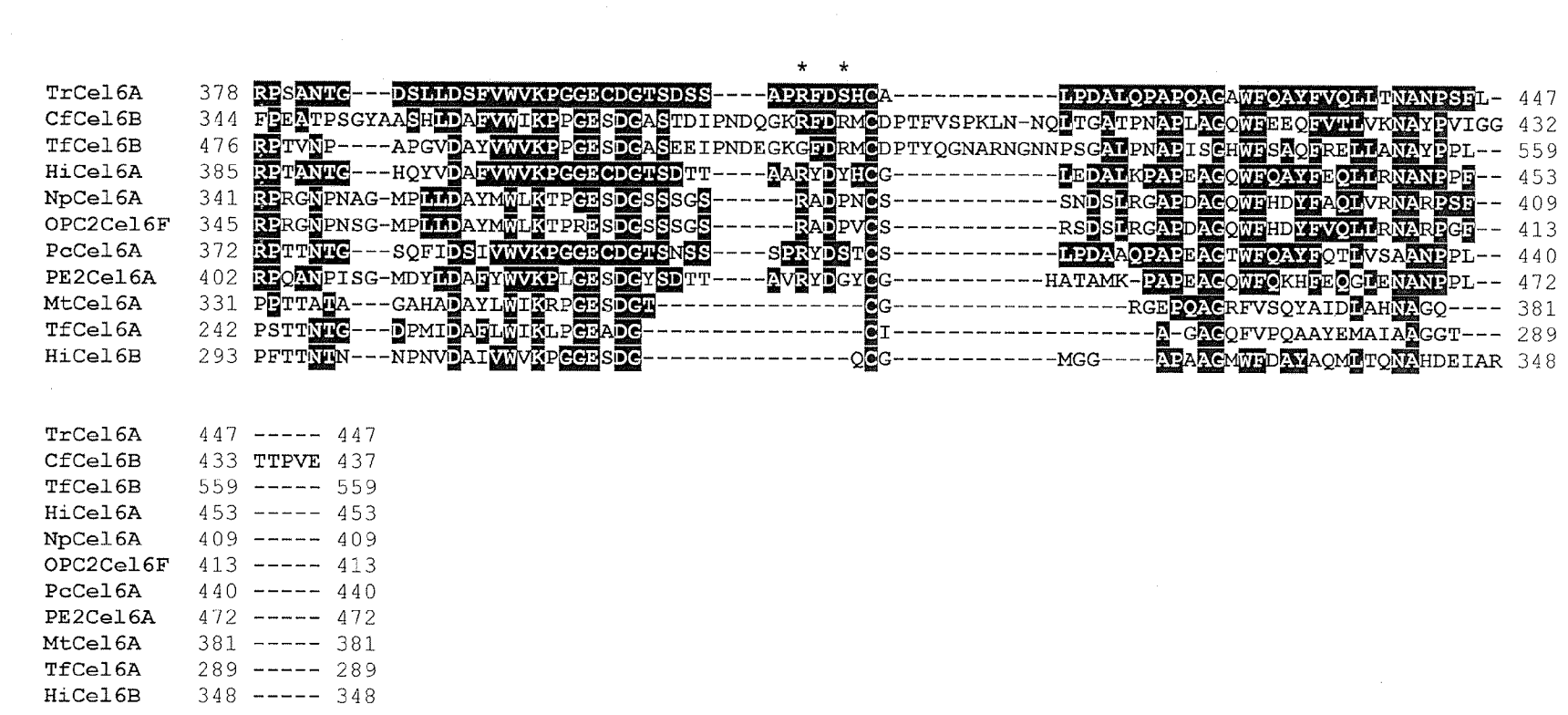

Family 6 (previously, Family B) cellulases enzymes are a group of enzymes that hydrolyse the β-1,4 glucosidic linkages in cellulose with inversion of configuration of the anomeric carbon (Claeyssens, M. and Henrissat, B. 1992, Protein Science 1: 1293-1297). Family 6 cellulases share extensive amino acid sequence similarity (FIG. 1). A cellulase is classified as a Family 6 cellulase if it comprises amino acids common to other Family 6 cellulase, including two aspartic acid (D) residues which may serve as catalytic residues. These aspartic acid residues are found at positions 175 and 221 (see FIG. 1; based on TrCel6A (*Trichoderma reesei* Cel6A enzyme) amino acid numbering). Most of the Family 6 cellulases identified thus far are mesophilic. However, this family also includes thermostable cellulases from *Thermobifida fusca* (TfCel6A and TfCel6B) and the alkalophilic cellulases from *Humicola insolens* (HiCel6A and HiCel6B).

The topology of Family 6 catalytic domains is a variant of the α/β-barrel with a central β-barrel containing seven parallel β-strands connected by five α-helices. One important difference between Family 6 cellobiohydrolases and endo-β-1,4-glucanases is the length of their N- and C-terminal loops present on each side of the active site and which are responsible for their functional behavior on cellulose. In the cellobiohydrolases, an extensive C-terminal loop forms a tunnel with the N-terminal loop enclosing the active site. This confers the unique property of cellobiohydrolases to attack the ends of crystalline cellulose where the N- and C-terminal loops maintain a single cellulose chain in the active site and facilitate the processive degradation of the substrate. In the endo-β-1,4-glucanases, the C-terminal loop is reduced in length and the N-terminal loop pulls it away from the active site and could be also shorter resulting in a more open active site allowing access to internal β-1,4 glycosidic bonds of cellulose for hydrolysis. The role of these loops in the functional behavior of Family 6 enzymes on cellulose was confirmed by the deletion of fifteen amino acids of the C-terminal loop of the *Cellulomonas fimi* cellobiohydrolase Cel6B in order to mimic the properties of an endo-β-1,4-glucanase (Meinke A., et al. 1995. *J. Biol. Chem.* 270:4383-4386). The mutation enhanced the endo-β-1,4-glucanase activity of the enzyme on soluble cellulose, such as carboxymethylcellulose, and altered its cellobiohydrolase activity on insoluble cellulose.

Non-limiting examples of Family 6 cellulases that may be modified following the general approach and methodology as outlined herein are described in Table 1 below.

TABLE 1

Family 6 cellulase enzymes

| Microbe | Cellulase | SEQ ID No. |
|---|---|---|
| *Cellulomonia fimi* | CfCe16B | 2 |
| *Humicola insolens* | HiCe16A | 4 |
| *Humicola insolens* | HiCe16B | 11 |
| *Mycobacteriumn tuberculosis* | MtCe16A | 9 |
| *Neocallimatrix patriciarum* | NpCe16A | 5 |

TABLE 1-continued

Family 6 cellulase enzymes

| Microbe | Cellulase | SEQ ID No. |
|---|---|---|
| Orpinomyces sp. PC-2 | OpC2Cel6F | 6 |
| Phanerochaete chrysosporium | PcCel6A | 7 |
| Pyromyces sp. E2 | PE2Cel6A | 8 |
| Thermobifida fusca | TfCel6A | 10 |
| Thermobifida fusca | TfCel6B | 3 |

Examples of preferred Family 6 cellulases, which are not meant to be limiting, include *Trichoderma reesei* Cel6A, *Humicola insolens* Cel6A, *Phanerochaete chrysosporium* Cel6A, *Cellulomonas fimi* Cel6B, *Thermobifida fusca* Cel6B. More preferably, the modified cellulase of the present invention comprises a modified *Trichoderma reesei* Cel6A enzyme.

By "modified Family 6 cellulase" or "modified cellulase", it is meant a Family 6 cellulase in which the amino acid at position 413 (said position determined from sequence alignment of said modified cellulase with a *Trichoderma reesei* Cel6A amino acid sequence as defined in SEQ ID NO:1) has been altered, using techniques that are known to one of skill in the art, to a proline and which exhibits improvements in thermostability, thermophilicity, alkalophilicity, or a combination thereof, over the corresponding unmodified Family 6 cellulase. Techniques for altering amino acid sequences include, but are not limited to, site-directed mutagenesis, cassette mutagenesis, random mutagenesis, synthetic oligonucleotide construction, cloning and other genetic engineering techniques (Eijsink V G, et al. 2005. *Biomol. Eng.* 22:21-30, which is incorporated here in by reference). It will be understood that the modified cellulase may be derived from any Family 6 cellulase. The modified cellulase may be derived from a wild-type cellulase or from a cellulase that already contains other amino acid substitutions.

For the purposes of the present invention, the parent cellulase is a cellulase that does not contain a substitution of its original amino acid at position 413 (said position determined from sequence alignment of said modified cellulase with a *Trichoderma reesei* Cel6A amino acid sequence as defined in SEQ ID NO:1) by a proline and is otherwise identical to the modified cellulase. As such, the parent cellulase may be a cellulase that contains amino acid substitutions at other positions that have been introduced by genetic engineering or other techniques. However, a parent cellulase does not include those cellulases in which the naturally occurring amino acid at position 413 is a proline.

By "TrCel6A numbering", it is meant the numbering corresponding to the position of amino acids based on the amino acid sequence of TrCel6A (Table 1; FIG. 1; SEQ ID NO:1). As disclosed below, and as is evident by FIG. 1, Family 6 cellulases exhibit a substantial degree of sequence similarity. Therefore, by aligning the amino acids to optimize the sequence similarity between cellulase enzymes, and by using the amino acid numbering of TrCel6A as the basis for numbering, the positions of amino acids within other cellulase enzymes can be determined relative to TrCel6A.

Enzyme thermostability can be defined by its melting temperature ($T_m$), the half-life ($t_{1/2}$) at defined temperature, and the temperature at which 50% of the initial enzyme activity is lost after incubation at defined time ($T_{50}$). Thermophilic enzymes typically show common structural elements that have been identified as contributing factors to enzyme thermostability when compared to their mesophilic counterparts (e.g. see Sadeghi M., et al. 2006. *Biophys. Chem.* 119:256-270). These structural elements include greater hydrophobicity, better packing, increased polar surface area, deletion or shortening of loops, interactions, smaller and less numerous cavities, stability of α-helix, increase in aromatic interactions, additional disulfide bridges or metal binding and glycosylation sites, decreased glycines and enhanced prolines content, increased hydrogen bonding and salt bridges, improved electrostatic interactions, decreased of thermolabile residues, and conformational strain release.

For the purposes of the present invention, a cellulase exhibits improved thermostability with respect to a corresponding parent cellulase if it has a $T_{50}$ which is at least about 4° C., or at least about 9° C. higher than that of the parent cellulase, or for example a cellulase having a $T_{50}$ from about 4° C. to about 30° C. higher, or any amount therebetween, or a $T_{50}$ from about 9° C. to about 30° C. higher, or any amount therebetween, when compared to that of the parent cellulase. The $T_{50}$ is the temperature at which the modified or the natural enzyme retains 50% of its residual activity after a pre-incubation for 15 minutes and is determined by the assay detailed in Example 10.4. As set forth in Example 10.4, the residual activity against β-glucan in a 30 minute assay at 65° C. is normalized to 100%.

The modified Family 6 cellulase may have Tso which is about 4° C. to about 30° C. higher than that of a corresponding parent cellulase, or any range therebetween, about 5° C. to about 20° C. higher, or any range therebetween, about 8° C. to about 15° C. higher, or any range therebetween, or from about 9° C. to about 15° C. higher, or any range therebetween. For example, the modified cellulase may have a $T_{50}$ that is at least about 4, 5, 6, 7, 8, 9, 10, 12, 14, 16, 18, 20, 22, 24, 26, 28, or 30° C. higher than that of the corresponding parent cellulase.

The modified Family 6 cellulase may also be characterized as having a $T_{50}$ above 65° C. (or at least 5° C. above that of the corresponding parent Family 6 cellulase), for example, the modified cellulase may have a $T_{50}$ from about 65° C. to about 90° C., or any amount therebetween. The modified Family 6 cellulase may have a $T_{50}$ above 70° C. (or at least 9° C. above the parent Family 6 cellulase) for example, the modified cellulase may have a $T_{50}$ so from about 70° C. to about 90° C., or any amount therebetween. The Family 6 cellulase may have a $T_{50}$ of 50, 55, 60, 65, 70, 75, 80, 85 or 90° C. or any amount therebetween.

For the purposes of this specification, a cellulase exhibits improved thermophilicity with respect to a corresponding parent cellulase if the cellulase exhibits a temperature optimum ($T_{opt}$) that is at least about 1.5° C. higher than the $T_{opt}$ of the corresponding parent cellulase. For example, a cellulase exhibits improved thermophilicity if the cellulase exhibits a temperature optimum ($T_{opt}$) that is from about 1.5° C. to about 30° C. or any amount therebetween, higher than the $T_{opt}$ of the corresponding parent cellulase By temperature optimum or $T_{opt}$, it is meant the highest temperature at which a cellulase exhibits its maximal activity. For the purposes of this specification, the $T_{opt}$ of a Family 6 cellulase is determined by measuring the temperature profile of activity against a β-glucan substrate as detailed in Example 10.1. The temperature profile for the activity of the cellulase is measured at its pH optimum.

The modified Family 6 cellulase may have a $T_{opt}$ which is at least about 1.5° C. to about 30° C. higher than the $T_{opt}$ of a corresponding parent Family 6 cellulase. In a preferred embodiment, the $T_{opt}$ of the modified Family 6 cellulase is at least about 2.5° C. to about 20° C. higher than the $T_{opt}$ of parent Family 6 cellulase. For example, the modified Family 6 cellulase may have a $T_{opt}$ of at least about 1.5, 2.5, 4.0, 5.0, 6.0, 8.0, 10.0, 12.0, 15.0, 20.0, 25.0, or 30° C. higher than that of the corresponding parent cellulase.

The terms "thermostability" and "thermophilicity" have been used interchangeably within the literature. However, the use of the terms as defined herein is consistent with the usage of the terms in the art (Mathrani, I and Ahring, B. K. 1992 *Appl. Microbiol. Biotechnol.* 38:23-27).

For the purposes of the present invention, a cellulase exhibits improved alkalophilicity with respect to a corresponding parent cellulase if the cellulase exhibits a $pH_{opt}$ that is at least about 0.5 units higher than the $pH_{opt}$ of the parent cellulase. By $pH_{opt}$, it is meant the highest pH at which a cellulase exhibits its maximal activity. For the purpose of this specification, the $pH_{opt}$ is determined by measuring the pH profile of a Family 6 cellulase as set out in Example 10.2.

The modified Family 6 cellulase may have a $pH_{opt}$ that is at least about 0.5 units to about 6.0 units, or any amount therebetween, higher than the $pH_{opt}$ of the parent Family 6 cellulase. In a preferred embodiment, the $pH_{opt}$ of the modified Family 6 cellulase is at least about 0.8 units to about 5.0 units, or any amount therebetween, higher than the $pH_{opt}$ parent Family 6 cellulase. For example, the $pH_{opt}$ of the cellulase may be about 0.5, 1.0, 1.5, 2.0, 2.5, 3.0, 3.5, 4.0, 4.5, 5.0, 5.5 or 6.0 units higher than the $pH_{opt}$ of the parent cellulase.

As described in more detail herein, several mutant Family 6 cellulases have been prepared that exhibit enhanced thermostability, thermophilicity, alkalophilicity, or a combination thereof. A list of several mutants, which is not to be considered limiting in any manner, is presented in Table 2.

TABLE 2

Modified Family 6 cellulases

| New mutant TrCe16A | SEQ ID NO: |
|---|---|
| TrCe16A-S413P | 12 |
| TrCe16A-G82E-G231S-N305S-R410Q-S413P | 13 |
| TrCe16A-G231S-S413P | 14 |
| TrCe16A-N305S-S413P | 15 |
| TrCe16A-R410Q-S413P | 16 |
| TrCe16A-G231S-N305S-S413P | 17 |
| TrCe16A-G231S-R410Q-S413P | 18 |
| TrCe16A-N305S-R410Q-S413P | 19 |
| TrCe16A-G231S-N305S-R410Q-S413P | 20 |
| HiCe16A-Y420P | 21 |
| PcCe16A-S407P | 22 |

Genetic Constructs Comprising Modified Family 6 cellulases

The present invention also relates to genetic constructs comprising a DNA sequence encoding the modified Family 6 cellulase operably linked to regulatory DNA sequences directing the expression and secretion of the modified Family 6 cellulase from a host microbe. The regulatory sequences are preferably functional in a fungal host. The regulatory sequences may be derived from genes that are highly expressed and secreted in the host microbe under industrial fermentation conditions. In a preferred embodiment, the regulatory sequences are derived from any one or more of the *Trichoderma reesei* cellulase or hemicellulase genes.

The genetic construct may further comprise a selectable marker to enable isolation of a genetically modified microbe transformed with the construct as is commonly known with the art. The selectable marker may confer resistance to an antibiotic or the ability to grow on medium lacking a specific nutrient to the host organism that otherwise could not grow under these conditions. The present invention is not limited by the choice of selection marker, and one of skill may readily determine an appropriate marker. In a preferred embodiment, the selection marker confers resistance to hygromycin, phleomycin, kanamycin, geneticin, or G418, complements a deficiency of the host microbe in one of the trp, arg, leu, pyr4, pyr2, ura3, ura5, his, or ade genes or confers the ability to grow on acetamide as a sole nitrogen source. In a more preferred embodiment, the selectable marker is the *Neurospora crassa* pyr4 gene encoding orotidine-5'-decarboxylase.

Genetically Modified Microbes Comprising Modified Family 6 cellulases

The modified Family 6 cellulase may be expressed and secreted from a genetically modified microbe produced by transformation of a host microbe with a genetic construct encoding the modified Family 6 cellulase. The host microbe is preferably a yeast or a filamentous fungi, including, but not limited to, a species of *Saccharomyces, Pichia, Hansenula, Trichoderma, Hypocrea, Aspergillus, Fusarium, Humicola, Neurospora* or *Phanerochaete*. Typically, the host microbe is one from which the gene(s) encoding any or all Family 6 cellulases have been deleted. In a most preferred embodiment, the host microbe is an industrial strain of *Trichoderma reesei*.

The genetic construct may be introduced into the host microbe by any number of methods known by one skilled in the art of microbial transformation, including but not limited to, treatment of cells with $CaCl_2$, electroporation, biolistic bombardment, PEG-mediated fusion of protoplasts (e.g. White et al., WO 2005/093072, which is incorporated herein by reference).

After selecting the recombinant fungal strains expressing the modified Family 6 cellulase, the selected recombinant strains may be cultured in submerged liquid fermentations under conditions that induce the expression of the modified Family 6 cellulase.

Hydrolysis of Cellulosic Substrates

The present invention also relates to the use of the modified Family 6 cellulases described herein for the hydrolysis of a cellulosic substrate. By the term "cellulosic substrate", it is meant any substrate derived from plant biomass and comprising cellulose, including, but not limited to, lignocellulosic feedstocks for the production of ethanol or other high value products, animal feeds, forestry waste products, such as pulp and wood chips, and textiles.

By the term "lignocellulosic feedstock", it is meant any type of plant biomass such as, but not limited to, non-woody plant biomass, cultivated crops such as, but not limited to, grasses, for example, but not limited to, C4 grasses, such as switch grass, cord grass, rye grass, miscanthus, reed canary grass, or a combination thereof, sugar processing residues, for example, but not limited to, baggase, beet pulp, or a combination thereof, agricultural residues, for example, but not limited to, soybean stover, corn stover, rice straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof.

In the saccharification of lignocellulosic feedstocks for the production of ethanol, or other products, cellulases of the invention may be used to hydrolyze a pretreated feedstock produced by, for example, but not limited to, steam explosion (see Foody, U.S. Pat. No. 4,461,648, which is incorporated herein by reference and to which the reader is directed for reference). Pretreatment may involve treatment of the feedstock with steam, acid, or typically a combination of steam and acid, such that the cellulose surface area is greatly increased as the fibrous feedstock is converted to a muddy texture, with little conversion of the cellulose to glucose. The cellulase enzymes of the invention then may be used to hydrolyze cellulose to glucose in a subsequent step. The glucose may then be converted to ethanol or other products.

Modified cellulase enzymes of the invention may be added to pulp or wood chips to enhance the bleaching or reduce refining energy of the pulp. The pulp may be produced by a chemical pulping process or by mechanical refining.

Increasing the Thermostability of Family 6 Cellulases

The thermostability of the mutant Family 6 cellulase was compared via pre-incubation of the enzyme in the absence of substrate at different temperatures. After 15 minutes, the residual activity of the cellulase was determined via a standard assay with soluble β-glucan as a substrate.

The effect of the S413P mutation, alone or in combination with one or more of G231S, N305S and R410Q, on the thermostability of Family 6 cellulase was determined via a comparative study of the modified TrCel6A-S413P and the parent TrCel6A. After pre-incubation at higher temperatures for up to 120 minutes, the former retained greater residual activity than the latter (FIG. 5a).

The pre-incubation temperature that allowed Family 6 cellulase to retain 50% of the residual activity, $T_{50}$, was determined. For the modified Family 6 cellulase, TrCel6A-S413P, the $T_{50}$ was 64.1° C., as compared to 59° C. for the parent TrCel6A (FIG. 4a). This represented an increase in the thermostability by over 5° C. through the introduction of the S413P mutation.

The $T_{50}$ of the other TrCel6A variants was at least 3.2° C. higher then wild-type TrCel6A. PcCel6A-S407P and HiCel6A-Y420P also have shown an increase in $T_{50}$ when compared to their respective parent enzyme (FIGS. 4b and c).

Increasing the Thermophilicity of Family 6 Cellulases

The thermophilicity of the modified Family 6 cellulases was determined by measuring effect of the assay temperature on the hydrolysis of β-glucan.

Figure 6:
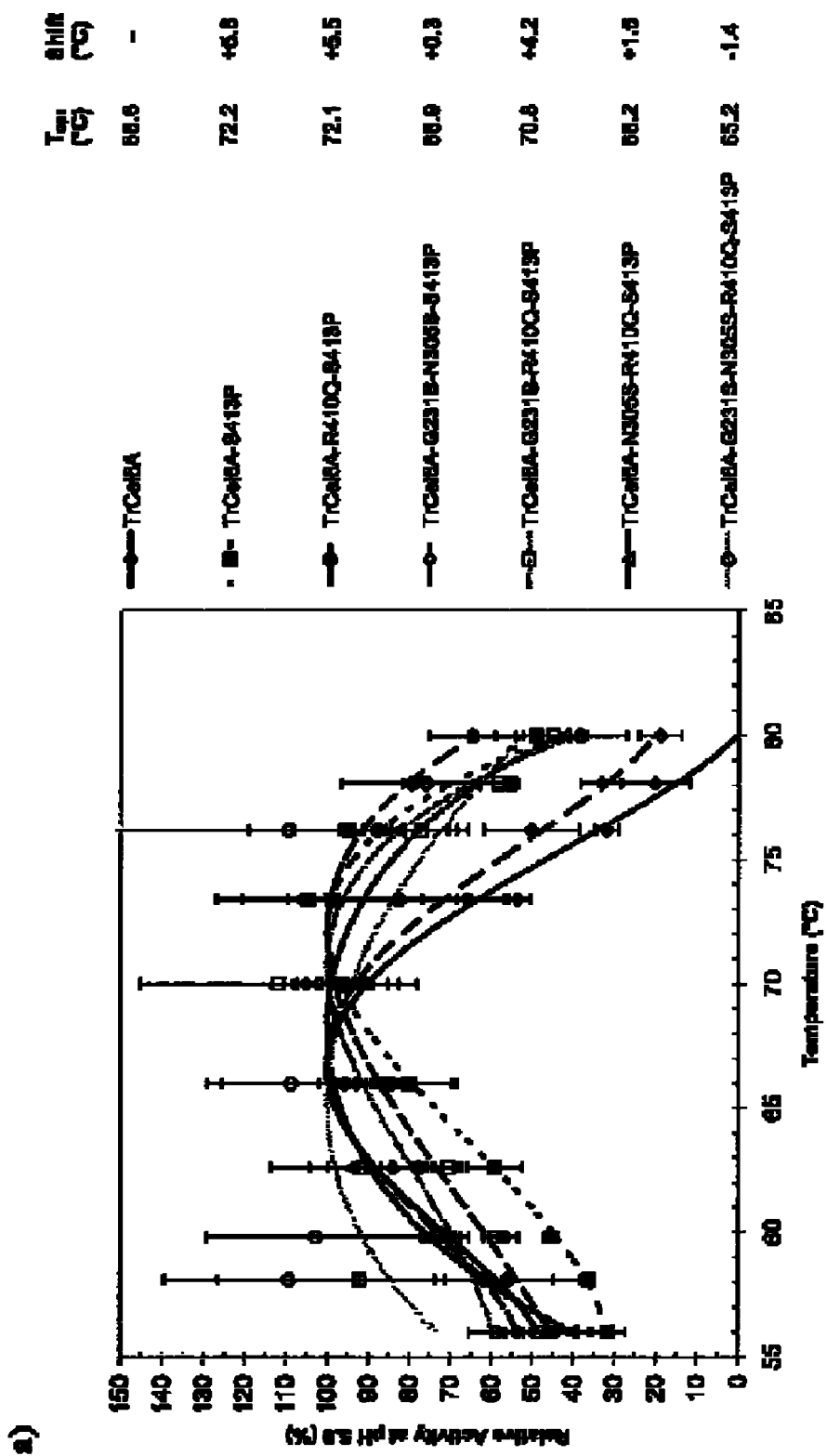
FIG. 6 shows the effect of temperature on the enzymatic activity of a) the native TrCel6A and modified Family 6 cellulases TrCel6A-S413P, TrCel6A-G82E-G231S-N305S-R410Q-S413P, TrCel6A-R410Q-S413P, TrCel6A-G231S-N305S-S413P, TrCel6A-G231S-R410Q-S413P, TrCel6A-N305S-R410Q-S413P and TrCel6A-G231S-N305S-R410Q-S413P b) the native PcCel6A and modified Family 6 cellulases PcCel6A-S407P and c) the native HiCel6A and modified Family 6 cellulases HiCel6A-Y420P during 30 minutes incubation at pH 5.0. The data are normalized to the activity observed at the temperature optimum for each enzyme.
Figure 6:
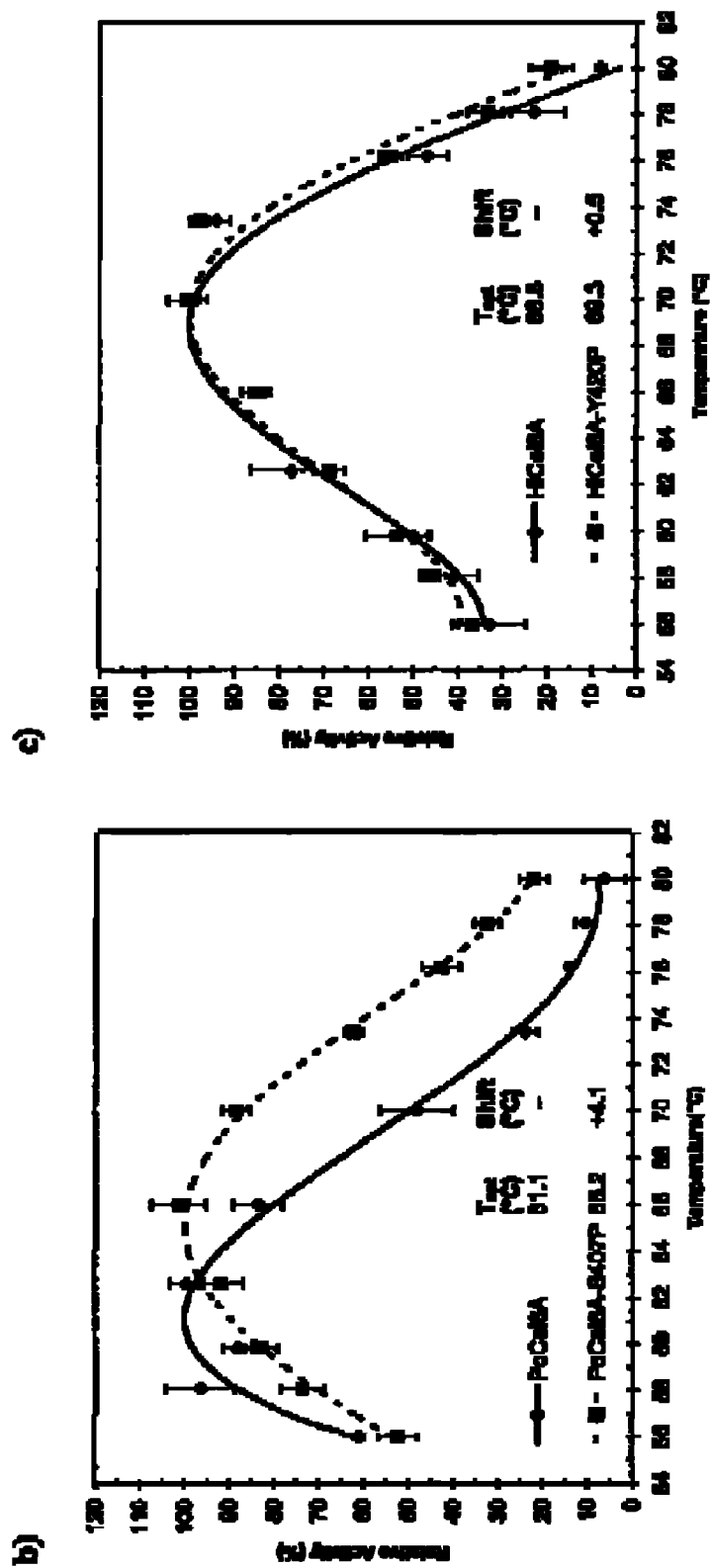

All modified Family 6 cellulases shown an improved $T_{opt}$ for β-glucan hydrolysis when compared to their respective wild-type except variant TrCel6A-G231S-N305S-R410Q-S413P which on the other hand exhibits a broad temperature range with more then 80% of the maximum activity (FIG. 6). Among all TrCel6A variants, TrCel6A-S413P has the higher optimal temperature at 72.2° C., an increase of 5.6° C. in thermophilicity compared to wild-type TrCel6A (FIG. 6a). PcCel6A-S407P and HiCel6A-Y420P also exhibit an increase in optimal temperature when compared to their respective wild-type (FIGS. 6b and c).

Increasing the Alkalophilicity of Family 6 Cellulases

The effect of the S413P mutation, alone or in combination with one or more of G231S, N305S and R410Q, on the pH/activity profile of Family 6 cellulase was also studied.

All modified Family 6 cellulases exhibit increased alkalophilicity when compared to their wild-type. For TrCel6A, the most important shift was observed with variants TrCel6A-G231S-R410Q-S413P (+1.25 pH units) followed by TrCel6A-G231S-N305S-R410Q-S413P (+1.01 pH units).

Figure 8:
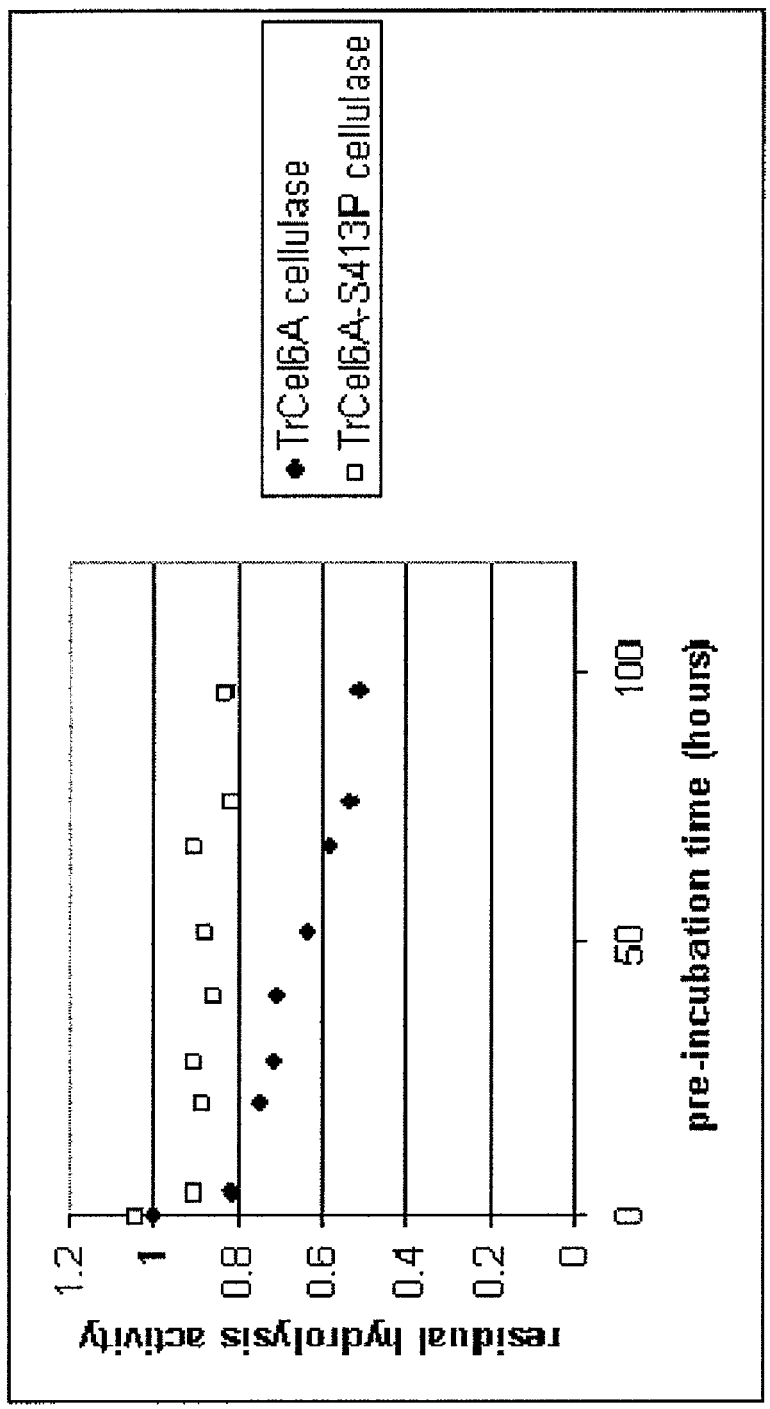
FIG. 8 shows the relative activity of whole *Trichoderma* cellulases comprising TrCel6A or TrCel6A-S413P (along with all of the remaining native *Trichoderma reesei* cellulase components) in the enzymatic hydrolysis of pretreated lignocellulosic substrate after 0, 4, 20.5, 28, 40.5, 52, 68, 76 and 96 hours of pre-incubation in the absence of substrate at 50° C. in 50 mM citrate buffer, pH 5.0.

Cellulase systems comprising modified Family 6 cellulases in combination with non-Family 6 cellulases show improved thermostability. A *Trichoderma* cellulase system comprising TrCel6A-S413P maintains at least 80% of its maximal activity after incubation in the absence of substrate at 50° C. for 96 hours, while the corresponding cellulase system comprising the parent TrCel6A maintains only 50% of its maximal activity (FIG. 8).

In summary, improved thermostable, alkalophilic and/or thermophlic mutant Family 6 cellulase of the invention comprise a proline residue at position 413 and may further comprise one or more than one of the following amino acid substitutions:

(i) a substituted amino acid at position 231 such as a polar amino acid, including, but not limited to, Ser;
(ii) a substituted amino acid at position 305, such as a polar amino acid, including, but not limited to, Ser;
(iii) a substituted amino acid at position 410, such as a polar amino acid, including, but not limited to, Gln; and
(iv) combinations of any of the above mutations set out in (i) to (iii).

Non-limiting examples of preferred Family 6 cellulase mutants comprising a S413P in combination with the amino acid substitutions listed above are given in Table 2.

Furthermore, the modified Family 6 cellulase of the present invention may comprise amino acid substitutions not listed above in combination with S413P.

The above description is not intended to limit the claimed invention in any manner. Furthermore, the discussed combination of features might not be absolutely necessary for the inventive solution.

EXAMPLES

The present invention will be further illustrated in the following examples. However, it is to be understood that these examples are for illustrative purposes only and should not be used to limit the scope of the present invention in any manner.

Examples

Example 1 describes the strains and vectors used in the following examples. Examples 2-5 describe the random mutagenesis of the TrCel6A gene, cloning of the random mutagenesis libraries in yeast vectors and high-throughput screening to identify modified Family 6 cellulases with increased thermostability. Examples 6-8 describe the cloning, recombination and expression of the modified and native Family 6 cellulase genes in an alternative yeast vector for higher expression. Example 9 describes the enzymatic characterization of modified Family 6 cellulases. Example 10 describes genetic constructs to express and secrete the modified Family 6 cellulases in a filamentous fungus. Example 11 describes the transformation of fungal protoplasts with genetic constructs expressing modified Family 6 cellulases. Example 12 describes the production of modified Family 6 cellulases from modified microbes in submerged liquid cultures. Example 13 describes the characterization of whole *Trichoderma* cellulases comprising modified Family 6 cellulases in combination with cellulases from other Families.

Example 1

Strains and Vectors

Saccharomyces cerevisiae strain DBY747 (his3-Δ1 leu2-3 leu2-112 ura3-52 trp1-289 (amber mutation) gal(s) CUP(r)) was obtained from the ATCC. S. cerevisiae strain BJ3505 (pep4::HIS3 prb-Δ10.6R HIS3 lys2-208 trp1-Δ101 ura3-52 gal2 can1) was obtained from Sigma and was a part of the Amino-Terminal Yeast FLAG Expression Kit.

A strain of Trichoderma reesei obtained derived from RutC30 (ATCC #56765; Montenecourt, B. and Eveleigh D. 1979. Adv. Chem. Ser. 181: 289-301) comprising a disrupted native TrCel6A gene was used in the experiments described herein.

Escherichia coli strains HB101 (F⁻ thi-1 hsdS20 ($r_B^-$, $m_B^-$) supE44 recA13 ara-14 leuB6 proA2 lacY1 galK2 rpsL20 ($str^r$) xyl-5 mtl-1) and DH5α (F⁻φ80lacZΔM15 Δ(lacZYA-argF)U169 recA1 endA1 hsdR17 ($r_k^-$, $m_k^+$) phoA supE44 thi-1 gyrA96 relA1 λ⁻) were obtained from Invitrogen.

to the coding sequence. In parallel, the secretion signal peptide of the TrXyl11B gene was amplified by PCR from a genomic clone of TrXyl11B (pXYN2K2, example 11.3) using primers to introduce BglII at the 5' end and an NheI site at 3' end of the amplicon, which was subsequently cloned using these restriction sites into pBluescript® II KS-(Stratagene) to generate the plasmid pXYNSS-Nhe. The amplicon was then cloned into the unique NheI and Bgl II sites of pXYNSS-Nhe. A fragment comprising the TrCel6A gene operably linked to the secretion signal peptide of TrXyl11B with BglII sites at the 5' and 3' ends was subsequently amplified by PCR from this intermediate construction using primers (BGL2XYF and C2STU3). This amplicon was cloned in the BglII site of the YEp352/PGK91-1ΔNheI vector to yield to the YEp352/PGK91-1ΔNheI-xyl$_{SS}$-cbh2 vector (FIG. 2a) and transformed in yeast strain DBY747 using the procedure described by Gietz, R. D. and Woods, R. A. (Gietz, R. D. and Woods, R. A. 2002. Meth. Enzym. 350: 87-96) and plated on SC-Ura plate. Primer sequences are listed below:

```
                StuI    NheI
C2STU5: 5'GAT AGG CCT GCT AGC TGC TCA AGC GTC TGG GGC      (SEQ ID NO: 24)

StuI    BglII   KpnI
C2STU3: 5'ATC AGG CCT AGA TCT GGT ACC TTA CAG GAA CGA TGG  (SEQ ID NO: 25)

BglII
BGL2XYF:5'GAT CAG ATC TAT GGT CTC CTT CAC CTC CCT C        (SEQ ID NO: 26)
```

Humicola insolens and Phanerochaete chrysosporium strains were obtained from ATCC® (#22082™ and #201542™ respectively).

The YEp352/PGK91-1 vector was obtained from the National Institute of Health. The YEpFLAG-1 vector was obtained from Sigma as a part of the Amino-Terminal Yeast FLAG Expression Kit. The pALTER®-1 vector was obtained from Promega as a part of the Altered Site® II in vitro mutagenesis System. The pBluescript® II KS-vector was obtained from Stratagene.

Example 2

Cloning of the TrCel6A gene into the YEp352/PGK91-1 and Transformation in Yeast

2.1 Isolation of total RNA from T. reesei and Generation of Total cDNA.

T. reesei biomass was grown under inducing conditions as described in example 13 then 50 mg of biomass was used to isolate total RNA with the Absolutely RNA® Miniprep Kit (Stratagene) according to the manufacturer procedure. Total cDNA was generated from the total RNA using the SuperScript™II Reverse Transcriptase (Invitrogen) according to the manufacturer procedure.

2.2 Cloning and Transformation in Yeast.

In order to facilitate cloning using NheI and KpnI restriction enzymes, the unique NheI site at position 1936 of the YEp352/PGK91-1 vector was blunted using the DNA Polymerase I large (Klenow) fragment to generate YEp352/PGK91-1ΔNheI.

The cbh2 gene encoding TrCel6A was amplified by PCR from total cDNA (generated as described in example 2.1) using primers (C2STU 5 and C2STU3 that introduce StuI-NheI sites upstream and a KpnI-BglII-StuI sites downstream SC-Ura pate contains:

| Component | g/L |
|---|---|
| Yeast Nitrogen Base without amino acid and ammonium sulfalte (BD) | 1.7 |
| (NH$_4$)$_2$SO$_4$ (Sigma) | 5.0 |
| Complete Supplement Media without uridine (Clontech) | 0.77 |
| Agar (BD) | 17.0 |
| Glucose (Fisher) | 20.0 |
|  | pH 5.6 |

Example 3

Making Error Prone-PCR Libraries of cbh2

Random mutagenesis libraries were generated using two methods: a Mn$^{2+}$/dITP method and a biased nucleotides method. For the Mn$^{2+}$/dITP method, the TrCel6A gene was amplified from YEp352/PGK91-1ΔNheI-xyl$_{SS}$-cbh2 vector using the above-mentioned C2STU3 and BGL2XYF primers in a two step PCR method. In the first step, the amplification occurs for 20 cycles in the presence 20 μM MnCl$_2$. The second step is done with the same primers but using the product from the first step as template and with 0, 25, 50, 75 or 100 μM dITP (0 μM being a control). For the biased nucleotides method, the PCR is conducted with 1:3, 1:5 or 1:10 molar ratio between purine bases and pyrimidine bases respectively.

To get mostly mutations in the core of the enzyme, the final amplicon in both cases was cloned using the XhoI and KpnI restriction sites in the YEp352/PGK91-1ΔNheI-xyl$_{SS}$-cbh2 vector (XhoI cuts right after sequence coding for S55's codon in the linker of the enzyme) and transformed in S. cerevisiae strain DBY747.

Example 4

Making Site-Directed Semi-Random Libraries of TrCel6A

Glycine residues have no β-carbon and thus have considerably greater backbone conformational freedom. By analyzing the three-dimensional structure of TrCel6A, 4 glycines residues were targeted to decrease this degree of freedom, namely G90, G85, G231 and G384. All but G231 positions were saturated and G231 was randomly mutated for an alanine, a proline, a serine or a threonine by megaprimer PCR using the following primers:

```
G90 to Xxx:
                                    (SEQ ID NO:27)
5' CCA ACA AAA GGG TTN NNT GAA TAC GTA GCG G

G85 to Xxx:
                                    (SEQ ID NO:28)
5' CCC AAG GAG TGA CNN NAA CAA AAG GGT TG

G231 to A/P/S/T:
                                    (SEQ ID NO:29)
5' GGT GAC CAA CCT CNC NAC TCC AAA GTG TG

G384 to Xxx:
                                    (SEQ ID NO:30)
5' CCG CAA ACA CTN NNG ACT CGT TGC TG
```

All amplicons were cloned in the YEp352/PGK91-1ΔN-heI-xyl$_{SS}$-cbh2 vector as described in example 3.

Example 5

Screening of TrCel6A Gene Libraries for Modified Family 6 Cellulases with Increased Thermostability A total of 3371 TrCel6A variants generated as per Example 3 and 4 were screened as follows: each yeast colony was cultured in a well of a 96-deep well plate containing 1 mL of YPD (1% yeast extract, 2% peptone, 2% glucose) media and one 1.5 mm glass bead for 2 days in a Vortemp apparatus (Labnet) at 650 rpm and at 30° C. The plate was centrifuged at 3,000×g for 5 minutes then 300 μL of supernatant was filtered through each of two Biodyne B positively charged nylon membranes (Pall Gelman) using a Bio-Dot apparatus (Bio-Rad).

Membranes were placed on a moist (not wet) Whatman paper containing 50 mM sodium citrate at pH 4.8. One was incubated for 12 minutes at 62° C. and the other one at room temperature (control). Membranes were then placed on agar plates containing β-glucan substrate and incubated overnight at 50° C. in a humidity chamber:

| Component | g/L |
| --- | --- |
| (NH$_4$)$_2$SO$_4$ (Sigma) | 5.0 |
| β-glucan (Barley, Medium Viscosity; Megazyme) | 2.0 |
| Agar (BD) | 17.0 |
| Glucose (Fisher) | 20.0 |
| | pH 5.6 |

Agar plates were then stained 30-60 minutes by covering them with a 0.1% (w/v) Congo Red solution then rinsed 2-3 times with demineralized water to remove unbound dye and covered with 1M NaCl for 10-15 min. The clearing zones could be observed and compared between the control and the plate that was covered with the heat treated membrane. Each plate was scrutinized by at least two people and every positive variant that appeared to maintain its activity after the 12 min incubation at 62° C. when compared to the wild-type TrCel6A control was considered as potential positive. Each potential positive clone was produced again in microculture to allow observation of the phenotype on an additional occasion and to reduce the possibility of false negative.

From that screening, five positive clones were sequenced to identify the mutations they carry. Clone E6 contained a S413P mutation, clones G3 and F7 both contained a G231S mutation, clone A3 contained a N305S mutation and clone 7 contained a R410Q mutation as well as a G82E mutation at the end of the linker peptide.

Example 6

Cloning Modified TrCel6A Genes into the YEpFLAG-1 Vector for Higher Expression from *Saccharomyces cerevisiae*

In order to facilitate cloning of the modified TrCel6A genes identified in Example 5 into the YEpPLAG-1 vector in such a way as to operabling link the genes to the αmating factor secretion signal peptide, two modifications were necessary. First, the unique KpnI site present in the α secretion signal peptide sequence (bp 1457) of the YEpFLAG-1 vector was removed. This was done by PCR using two complementary mutagenic primers (5'-FLAGΔKpnI and 3'-FLAGΔKpnI). The mutagenesis reaction was then digested with DpnI for 1 hour at 37° C. and the plasmid was allowed to recircularize by placing the tube in boiling water and allowed to cool slowly to room temperature. This reaction was transformed directly in *E. coli* DH5α chemically competent cells. A clone that was digested only once with KpnI was sequenced to confirm the desired mutation and was used for further work and named YEpFLAGΔKpn. Primer sequences are listed below:

```
                              ΔKpnI
5'-FLAGΔKpnI: 5'CTA AAG AAG AAG GGG TAC ATT TGG ATA AAA GAG AC  (SEQ ID NO:31)

66 KpnI
3'-FLAGΔKpnI: 5'GTC TCT TTT ATC CAA ATG TAC CCC TTC TTC TTT AG  (SEQ ID NO:32)
```

Second, the *T. reesei* cbh1 gene was amplified from pCOR132 (Example 11.2) by PCR using primers to introduce XhoI-NheI sites at the 5' end and Kpn1-Apa1 sites at 3' end of the amplified fragment. This fragment was then inserted as an XhoI/ApaI fragments into the XhoI/ApaI linearized YEpFLAG-1 expression vector. The resulting vector, YEpFLAGΔKpn10, allows insertion of the modified TrCel6A genes identified in Example 5 as NheI/KpnI fragments in such a way that the coding regions are operably linked to the α secretion signal peptide.

The YEp352/PGK91-1ΔNheI-xyl$_{SS}$-cbh2 vectors containing native or modified TrCel6A genes were isolated from transformants of yeast strain DBY747 using method modified from Hoffman and Winston (Hoffman, C. S., and Winston, F. 1987. *Gene* 57: 267-272) and transformed in *E. coli* HB101 chemically competent cells. The modified TrCel6A genes were removed from the YEp352/PGK91-1ΔNheI-xyl$_{SS}$-cbh2 vectors by digestion with NheI and KpnI and cloned in the YEpFLAGΔKpn10 using the same restriction enzymes. The final constructs, YEpFLAGΔKpn10-cbh2, YEpFLAGΔ-Kpn10-G82E-R410Q, YEpFLAGΔKpn10-N305S YEp-FLAGΔKpn10-S413P and YEpFLAGΔKpn10-G231S (FIG. 2b), were transformed into yeast strain BJ3505 using the procedure described by Gietz and Woods (Gietz R. D. and Woods R. A. 2002. *Meth. Enzym.* 350: 87-96) and plated on SC-trp plate. The integrity of the cloned region of all variants was confirmed by DNA sequence analysis. The amino acid sequence of the parent TrCel6A produced by this yeast vector (SEQ ID NO. 23) shows the C-terminal extension containing the FLAG peptide. However, it was determined experimentally that this small peptide extension does not in any way contribute to the thermostability, thermophilicity or alkalophilicity of the parent or modified TrCel6A cellulases.

SC-trp Pate Contains:

| Component | g/L |
| --- | --- |
| Yeast Nitrogen Base without amino acid and ammonium sulfalte (BD) | 1.7 |
| (NH$_4$)$_2$SO$_4$ (Sigma) | 5.0 |
| Yeast Synthetic Drop-Out Media Supplement without Tryptophan (Sigma) | 1 |
| Agar (BD) | 20 |
| Glucose (Fisher) | 20 |

Example 7

Generation of Other TrCel6A Variants, PcCel6A, PcCel6A-S407P, HiCel6A and HiCel6A-Y420P and Their Cloning in the YEpFLAG-1 Vector 7.1 Generation of Other TrCel6A Variants.

TrCel6A variant R410Q-S413P was obtained by error-prone PCR on the TrCel6A-S413P variant while cloned in the YEp352/PGK91-1ΔNheI using the Mutazyme® II DNA polymerase (Stratagene). It was then amplified from that source using primers 5'FLAG-Cel6A-GR and 3'FLAG-Cel6A-GR that introduce sequences homologue to the YEp-FLAG-1 vector upstream the NheI site and downstream the ApaI site respectively.

Mutagenic primers in conjunction with primer 3'FLAG-Cel6A-GR were used to generate megaprimer PCR of the following TrCel6A mutation combinations: G231S-S413P, N305S-S413P, G231S-N305S-S413P, G231S-R410Q-S413P, N305S-R410Q-S413P and G231S-N305S-R410Q-S413P. The resulting PCR products were isolated and used as a reverse primer in conjunction with the forward primer 5'FLAG-Cel6A-GR to generate final constructs. Primers sequences are listed below:

5'G231SCBH2
(SEQ ID NO: 35)
5'GGT GAC CAA CCT CTC TAC TCC AAA GTG TG

5'N305SGBH2
(SEQ ID NO: 36)
5'CAA TGT CGC CAG CTA CAA CGG G

5'Cel6A-E82G
(SEQ ID NO: 38)
5'GTA CCT CCA GTC GGA TCG GGA ACC GCT

5'FLAG-Cel6A-GR
(SEQ ID NO:39)
5'AGA GAC TAC AAG GAT GAC GAT GAC AAG GAA TTC CTC GAG GCT AGC TGC TCA AGC G

3'FLAG-Cel6A-GR
(SEQ ID NO: 40)
5'GAC CCA TCA GCG GCC GCT TAC CGC GGG TCG ACG GGC CCG GTA CCT TAC AGG AAC G 7.2 Generation PcCel6A and PcCel6A-S407P.

Lyophilized *P. chrysosporium* was resuspended in 300 μL sterile H$_2$O and 50 μL were spreaded onto PDA plates. Plates were incubated at 24° C. for 4 days. Spores for *P. chrysosporium* were inoculated on a cellophane circle on top of a PDA plate and biomass was harvested after 4-6 days at 24° C. Then, 50 mg of biomass was used to isolate total RNA with the Absolutely RNA® Miniprep Kit (Stratagene) according to the manufacturer procedure. Total cDNA was generated from the total RNA using the SuperScript™II Reverse Transcriptase (Invitrogen) according to the manufacturer procedure. Gene encoding for PcCel6A was amplified from the cDNA using the following primers:

5'PcCel6A-cDNA
(SEQ ID NO: 41)
5'CTA TTG CTA GCT CGG AGT GGG GAC AGT GCG GTG GC

3'PcCel6A-cDNA
(SEQ ID NO: 42)
5'CTA TTG AAT TCG GTA CCC TAC AGC GGC GGG TTG CAG CA GAA AC

PCR amplicon was clone in the pGEM®-T Easy vector by TA-cloning following manufacturer's recommendations. The gene encoding for PcCel6A was then amplified from that source using primers 5'FLAG-PcCel6A-GR and 3'FLAG-PcCel6A-GR that introduce sequences homologue to the YEpFLAG-1 vector upstream the NheI site and downstream the SstII site respectively.

Mutagenic primer 5'PcCel6A-S407P in conjunction with primer 3'FLAG-PcCel6A-GR was used to generate megaprimer PCR. The resulting PCR product was isolated and used as a reverse primer in conjunction with the forward primer 5'FLAG-PcCel6A-GR to generate final construct. Primers sequences are listed below:

5'FLAG-PcCel6A-GR
(SEQ ID NO: 43)
5'AAGGATGACGATGACAAGGAATTCCTCGAGGCTAGCTCGGAGTG GGG ACAGTGC

3'FLAG-PcCel6A-GR
(SEQ ID NO: 44)

-continued

```
5'TGGGACGCTCGACGGATCAGCGGCCGCTTACCGCGGCTACAGCG GCG

GGTTGGC

5'PcCel6A-S407P
                                            (SEQ ID NO: 45)
5'CCCCGCTACGACCCTACTTGTTCTCTG
```

7.3 Generation HiCel6A and HiCel6A-Y420P.

Lyophilized *H. insolens* was resuspended in 300 μL sterile H$_2$O and 50 μL was spreaded onto Emerson YPSS pH 7 agar plate (0.4% Yeast extract, 0.1% K$_2$HPO$_4$, 0.05% MgSO$_4$.7H$_2$O, 1.5% Glucose, 1.5% Agar). Fungus was incubated for 6 days at 45° C. then spores were inoculated in Novo media (as per Barbesgaard U.S. Pat. No. 4,435,307): Incubation for 48 hours at 37° C. in 100 mL growth phase media (2.4% CSL, 2.4% Glucose, 0.5% Soy oil, pH adjusted to 5.5, 0.5% CaCO$_3$), then 6 mL of pre-culture was transferred into 100 mL production phase media (0.25% NH$_4$NO$_3$, 0.56% KH$_2$PO$_4$, 0.44% K$_2$HPO$_4$, 0.075% MgSO$_4$.7H$_2$O, 2% Sigmacell, pH adjusted to 7, 0.25% CaCO$_3$) and culture was incubated for up to 4 days prior to biomass harvest. Then, 50 mg of biomass was used to isolate total RNA with the Absolutely RNA® Miniprep Kit (Stratagene) according to the manufacturer procedure. Total cDNA was generated from the total RNA using the SuperScript™II Reverse Transcriptase (Invitrogen) according to the manufacturer procedure. Gene encoding for HiCel6A was amplified from the cDNA using the following primers:

```
5'HiCel6A-cDNA
                                            (SEQ ID NO: 46)
5'CTA TTG CTA GCT GTG CCC CGA CTT GGG GCC AGT GC

3'HiCel6A-cDNA
                                            (SEQ ID NO: 47)
5'CTA TTG AAT TCG GTA CCT CAG AAC GGC GGA TTG GCA

TTA CGA AG
```

PCR Amplicon was Clone in the pGEMO-T Easy vector by TA-Cloning following manufacturer's recommendations. The gene encoding for HiCel6A was then amplified from that source using primers 5'FLAG-HiCel6A-GR and 3'FLAG-HiCel6A-GR that introduce sequences homologue to the YEpFLAG-1 vector upstream the NheI site and downstream the ApaI site respectively.

Mutagenic primer 5'HiCel6A-Y420P in conjunction with primer 3'FLAG-HiCel6A-GR was used to generate megaprimer PCR. The resulting PCR product was isolated and used as a reverse primer in conjunction with the forward primer 5'FLAG-HiCel6A-GR to generate final construct. Primers sequences are listed below:

```
5'FLAG-HiCel6A-GR
                                            (SEQ ID NO: 48)
5'AAGGATGACGATGACAAGGAATTCCTCGAGGCTAGCTGTGCCCC

GACTTGGGGC

3'FLAG-HiCel6A-GR
                                            (SEQ ID NO: 49)
5'AGCGGCCGCTTACCGCGGGTCGACGGGCCCGGTACCTCAGAACGG

CGGATTGGC
```

-continued

```
5'HiCel6A-Y420P
                                            (SEQ ID NO: 50)
5'GCCCGCTACGACCCTCACTGCGGTCTC
```

7.4 Cloning of the Other TrCel6A Variants, PcCel6A, PcCel6A-S407P, HiCel6A and HiCel6A-Y420P in YEp-FLAG-1 and Transformation in BJ3505.

The YEpFLAGΔKpn10 vector (example 6) was digested with NheI and ApaI and the empty vector fragment was isolated. This linear fragment and the final PCR products generated in example 8.1 and 8.3 were cloned and transformed simultaneously by in vivo recombination (Butler, T. and Alcalde, M. 2003. In Methods in Molecular Biology, vol. 231: (F. H. Arnold and G. Georgiou, editors), Humana Press Inc. Totowa (New Jersey), pages 17-22).

The YEpFLAGΔKpn10 vector (example 6) was digested with NheI and SstII and the empty vector fragment was isolated. This linear fragment and the final PCR products generated in example 8.2 were cloned and transformed simultaneously by in vivo recombination.

Example 8

Medium Scale Expression of Native and Modified Family 6 Cellulases in Yeast

One isolated colony of BJ3505 yeast containing YEp-FLAG-ΔKpn10-cbh2 was used to inoculate 5 mL of liquid SC-trp in a 20 mL test-tube. After an overnight incubation at 30° C. and 250 rpm, optical density at 600 m was measured and 50 mL of YPEM liquid media in a 250 mL Erlenmeyer flask was inoculated with the amount of yeast required to get a final OD$_{600}$ of 0.045. After 72 h of incubation at 30° C. and 250 rpm, supernatant was harvested with a 5 minutes centrifugation step at 3,000×g. The BJ3505 strains expressing the TrCel6A variants, wild-type HiCel6A and variant, wild-type PcCel6A and variant as well as the empty YEpFLAG-1 vector were cultured the same way.

SC-trp liquid media contains the same components as the SC-trp plate mentioned in example 7 without the agar. YPEM liquid media contains:

| Component | per Liter |
| --- | --- |
| Yeast Extract (BD) | 10 g |
| Peptone (BD) | 5.0 g |
| Glucose (Fisher) | 10 g |
| Glycerol (Fisher) | 30 mL |

Example 9

Characterization of Modified Family 6 Cellulases from Yeast Culture Supernatants 9.1 Comparison of the thermophilicity of the Modified TrCel6A with the Native TrCel6A.

The thermophilicity of each enzyme was determined by measuring the release of reducing sugars from a soluble β-glucan substrate at different temperatures. Specifically, in a 300 μL PCR plate, 50 μL of crude supernatant obtained as per Example 9 was mixed with 50 μL of pre-heated 1% (w/v) β-glucan (Barley, Medium Viscosity; Megazyme) in 55 mM sodium citrate pH 5.0 in 10 different columns of a 96-well PCR plate. Mixtures were incubated for 30 min. at 10 different temperatures of a gradient (56, 58.1, 59.8, 62.6, 66, 70, 73.4, 76.2, 78.1 and 80° C.) then released reducing sugars were measured as follows: 100 μL of DNS reagent was added to each well and the plate was incubated 20 minutes at 95° C.

DNS reagent contains:

| Component | g/L |
|---|---|
| 3,5-Dinitosalicylic acid (Acros) | 10 |
| Sodium hydroxide (Fisher) | 10 |
| Phenol (Sigma) | 2 |
| Sodium metabisulfate (Fisher) | 0.5 |

Once the temperature decreased below 40° C., 135 μL of each reaction mixture was transferred to individual wells of a 96-well microplate containing 65 μL of Rochelle salts (40% Sodium potassium tartrate) in each well and $OD_{560}$ was measured using a Fluostar Galaxy microplate reader equipped with a 560 nm filter. Blank value was measured by treating the supernatant from the strain carrying the empty vector the same way and was subtracted to each value. Then activity was expressed in percentage relatively to the highest value of the four parameters Polynomial fit for each variant except variant TrCel6A-G231S-N305S-R410Q-S413P for which a four parameters Log Normal fit was used (FIG. 6).

All modified Family 6 cellulases shown an improved optimal temperature when compared to their respective wild-type except variant TrCel6A-G231S-N305S-R40Q-S413P which on the other hand exhibits a broad temperature range with more then 80% of the maximum activity (FIG. 6). Among all TrCel6A variants, TrCel6A-S413P has the higher optimal temperature at 72.2° C., an increase of 5.6° C. compared to wild-type TrCel6A (FIG. 6a). PcCel6A-S407P and HiCel6A-Y420P also exhibit an increase in optimal temperature when compared to their respective wild-type (FIGS. 6b and c).

9.2 Comparison of the Alkalophilicity of the Modified TrCel6A with the Native TrCel6A.

Figure 7:
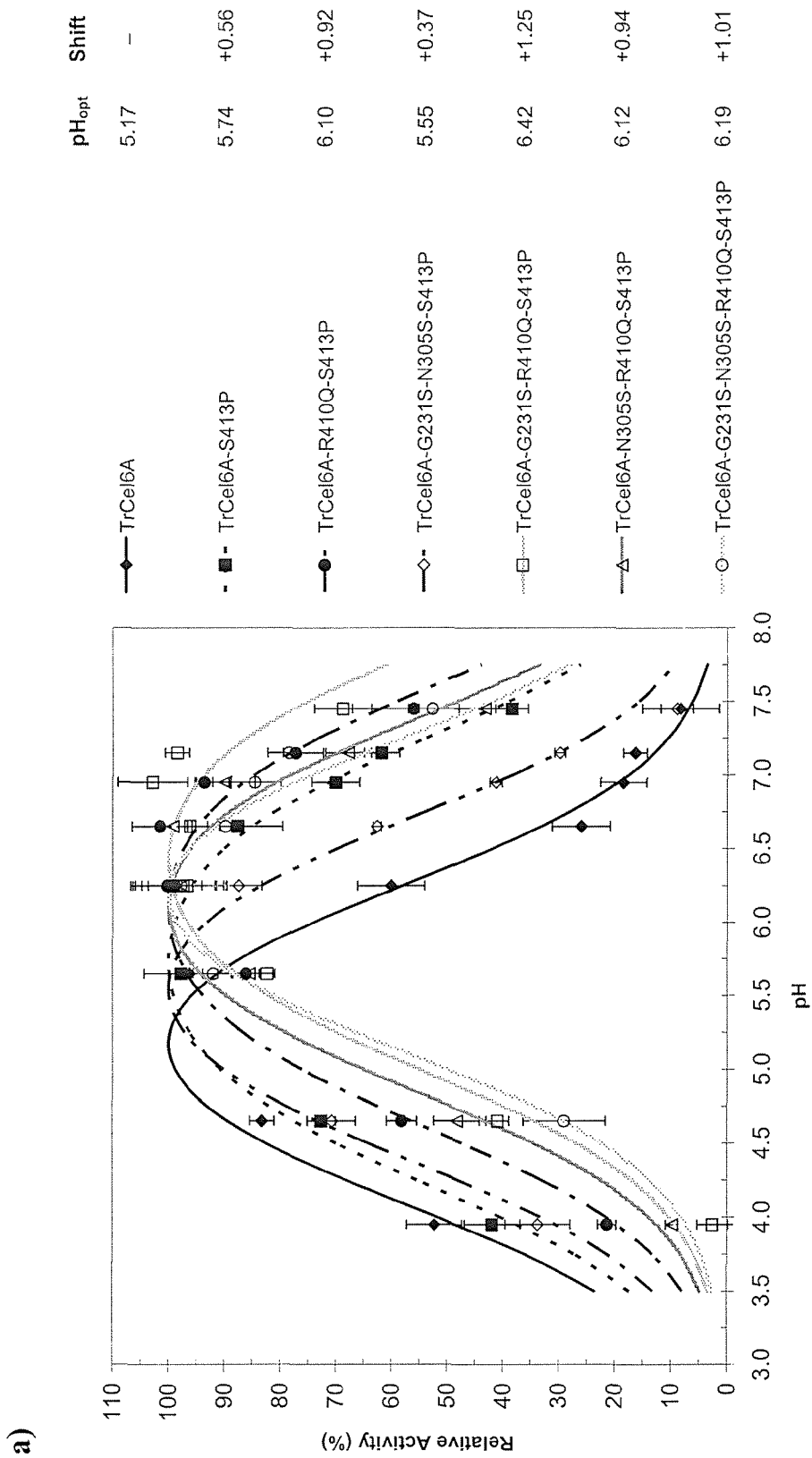
FIG. 7 shows the effect of pH on the enzymatic activity of a) the native TrCel6A and modified Family 6 cellulases TrCel6A-S413P, TrCel6A-G82E-G231S-N305S-R410Q-S413P, TrCel6A-R410Q-S413P, TrCel6A-G231S-N305S-S413P, TrCel6A-G231S-R410Q-S413P, TrCel6A-N305S-R410Q-S413P and TrCel6A-G231S-N305S-R410Q-S413P b) the native PcCel6A and modified Family 6 cellulases PcCel6A-S407P and c) the native HiCel6A and modified Family 6 cellulases HiCel6A-Y420P during 30 minutes incubation at pH 3.95-7.45. The data are normalized to the activity observed at the pH optimum for each enzyme.
Figure 7:
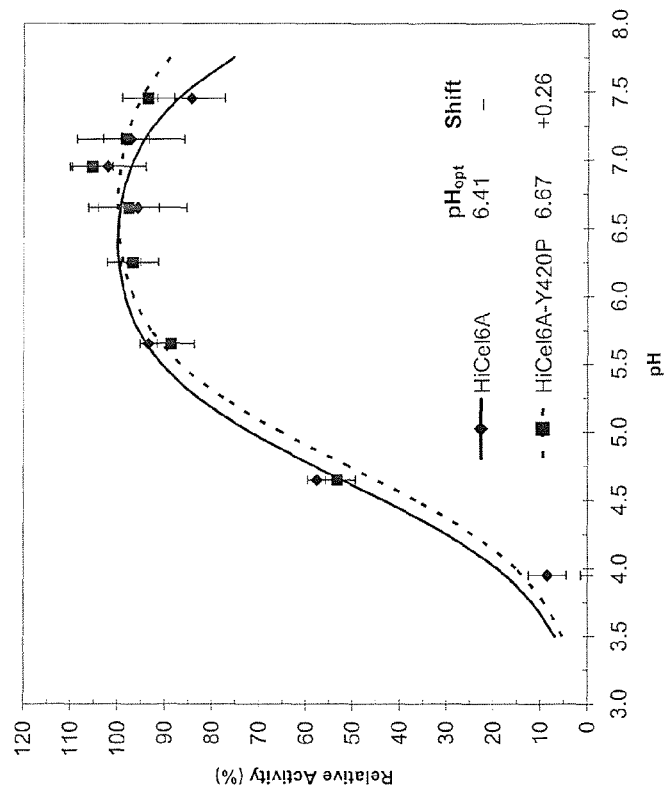
Figure 7:
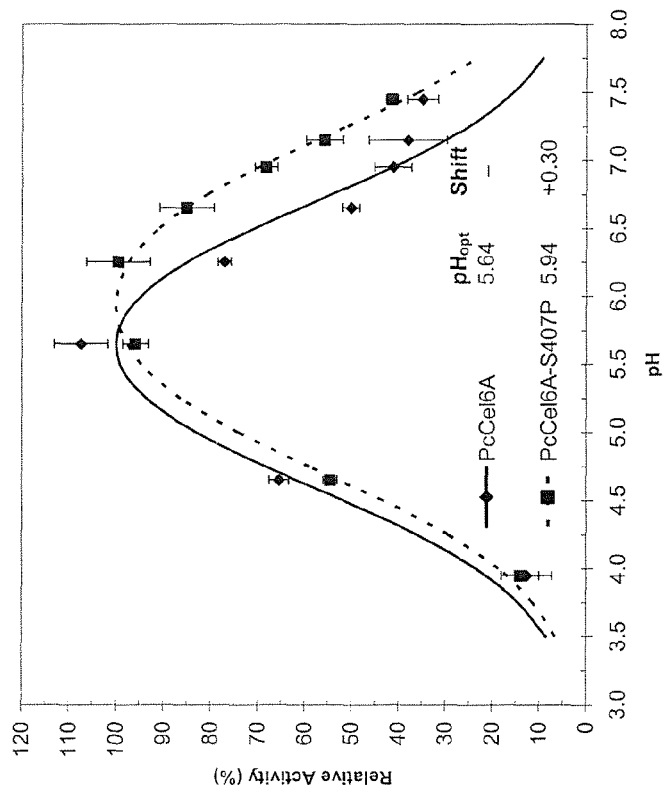

The alkalophilicity of each enzyme was determined by measuring the release of reducing sugars from a soluble β-glucan substrate at different pH. Specifically, in a 300 μL PCR plate, 50 μL of crude supernatant obtained as per example 9 was mixed to 50 μL of pre-heated 1% (w/v) β-glucan (Barley, Medium Viscosity; Megazyme) in 55 mM sodium citrate, 55 mM sodium phosphate pH 3.0, 4.0, 5.0, 5.75, 6.25, 6.75, 7.25 or 8.5 in 8 different columns of the plate (once mixed to the supernatant and heated at 60-65° C., pHs where 3.95, 4.65, 5.65, 6.25, 6.65, 6.95, 7.15 and 7.45 respectively). Mixtures were incubated 30 min. at 65° C. (60° C. for PcCel6A and variant) then released reducing sugars were measured as per Example 10.1. Background activity from the yeast host was measured by treating the supernatant from the strain carrying the empty vector the same way and this activity was subtracted from the activity value for each variant. Then activity was expressed in percentage relatively to the highest value of the three parameter mechanistic fit for each variant (FIG. 7).

All modified Family 6 cellulases exhibit increased alkalophilicity when compared to their wild-type. For TrCel6A, the most important shift was observed with variants TrCel6A-G231S-R410Q-S413P (+1.25 pH units) followed by TrCel6A-G231S-N305S-R410Q-S413P (+1.01 pH units).

9.3 Comparison of the Thermostability of the Modified TrCel6A with the Native TrCel6A.

Figure 5:
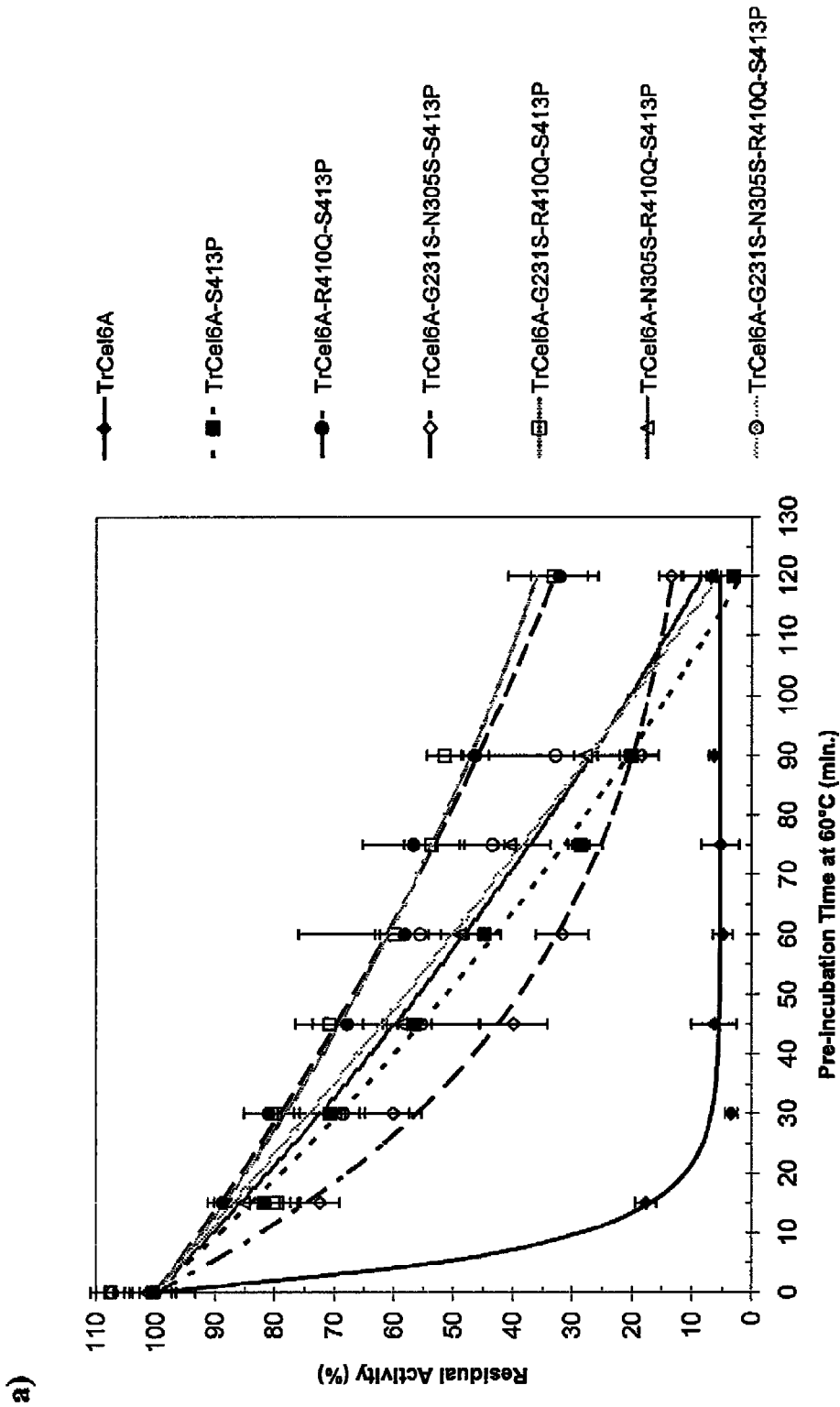
FIG. 5 shows the effect of increasing pre-incubation times on the relative residual activity (%), as measured by the release of reducing sugars a soluble β-glucan substrate in a 30 minutes assay at a) 65° C., of the native TrCel6A and modified Family 6 cellulases TrCel6A-S413P, TrCel6A-R410Q-S413P, TrCel6A-G231S-N305S-S413P, TrCel6A-G231S-R410Q-S413P, TrCel6A-N305S-R410Q-S413P and TrCel6A-G2311S-N305S-R410Q-S413P after 0-120 minutes incubation at 60° C. and b) 60° C., of the native PcCel6A and modified Family 6 cellulases PcCel6A-S407P after 0-120 minutes incubation at 55° C.
Figure 5:
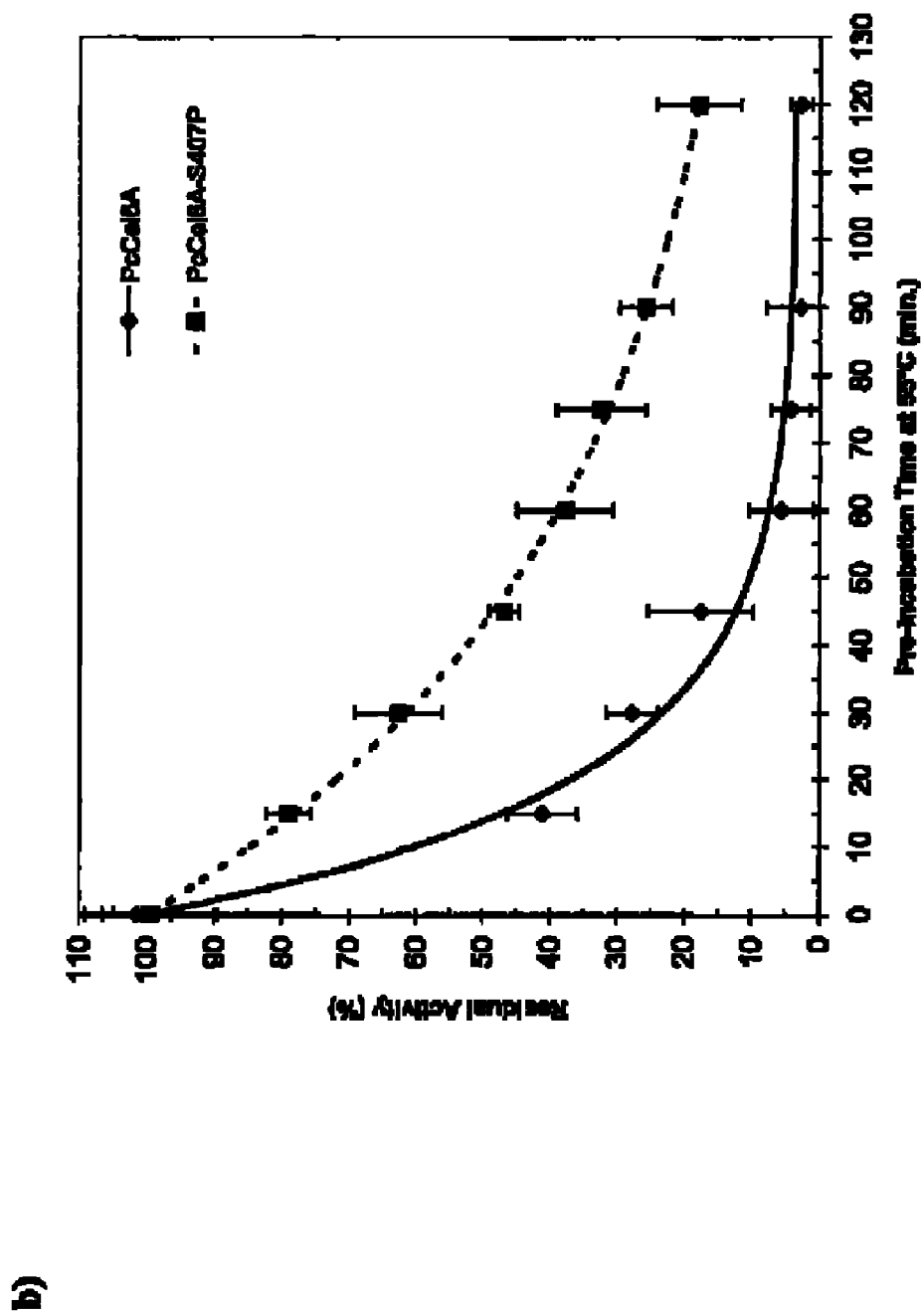

The thermostability of each enzyme was determined by measuring the release of reducing sugars from a soluble β-glucan substrate after different pre-incubation time of the supernatant at 60° C. (55° C. for PcCel6A and variant). Specifically, in a 300 μL PCR plate, 50 μL of crude supernatant obtained as per Example 9 was incubated at 60° C. (55° C. for PcCel6A and variant) for 0, 15, 30, 45, 60, 75, 90 and 120 minutes. Then, 50 μL of 1% (w/v) β-glucan (Barley, Medium Viscosity; Megazyme) in 55 mM sodium citrate pH 5.0 was added and mixtures were incubated 30 minutes 65° C. (60° C. for PcCel6A and variant). Released reducing sugars were then measured as per Example 10.1. Background activity from the yeast host was measured by treating the supernatant from the strain carrying the empty vector the same way and this activity was subtracted from the activity value for each variant. Finally, activity was expressed in percentage relatively to the highest value of the three parameter single exponential decay fit for each variant (FIG. 5).

All TrCel6A variants have shown increased thermostability when compared to wild-type TrCel6A (FIG. 5a). The S413P mutation results in a significant increase in the thermostability TrCel6A. TrCel6A-S413P retains 45% of its activity after 60 minutes at 60° C. whereas TrCel6A retains only 4% of its activity after 60 minutes. This represents a greater improvement in thermostability compared to that of the TrCel6A-S413Y variant disclosed in US Patent Publication No. 20060205042, which retained on average 41% of its activity under similar conditions. The highest improvement was observed with TrCel6A-R410Q-S413P and TrCel6A-G231S-R410Q-S413P as both retain 58 and 60% of their activity after 60 minutes at 60° C. respectively. Similarly to TrCel6A, PcCel6A-S407P retains 38% of its activity after 60 minutes at 55° C. whereas PcCel6A retains only 6% of its activity after 60 minutes (FIG. 5b). This supports the claim for which a proline at the equivalent position of TrCel6A residue 413 increases thermostability.

9.4 Comparison of the $T_{50}$ of the Modified TrCel6A with the Native TrCel6A.

Figure 4:
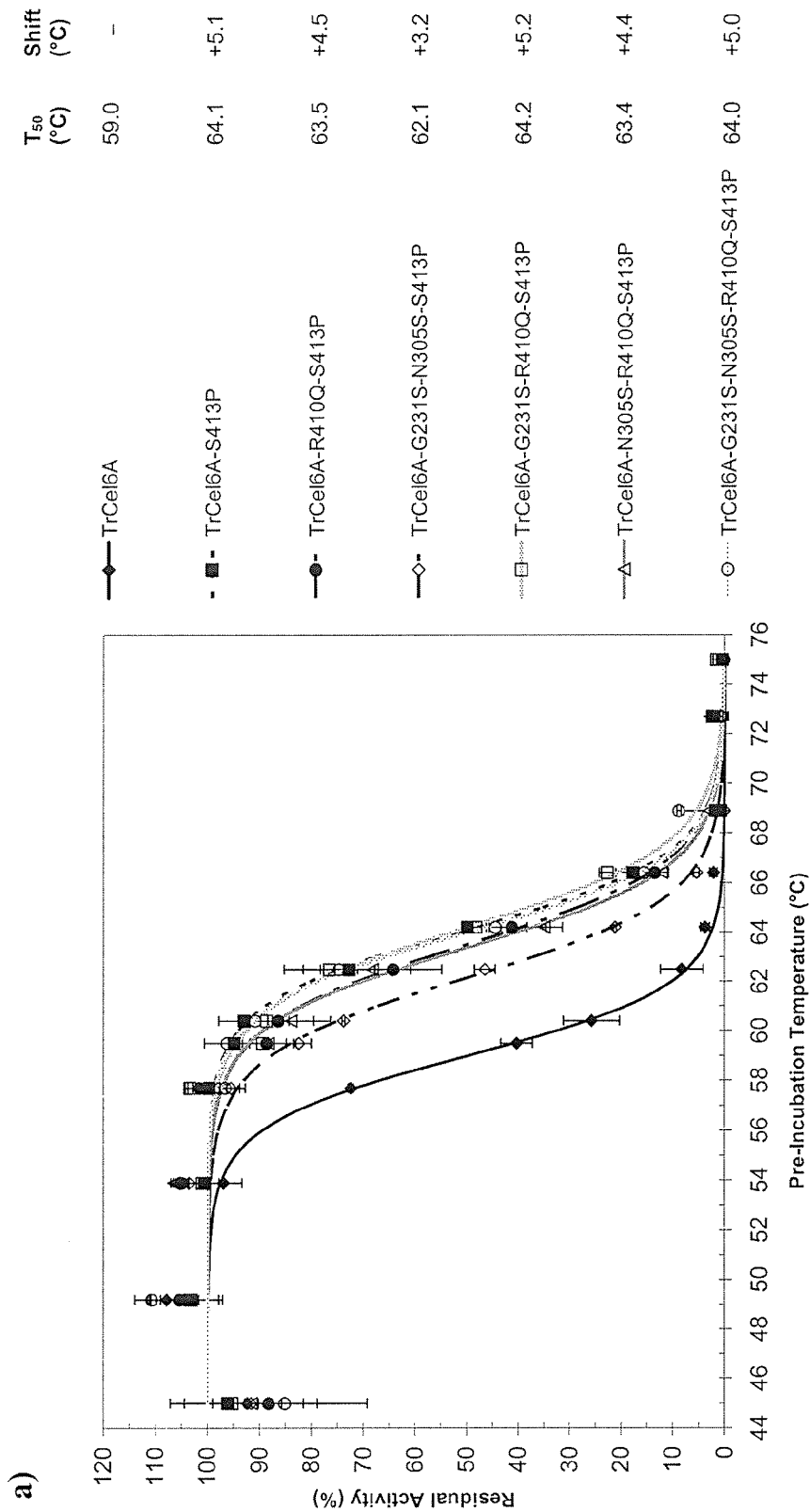
FIG. 4 shows the effect of pre-incubation temperature on the relative residual activity (%), as measured by the release of reducing sugars from β-glucan in a 30 minutes assay at a) 65° C., of the native TrCel6A and modified Family 6 cellulases TrCel6A-S413P, TrCel6A-R410Q-S413P, TrCel6A-G231 S-N305S-S413P, TrCel6A-G231S-R410Q-S413P, TrCel6A-N305S-R410Q-S413P and TrCel6A-G231S-N305S-R410Q-S413P, b) 60° C., of the native PcCel6A and modified Family 6 cellulases PcCel6A-S407P, c) 65° C., of the native HiCel6A and modified Family 6 cellulases HiCel6A-Y420P, after 15 minutes incubation at temperatures between 45° C. and 75° C.
Figure 4:
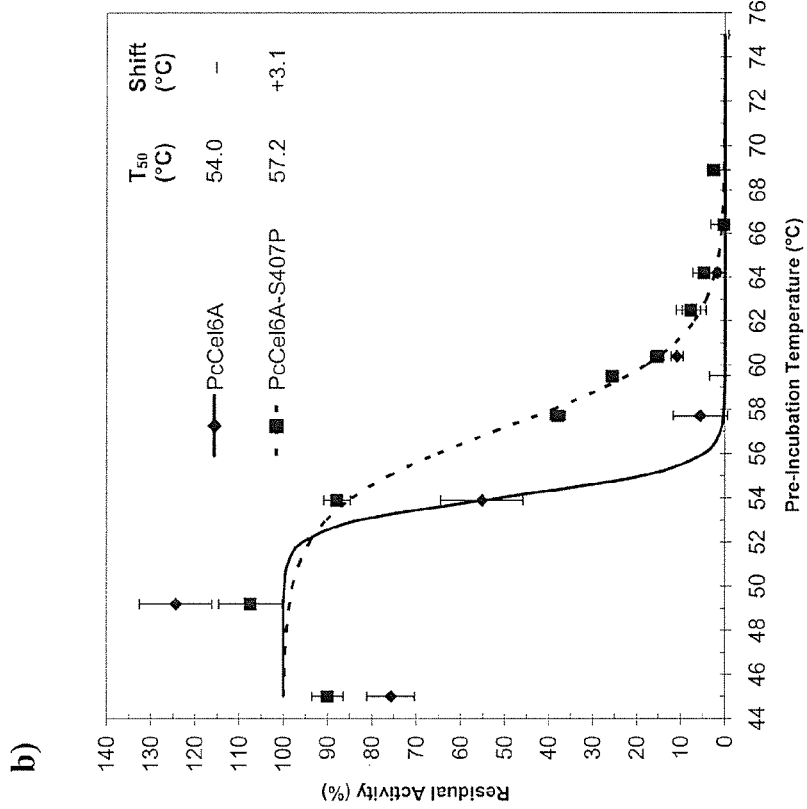

$T_{50}$ herein is defined as the temperature at which the crude yeast supernatant retains 50% of its β-glucan hydrolyzing activity after 15 minutes of incubation without substrate. It was determined by measuring the release of reducing sugars from a soluble β-glucan substrate after 15 minutes of pre-incubation at different temperatures. Specifically, in a 300 μL PCR plate, 50 μL of crude supernatant obtained as per Example 9, was incubated at 45, 49.2, 53.9, 57.7, 59.5, 60.4, 62.5, 64.2, 66.4, 68.9, 72.7 or 75° C. for 15 minutes. Then, 50 μL of 1% (w/v) β-glucan (Barley, Medium Viscosity; Megazyme) in 55 mM sodium citrate pH 5.0 was added and mixtures were incubated 30 minutes 65° C. (60° C. for PcCel6A and variant). Released reducing sugars were then measured as per Example 10.1. Background activity from the yeast host was measured by treating the supernatant from the strain carrying the empty vector the same way and this activity was subtracted from the activity value for each variant. Finally, activity was expressed in percentage relatively to the highest value of the four parameter sigmoid fit for each variant (FIG. 4).

The $T_{50}$ of the TrCel6A-S413P was determined to be 64.1° C., as compared to 59° C. for the parent TrCel6A (FIG. 4a). This represents an increase in the thermostability by over 5° C. through the introduction of the S413P mutation. This represents a significant improvement in enzyme stability compared to the S413Y mutation disclosed US Patent Publication No. 20060205042, which shows a very modest 0.2-0.3° C. increase in the Tm of the TrCel6A-S413Y over TrCel6A.

Although the methods to determine the Tm disclosed US Patent Publication No. 20060205042 is different from the determination of T50 disclosed herein, both methods seek to determine the temperature at which the protein undergoes a significant and structural change that leads to irreversible inactivation. The $T_{50}$ of the other TrCel6A variants was at least 3.2° C. higher then wild-type TrCel6A.

PcCel6A-S407P and Hicel6A-Y420P also have shown an increase in TSO when compared to their respective parent enzyme (FIGS. 4b and c). This also supports the claim for which a proline at the equivalent position of TrCel6A residue 413 increases thermostability in Family 6 cellulases.

Example 10

Making Genetic Constructs Comprising Modified Family 6 Cellulase DNA Sequences 10.1 Isolation of *Trichoderma reesei* Genomic DNA and Construction of *T. reesei* Genomic Libraries A strain of *Trichoderma reesei* obtained derived from RutC30 (ATCC #56765; Montenecourt, B. and Eveleigh. D. 1979. *Adv. Chem. Ser.* 181: 289-301) comprising a disrupted native TrCel6A gene was used. RutC30 is derived from *Trichoderma reesei* Qm6A (ATCC # 13631; Mandels, M. and Reese, E. T. 1957. *J. Bacteriol.* 73: 269-278). It is well understood by those skilled in the art that the procedures described herein, the genetic constructs from these strains, and the expression of the genetic constructs in these strains are applicable to all *Trichoderma* strains derived from Qm6A.

To isolate genomic DNA, 50 mL of Potato Dextrose Broth (Difco) was inoculated with *T. reesei* spores collected from a Potato Dextrose Agar plate with a sterile inoculation loop. The cultures were shaken at 200 rpm for 2-3 days at 28° C. The mycelia was filtered onto a GFA glass microfibre filter (Whatman) and washed with cold, deionized water. The fungal cakes were frozen in liquid nitrogen crushed into a powder with a pre-chilled mortar and pestle; 0.5 g of powdered biomass was resuspended in 5 mL of 100 mM Tris, 50 mM EDTA, pH 7.5 plus 1% sodium dodecyl sulphate (SDS). The lysate was centrifuged (5000 g for 20 min, 4° C.) to pellet cell debris. The supernatant was extracted with 1 volume buffer (10 mM Tris, 1 mM EDTA, pH 8.0) saturated phenol followed by extraction with 1 volume of buffer-saturated phenol:chloroform:isoamyl alcohol (25:24:1) in order to remove soluble proteins. DNA was precipitated from the solution by adding 0.1 volumes of 3 M sodium acetate, pH 5.2 and 2.5 volumes of cold 95% ethanol. After incubating for at least 1 h at −20° C., the DNA was pelleted by centrifugation (5000 g for 20 min, 4° C.), rinsed with 10 mL 70% ethanol, air-dried and resuspended in 1 mL 10 mM Tris, 1 mM EDTA, pH 8.0. RNA was digested by the addition of Ribonuclease A (Roche Diagnostics) added to a final concentration of 0.1 mg/mL and incubation at 37° C. for 1 hour. Sequential extractions with 1 volume of buffer-saturated phenol and 1 volume of buffer-saturated phenol:chloroform:isoamyl alcohol (25:24:1) was used to remove the ribonuclease from the DNA solution. The DNA was again precipitated with 0.1 volumes of 3 M sodium acetate, pH 5.2 and 2.5 volumes of cold 95% ethanol, pelleted by centrifugation, rinsed with 70% ethanol, air-dried and resuspended in 50 μL of 10 mM Tris, 1 mM EDTA, pH 8.0. The concentration of DNA was determined by measuring the absorbance of the solution at 260 nm (p. C1 in Sambrook et al., Molecular Cloning: A Laboratory Manual, Second Edition, Cold Spring Harbor Press 1989, which is incorporated herein by reference, and hereafter referred to as Sambrook et al.).

Two plasmid libraries and one phage library were constructed using genomic DNA isolated from *T. reesei* strain M2C38. The plasmid libraries were constructed in the vector pUC119 (Viera and Messing, *Methods Enzymol.* 153:3, 1987) as follows: 10 μg genomic DNA was digested for 20 hrs at 37° C. in a 100 μL volume with 2 units/μg of BamH1 or EcoR1 restriction enzymes. The digested DNA was fractionated on a 0.75% agarose gel run in 0.04 M Tris-acetate, 1 mM EDTA and stained with ethidium bromide. Gel slices corresponding to the sizes of the genes of interest (based on published information and Southern blots) were excised and subjected to electro-elution to recover the DNA fragments (Sambrook et al., pp. 6.28-6.29). These enriched fractions of DNA were ligated into pUC119 in order to create gene libraries in ligation reactions containing 20-50 μg/mL DNA in a 2:1 molar ratio of vector:insert DNA, 1 mM ATP and 5 units T4 DNA ligase in a total volume of 10-15 μL at 4° C. for 16 h. *Escherichia coli* strain HB101 was electroporated with the ligation reactions using the Cell Porator System (Gibco/BRL) following the manufacturer's protocol and transformants selected on LB agar containing 70 μg/mL ampicillin.

The phage library was constructed in the vector λDASH (Stratagene, Inc.) as follows: genomic DNA (3 μg) was digested with 2, 1, 0.5 and 0.5 units/μg BamHI for 1 hour at 37° C. to generate fragments 9-23 kB in size. The DNA from each digest was purified by extraction with 1 volume Tris-staturated phenol:choroform:isoamyl alcohol (25:24:1), followed by precipitation with 10 μL 3 M sodium acetate, pH 5.2 and 250 μl 95% ethanol (−20° C.). The digested DNA was pelleted by microcentrifugation, rinsed with 0.5 mL cold 70% ethanol, air-dried and resuspended in 10 μL sterile, deionized water. Enrichment of DNA fragments 9-23 kB in size was confirmed by agarose gel electrophoresis (0.8% agarose in 0.04 M Tris-acetate, 1 mM EDTA). Digested DNA (0.4 μg) was ligated to 1 μg λDASH arms predigested with BamHI (Stratagene) in a reaction containing 2 units T4 DNA ligase and 1 mM ATP in a total volume of 5 μl at 4° C. overnight. The ligation mix was packaged into phage particles using the GigaPack® II Gold packaging extracts (Stratagene) following the manufacturer's protocol. The library was titred using the *E. coli* host strain XL1-Blue MRA (P2) and found to contain 3×10⁵ independent clones.

10.2 Cloning the Cellobiohydrolase I (cbh1) and Cellobiohydrolase II (cbh2) Genes from pUC119 Libraries

*E. coli* HB101 transformants harboring cbh1 or cbh2 clones from recombinant pUC119-BamH1 or -EcoRI libraries were identified by colony lift hybridization: 1-3×10⁴ colonies were transferred onto HyBond™ nylon membranes (Amersham); membranes were placed colony-side up onto blotting paper (VWR 238) saturated with 0.5 M NaOH, 1 M NaCl for 5 min to lyse the bacterial cells and denature the DNA; the membranes were then neutralized by placing them colony-side up onto blotting paper (VWR 238) saturated with 1.5 M Tris, pH 7.5 plus 1 M NaCl for 5 min; the membranes were allowed to air-dry for 30 min and the DNA was then fixed to the membranes by baking at 80° C. for 2 h.

$^{32}$P-labelled probes were prepared by PCR amplification of short (0.7-1.5 kB) fragments of the cbh1 and cbh2 coding regions from the enriched pool of BamH1 or EcoR1 fragments, respectively, in a labelling reaction containing 10-50 ng target DNA, and 0.2 mM each of d(GCT)TP, 0.5 μM dATP, 20-40 μCi α-$^{32}$P-dATP, 10 pmole oligonucleotide primers and 0.5 units Taq polymerase in a total volume of 20 μL. The reaction was subjected to 6-7 cycles of amplification (95° C., 2 min; 56° C., 1.5 min; 70° C., 5 min). The amplified, $^{32}$P-labelled DNA was precipitated by the addition of 0.5 mL 10%

(w/v) trichloroacetic acid and 0.5 mg yeast tRNA. The DNA was pelleted by microcentrifugation, washed twice with 1 mL 70% ethanol, air-dried and resuspended in 1 M Tris pH 7.5, 1 mM EDTA.

Nylon membranes onto which the recombinant pUC119 plasmids had been fixed were prehybridized in heat-sealed bags for 1 h at 60-65° C. in 1 M NaCl, 1% SDS, 50 mM Tris, 1 mM EDTA pH 7.5 with 100 μg/mL denatured sheared salmon sperm DNA. Hybridizations were performed in heat-sealed bags in the same buffer with only 50 μg/mL denatured sheared salmon sperm DNA and $5 \times 10^6$-$5 \times 10^7$ cpm of denatured cbh1 or cbh2 probe for 16-20 h at 60-65° C. Membranes were washed once for 15 min with 1 M NaCl, 0.5% SDS at 60° C., twice for 15 min each with 0.3M NaCl, 0.5% SDS at 60° C. and once for 15 min with 0.03M NaCl, 0.5% SDS at 55° C. Membranes were again placed in heat-sealed bags and exposed to Kodak RP X-ray film to 16-48 h at −70° C. The X-ray film was developed following the manufacturer's protocols. Colonies giving strong or weak signals were picked and cultured in 2×YT media supplemented with 70 μg/mL ampicillin. Plasmid DNA was isolated from these cultures using the alkaline lysis method (Sambrook, et al., pp. 1.25-1.28) and analyzed by restriction digest, Southern hybridization (Sambrook, et al., pp. 9.38-9.44) and PCR analysis (Sambrook, et al., pp. 14.18-14,19).

Clones carrying the cbh1 gene were identified by colony lift hybridization of the pUC119-BamH1 library with a 0.7 kb cbh1 probe prepared using oligonucleotide primers designed to amplify bp 597-1361 of the published cbh1 sequence (Shoemaker et al., Bio/Technology 1: 691-696, 1983; which is incorporated herein by reference). A cbh1 clone, pCOR132, was isolated containing a 5.7 kb BamH1 fragment corresponding to the promoter (4.7 kb) and 1 kb of the cbh1 structural gene (2.3 kb). From this, a 2.5 kb EcoR1 fragment containing the cbh1 promoter (2.1 kb) and 5' end of the cbh1 coding region (0.4 kb) was subcloned into pUC119 to generate pCB152. Clones carrying the cbh2 gene were identified by colony lift hybridization of the pUC119-EcoR1 library with a 1.5 kb cbh2 probe prepared using oligonucleotide primers designed to amplify bp 580-2114 of the published cbh2 sequence (Chen et al. Bio/Technology 5: 274-278, 1987). A cbh2 clone, pZUK600 was isolated containing a 4.8 kb EcoR1 fragment corresponding to the promoter (600 bp), structural gene (2.3 kb) and terminator (1.9 kb).

10.3 Cloning Xylanase II (xln2) gene from λDASH Libraries

Digoxigen-11-dUTP labelled probes were prepared from PCR amplified coding regions of the xln2 gene by random prime labeling using the DIG Labeling and Detection kit (Roche Diagnostics) and following the manufacturer's protocols. Genomic clones containing the xln2 gene were identified by plaque-lift hybridization of the λDASH library. For each gene of interest, $1 \times 10^4$ clones were transferred to Nytran® (Schleicher and Schull) nylon membranes. The phage particles were lysed and the phage DNA denatured by placing the membranes plaque-side up on blotting paper (VWR238) saturated with 0.5 M NaOH, 1 M NaCl for 5 min. The membranes were then neutralized by placing them plaque-side up onto blotting paper saturated with 1.5 M Tris, pH 7.5 plus 1 M NaCl for 5 min and subsequently allowed to air-dry for 30 min. The DNA was then fixed to the membranes by baking at 80° C. for 2 h. The membranes were prehybridized in heat-sealed bags in a solution of 6× SSPE, 5× Denhardt's, 1% SDS plus 100 μg/mL denatured, sheared salmon sperm DNA at 65° C. for 2 h. The membranes were then hybridized in heat-sealed bags in the same solution containing 50 μg/mL denatured, sheared salmon sperm DNA and 0.5 μg of digoxigen-dUTP labelled probes at 65° C. overnight. The membranes were washed twice for 15 min in 2× SSPE, 0.1% SDS at RT, twice for 15 min in 0.2× SSPE, 0.1% SDS at 65° C. and once for 5 min in 2× SSPE. Positively hybridizing clones were identified by reaction with an anti-digoxigenin/alkaline phosphatase antibody conjugate, 5-bromo-4-chloro-3-indoyl phosphate and 4-nitro blue tetrazolium chloride (Roche Diagnostics) following the manufacturer's protocol. Positively hybridizing clones were further purified by a second round of screening with the digoxigen-dUTP labelled probes.

Individual clones were isolated and the phage DNA purified as described in Sambrook et al. pp. 2.118-2.121 with the exception that the CsCl gradient step was replaced by extraction with 1 volume of phenol:choroform:isoamyl alcohol (25:24:1) and 1 volume of chloroform:isoamyl alcohol (24:1). The DNA was precipitated with 0.1 volumes of 3 M sodium acetate, pH 5.2 and 2.5 volumes cold 95% ethanol. The precipitated phage DNA was washed with 0.5 mL cold 70% ethanol, air-dried and resuspended in 50 μL 10 mM Tris, 1 mM EDTA pH 8.0. Restriction fragments containing the genes of interest were identified by restriction digests of the purified phage DNA and Southern blot hybridization (Sambrook, et al., pp. 9.38-9.44) using the same digoxigen-dUTP labelled probes used to screen the λDASH library. The membranes were hybridized and positively hybridizing fragments visualized by the same methods used for the plaque lifts. Once the desired restriction fragments from each λDASH clone were identified, the restriction digests were repeated, the fragments were resolved on a 0.8% agarose gel in TAE and the desired bands excised. The DNA was eluted from the gel slices using the Sephaglas B and Prep Kit (Pharmacia) following the manufacturer's protocol.

Clones carrying the xln2 gene were identified by colony lift hybridization of the λDASH library (Example 7) with a xln2 probe comprising bp 100-783 of the published xln2 sequence (Saarelainen et al., Mol. Gen. Genet. 241: 497-503, 1993). A 5.7 kb Kpn1 fragment containing the promoter (2.3 kb), coding region (0.8 kb) and terminator (2.6 kb) the xln2 gene was isolated by restriction digestion of phage DNA purified from a λDASH xln2 clone. This fragment was subcloned into the Kpn1 site of pUC119 to generate the plasmid pXYN2K-2.

10.4: Construction of a Vector Directing the Expression of Modified Family 6 Cellulase in *Trichoderma reesei*.

A 2.3 kb fragment containing the promoter and secretion signal of the xln2 gene (bp −2150 to +99 where +1 indicates the ATG start codon and +97-99 represent the first codon after the TrXyl11 secretion signal peptide) was amplified with Pwo polymerase from the genomic xln2 subclone pXYN2K-2 (Example 7) using an xln2-specific primer containing a NheI directly downstream of the Gln at codon 33 and the pUC reverse primer (Cat. No. 18432-013, Gibco/BRL) which anneals downstream of the Kpn1 site at the 5' end of the xln2 gene. This xlz2 PCR product was inserted as a blunt-ended fragment into the SmaI site of the pUC119 polylinker in such an orientation that the BamHI site of the polylinker is 3' to the NheI site; this generated the plasmid pUC/XynPSS(Nhe). The same xln2 PCR product was reisolated from pUC/XynPSS(Nhe) by digestion with EcoRI (which was amplified as part of the pUC119 polylinker from pXYN2K-2) and BamHI and inserted into the plasmid pBR322L (a derivative of pBR322 containing an Sph1-Not1-Sal1 adaptor between the original Sph1 and Sal1 sites at bp 565 and 650), also digested with EcoRI and BamHI, to generate the plasmid pBR322LXN. To facilitate high level expression of the modified xylanases, a 1.3 kb HindIII fragment comprising bp −1400 to −121 of the xln2 promoter in pBR322LXN was replaced with a 1.2 kb HindIII fragment comprising bp −1399 to −204 of the cbh1 promoter which was isolated by HindIII digestion of pCOR132; this generated the plasmid pBR322LC/XN. Finally, the EcoR1 site of pBR322LXC was then blunted with Klenow and Spe1 linkers (Cat. No. 1086, New England Biolabs) were added to generate pBR322SpXC.

A fragment containing the TrCel6A-S413P gene was isolated from the YEpFLAGΔKpn10-cbh2 vector (described in Example 6 above) by digestion with NheI and KpnI inserted into pCB219N-N digested with NheI and BamHI to generate pS413P/C2ter. To make pCB219N-N, a cbh2 terminator fragment was amplified from the pZUK600 (described in Example 7, above) template using a primer homologous to bp 2226-2242 of the published 3' untranslated region of the cbh2 gene (Chen et al., 1987) containing a short polylinker comprising XbaI-NheI-BamHI-SmaI-KpnI sites at the 5' end and the pUC forward primer (Cat. No. 1224, New England Biolabs) which anneals upstream of the EcoR1 site at the 3' end of cbh2 in pZUK600. This fragment was digested at the engineered XbaI and EcoRI sites and inserted into the corresponding sites of pUC119 to generate pCB219. An EcoR1-Not1 adaptor (Cat. No. 35310-010, Gibco/BRL) was inserted into the unique EcoR1 site of pCB219 to generate pCB219N. A fragment comprising the TrCel6A gene and the cbh2 terminator was isolated from pS413P/C2ter by digestion with NheI and NotI and inserted into pBR322SpXC digested with NheI and NotI to generate the expression cassette pc/xS413P-EC.

The selection cassette containing plasmid, pNCBgINSNB (r), was derived from a *N. crassa* pyr4 containing plasmid, pFB6 (Radford, A., Buston, F. P., Newbury, S. F. and Glazebrook, J. A. (1985) Regulation of pyrimidine metabolism in *Neurospora*. In Molecular Genetics of Filamentous Fungi (Timberlake, W. E., editor), Alan R. Liss (New York), pages 127-143). A 3.2 kb BglII fragment from pFB6 containing the *N. crassa* pyr4 gene (GenBank accession M13448) as well as its promoter, terminator and some 5' UTR sequences was cloned into the BamHI site of pUC119 modified to contain NotI, SmaI, NheI and BglII sites in the polylinker (between EcoRI and SacI) to generate pNCBgl-NSNB(r). An SpeI/NotI fragment comprising the TrCel6A-S413P gene operably linked to the cbh1 promoter, xln2 secretion signal peptide and cbh2 transcriptional terminator was isolated from the expression cassette vector pc/xS413P-EC and inserted into pNCBgl-NSNB(r) digested with NheI (SpeI and NheI having compatible 5' overhanging sequences) and NotI to generate $p^c/_x$-S413P-TV. This final construct was linearized by NotI prior to transformation of *Trichoderma reesei*.

Example 11

Transformation of the *Trichoderma reesei*

11.1 Isolation of pyr4 Auxotrophs

In order to use the *N. crassa* pyr4 gene as a selectable marker, a spontaneous pyr4 auxotroph was isolated as follows: $1 \times 10^6$ spores of *T. reesei* were plated onto minimal media containing 5 mM uridine and 0.15% (w/v) of the uridine analog 5-fluoroorotic acid (FOA) as previously described for the selection of pyr4 auxotrophs of *T. reesei* (Berges, T. and Barreau, C. 1991 *Curr Genet*. 19(5):359-65). The ability to grow on FOA-containing media will allow for selection of mutants disrupted in either the pyr2 gene encoding orotate phosphoribosyl transferase or the pyr4 gene encoding orotidine 5'-phosphate decarboxylase. Spontaneous FOA-resistant colonies were subjected to secondary selection of minimal media with and without uridine. Spores of FOA-resistant colonies that could not grow on minimal media were then transformed with pNCBgINSNB(r) (described in Example 11.4) and selected for growth on minimal media. Only those strains that were complemented by the *N. crassa* pyr4 gene in pNCBgINSNB(r) will grow on minimal media and are true pyr4 auxotrophs. Using these procedures, a stable pyr4 auxotroph of *T. reesei* was obtained.

11.2 Transformation of Protoplasts of *T. reesei* pyr4 Auxotrophs.

$5 \times 10^6$ spores of *T. reesei* were plated onto sterile cellophane on Potato Dextrose agar supplemented with 5 mM uridine and are incubated for 20 hours at 30° C. to facilitate spore germination and mycelial growth. Cellophane discs with mycelia were transferred to 10 mL of a protoplasting solution containing 7.5 g/L Driselase and 125 units of protease free β-glucanase (InterSpex Products Inc., Cat. Nos. 0465-1 and 0410-3, respectively) in 50 mM potassium phosphate buffer, pH 6.5 containing 0.6 M ammonium sulfate (Buffer P). The mycelial mat was digested for 5 hours with shaking at 60 rpm. Protoplasts were separated from undigested mycelia by filtration through sterile No. 30 MIRACLOTH™ and collected into a sterile 50 mL round-bottom centrifuge tube and recovered by centrifugation at 1000-1500×g for 10 min at room temperature. Protoplasts were washed with 5 mL of Buffer P and centrifuged again at 1000-1500×g for 10 min at room temperature. Protoplasts were resuspended in 1 mL of STC buffer (1.2 M sorbitol, 10 mM $CaCl_2$, 10 mM Tris-HCL, pH 7.5). For transformation, 0.1 mL of resuspended protoplasts were combined with 10 μg of vector DNA and 25 μL of PEG solution (25% PEG 4000, 50 mM $CaCl_2$, 10 mM Tris-HCl, pH 7.5). After incubation in an ice water bath for 30 min, 1 mL of PEG solution was added and the mixture incubated for 5 min at room temperature. Transformation mix was diluted with 2 mL of 1.2 M sorbitol in PEG solution and the entire mix was added to 25 mL of molten MMSS agar media (see below) cooled to about 47° C. and the protoplast suspension poured over MMSS agar. Plates were incubated at 30° C. until colony growth was visible. Transformants were transferred to individual plates containing MM agar and allowed to sporulate. Spores were collected and plated at high dilution on MM agar to isolate homokaryon transformants, which were then plated onto PDA to allow for growth and sufficient sporulation to inoculate the screening cultures as described in Example 13 below.

Minimal medium (MM) agar contains the following components:

| Reagent | Per L |
|---|---|
| $KH_2PO_4$ | 10 g |
| $(NH_4)_2SO_4$ | 6 g |
| $Na_3Citrate \cdot 2H_2O$ | 3 g |
| $FeSO_4 \cdot 7H_2O$ | 5 mg |
| $MnSO_4 \cdot H_2O$ | 1.6 mg |
| $ZnSO_4 \cdot 7H_2O$ | 1.4 mg |
| $CaCl_2 \cdot 2H_2O$ | 2 mg |
| Agar | 20 g |
| 20% Glucose f.s. | 50 mL |
| 1 M $MgSO_4 \cdot 7H_2O$ f.s. | 4 mL |
| | pH to 5.5 |

MMSS agar contains the same components as MM agar plus 1.2 M sorbitol, 1 g/L YNB (Yeast Nitrogen Base w/o Amino Acids from DIFCO Cat. No. 291940) and 0.12 g/L amino acids (-Ura DO Supplement from BD Biosciences Cat. No. 630416).

Example 12

Production of Modified Family 6 Cellulases in Liquid Cultures

Individual colonies of *Trichoderma* were transferred to PDA plates for the propagation of each culture. Sporulation was necessary for the uniform inoculation of the micro-cultures used in testing the ability of the culture to produce the modified TrCelA. variants with increased thermostability. The culture media is composed of the following:

| Component | g/L |
|---|---|
| $(NH_4)_2SO_4$ | 12.7 |
| $KH_2PO_4$ | 8.00 |
| $MgSO_4 \cdot 7H_2O$ | 4.00 |
| $CaCl_2 \cdot 2H_2O$ | 1.02 |
| Corn Steeped Liquor | 5.00 |
| $CaCO_3$ | 20.00 |
| Carbon source** | 30-35 |
| Trace elements* | 2 mL/L |

*Trace elements solution contains 5 g/L $FeSO_4.7H_2O$; 1.6 g/L $MnSO_4.H_2O$; 1.4 g/L $ZnSO_4.7H_2O$.
** glucose, Solka floc, lactose, cellobiose, sophorose, corn syrup, or Avicel. The carbon source can be sterilized separately as an aqueous solution at pH 2 to 7 and added to the remaining media initially or through the course of the fermentation.

Individual transformants were grown in the above media in 1 mL cultures in 24-well micro-plates. The initial pH was 5.5 and the media sterilized by steam autoclave for 30 minutes at 121° C. prior to inoculation. For both native and transformed cells, spores were isolated from the PDA plates, suspended in water and $10^4$-$10^5$ spores per mL were used to inoculate each culture. The cultures were shaken at 500 rpm at a temperature of 30° C. for a period of 6 days. The biomass was separated from the filtrate containing the secreted protein by centrifugation at 12,000 rpm. The protein concentration was determined using the Bio-Rad Protein Assay (Cat. No. 500-0001). Expression of TrCelA-S413P was determined as described in Example 14.

Example 13

Characterization of *T. reesei* Culture Filtrates Comprising Modified Family 6 Cellulases The expression of TrCel6A-S413P in culture filtrates of *T. reesei* transformants was determined by Western blot hybridization of SDS-PAGE gels. Specifically, equal amounts of total secreted protein in 10-20 µL of culture filtrate from the TrCel6A-S413P transformants, the parent strain P107B and a strain expressing the native, unmodified TrCel6A (strain BTR213) were added to an equal volume of 2× Laemmli buffer (0.4 g SDS/2 mL glycerol/1 mL 1M Tris-HCl, pH 6.8/0.3085 g DTT/2 mL 0.5% bromophenol blue/0.25 mL β-mercaptoethanol/10 mL total volume). 10 uL of each prepared sample was resolved on a 10% SDS polyacrylamide gel using 24 mM Tris, 192 mM glycine pH 6.8, 10 mM SDS as running buffer. The separated proteins were transferred electrophoretically from the acrylamide gel to a PVDF membrane, prewetted with methanol, in 25 mM Tris/192 mM glycine buffer containing 20% methanol. The membrane was subsequently washed in 30 mL of BLOTTO buffer (5% skim milk powder in 50 mM Tris-HCl, pH 8.0). The membrane was probed with 30 mL of a 1:20,000 dilution of polyclonal antibodies specific to TrCel6A in BLOTTO overnight at room temperature, washed twice more for 10 min with an equal volume of BLOTTO at room temperature, then probed for 1 hour with a 1:3000 dilution of goat anti-rabbit/alkaline phosphatase conjugate in BLOTTO at room temperature. Finally, the membrane was washed twice for 15 min each at room temperature with an excess of 50 mM Tris-HCl, pH 8.0. Hybridizing complexes containing TrCel6A were visualized by treatment of the membrane with 10 mL of a 100 mM NaCl/100 mM Tris-HCl, pH 9.5 buffer containing 45 µl of 4-nitro blue tetrazolium chloride (Roche Diagnostics) and 35 µL of 5-bromo-4-chloro-3-indoyl phosphate (Roche Diagnostics) at room temperature until bands were clearly visible. Positively hybridizing bands of ~60 kDa were observed in the culture filtrates from most transformants, the positive control strain BTR213, but not from the culture filtrate from strain P107B. Transformant P474B expresses and secretes approximately the same level of TrCel6A-S413P as the amount of unmodified TrCel6A expressed and secreted by the control strain BTR213.

The stability of the *Trichoderma* cellulases containing TrCel6A or TrCel6A-S413P was assessed incubation of the cellulases in 50 mM citrate buffer, pH 4.8 at 50° C. for up to 96 hours and then measuring the residual activity of the cellulase by nephelometry (Enari, T. M. and Niku-Paavola M. L. 1988. Meth. Enzym. 160: 117-126).

While the rate of cellulose hydrolysis by the untreated TrCel6A and TrCel6A-S413P cellulases was identical, after incubation for up to 96 hours in the absence of substrate, the TrCel6A-S413P cellulase maintained much higher activity than the TrCel6A cellulase (FIG. 8). Thus, improvements in the thermostability of TrCel6A also improved the thermostability of a whole *Trichoderma* cellulase system comprising the modified Family 6 cellulase and other components.

The present invention has been described with regard to preferred embodiments. However, it will be obvious to persons skilled in the art that a number of variations and modifications can be made without departing from the scope of the invention as described herein.

All references and citations are herein incorporated by reference.

REFERENCES

Ai, Y. C. and Wilson, D. B. 2002. Enzyme Microb. Technol. 30:804-808.
Atomi, H. 2005. Curr. Opin. Chem. Biol. 9:166-173.
Berges, T. and Barreau, C. 1991 Curr Genet. 19(5):359-65
Bhat, M. K. 2000. Biotechnol. Adv. 18:355-383.
Butler, T. and Alcalde, M. 2003. In Methods in Molecular Biology, vol. 231: (F. H. Arnold and G. Georgiou, editors), Humana Press Inc. Totowa (New Jersey), pages 17-22.
Chica, R. A., et al. 2005. Curr. Opin. Biotechnol. 16:378-384.
Claeyssens, M. and Henrissat, B. 1992. Protein Science 1: 1293-1297).
Claeyssens, M., et al. 1997. Eds.; The Royal Society of Chemistry, Cambridge.
Davies, G. J., et al. 2000. Biochem. J. 348:201-207.
Eijsink, V. G., et al. 2004. J. Biotechnol. 113:105-20.
Eijsink V G, et al. 2005. Biomol. Eng. 22:21-30.
Foreman, P. K., et al. 2003. J. Biol. Chem. 278:31988-31997.

Gietz, R. D. and Woods, R. A. 2002. Meth. Enzym. 350: 87-96.
Gray, K. A., et al. 2006. Curr. Opin. Chem. Biol. 10:141-146.
Hoffman, C. S., and Winston, F. 1987. Gene 57: 267-272.
Hughes, S. R., et al. 2006. Proteome Sci. 4:10-23.
Lehtio, J., et al. 2003. Proc Natl Acad Sci USA. 100:484-489.
Li, W. F., et al. 2005 Biotechnol. Adv. 23:271-281.
Lin, Y. and Tanaka, S. 2006. Appl. Microbiol. Biotechnol. 69:627-642.
Mathrani, I. and Ahring, B. K. 1992 Appl. Microbiol. Biotechnol. 38:23-27.
Meinke, A., et al. 1995. J. Biol. Chem. 270:4383-4386.
Radford, A., et al. 1985. In Molecular Genetics of Filamentous Fungi (Timberlake, W. E., editor), Alan R. Liss (New York), pages 127-143
Rouvinen, J., et al. 1990. Science 249:380-386. Erratum in: Science 1990 249:1359.
Saarelainen, R., et al. 1993. Mol. Gen. Genet. 241: 497-503.
Sadeghi, M., et al. 2006. Biophys. Chem. 119:256-270.
Sambrook, et al. 1989. Molecular Cloning: A Laboratory Manual, Second Edition", Cold Spring Harbor Press
Srisodsuk, M., et al. 1993. J. Biol. Chem. 268:20756-20761.
Spezio, M., et al. 1993. Biochemistry. 32:9906-9916.
Tomme, P., et al. 1988. Eur. J. Biochem 170:575-581.
Varrot, A., et al. 2005. J. Biol. Chem. 280:20181-20184.
Varrot, A., et al. 1999. Biochem. J. 337:297-304.
Vieille, C. and Zeikus, G. J. 2001. Microbiol. Mol. Biol. Rev. 65:1-43.
Viera and Messing 1987. Methods Enzymol. 153:3
von Ossowski, I., et al. 2003. J Mol. Biol. 333:817-829.
Wohlfahrt, G., et al. 2003. Biochemistry. 42:10095-10103.
Zhang S, et al. 2000. Eur. J. Biochem. 267:3101-15.

The embodiments of the invention in which an exclusive property or privilege is claimed are defined as follows:

1. An isolated Family 6 cellulase comprising one or more mutations, said one or more mutations consisting essentially of a non-native proline residue at position 413 and optionally with:
   (i) a substituted non-native amino acid at position 231 consisting of Ser or Thr;
   (ii) a substituted non-native amino acid at position 305 consisting of Ser or Thr;
   (iii) a substituted amino acid at position 410 consisting of Gln or Asn;
   (iv) a substituted Glu amino acid at position 82; or
   (v) a combination thereof,
   said positions being determined from sequence alignment of said isolated Family 6 cellulase with a *Trichoderma reesei* Ce16A amino acid sequence as defined in SEQ ID NO:1, wherein said isolated cellulase exhibits enhanced thermostability, alkalophilicity, thermophilicity or a combination thereof relative to a corresponding parent Family 6 cellulase, and wherein the isolated Family 6 cellulase is derived from a fungal Family 6 cellulase.

2. The isolated Family 6 cellulase of claim 1, comprising the substituted non-native amino acid at position 231 consisting of Ser or Thr.

3. The isolated Family 6 cellulase of claim 1, comprising the substituted non-native amino acid at position 305 consisting of Ser or Thr.

4. The isolated Family 6 cellulase of claim 1, comprising the substituted non-native amino acid at position 410 consisting of Gln or Asn.

5. The isolated Family 6 cellulase of claim 1, comprising the substituted non-native amino acids at positions 231, 410 and 305, wherein the non-native amino acids at positions 231 and 305 are Ser residues and wherein the substituted non-native amino acid at position 410 is Gln.

6. The isolated Family 6 cellulase of claim 1, wherein said filamentous fungus is *Trichoderma reesei*.

7. The isolated Family 6 cellulase of claim 1, wherein said isolated Family 6 cellulase has an increase in thermostability, as evidenced by an increase in its $T_{50}$ of at least 5° C., over that of the parent Family 6 cellulase.

8. The isolated Family 6 cellulase of claim 1, wherein said isolated Family 6 cellulase has an increase in thermostability, as evidenced by an increase in its $T_{50}$ of at least 9° C., over that of the parent Family 6 cellulase.

9. The isolated Family 6 cellulase of claim 1, wherein said isolated Family 6 cellulase has an increase in thermophilicity, as evidenced by an increase in its $T_{opt}$ of at least 1.5° C., over that of the parent Family 6 cellulase.

10. The isolated Family 6 cellulase of claim 1, wherein said isolated Family 6 cellulase has an increase in thermophilicity, as evidenced by an increase in its $T_{opt}$ of at least 2.5° C., over that of the parent Family 6 cellulase.

11. The isolated Family 6 cellulase of claim 1, wherein said isolated Family 6 cellulase has an increase in alkalophilicity, as evidenced by an increase in its $pH_{opt}$ of at least 0.5 units, over that of the parent Family 6 cellulase.

12. An isolated Family 6 cellulase selected from the group consisting of:

```
                                                    (SEQ ID NO: 12)
    TrCe16A-S413P;

(SEQ ID NO: 13)
    TrCe16A-G82E-G231S-N305S-R410Q-S413P;

(SEQ ID NO: 14)
    TrCe16A-G231S-S413P;

(SEQ ID NO: 15)
    TrCe16A-N305S-S413P;

(SEQ ID NO: 16)
    TrCe16A-R410Q-S413P;

(SEQ ID NO: 17)
    TrCe16A-G231S-N305S-S413P;

(SEQ ID NO: 18)
    TrCe16A-G231S-R410Q-S413P;

(SEQ ID NO: 19)
    TrCe16A-N305S-R410Q-S413P;

(SEQ ID NO: 20)
    TrCe16A-G231S-N305S-R410Q-S413P;

(SEQ ID NO: 21)
    HiCe16A-Y420P;
    and (SEQ ID NO: 22)
    PcCe16A-S407P.
```

13. The isolated Family 6 cellulase of claim 1, wherein the isolated Family 6 cellulase has 64-100% sequence identity to amino acids 82-447 of the *Trichoderma reesei* Ce16A amino acid sequence as defined in SEQ ID NO:1.

14. An isolated Family 6 cellulase comprising one or more mutations, including a non-native proline residue at position 413, said position determined from sequence alignment of said modified cellulase with a *Trichoderma reesei* Cel6A amino acid sequence as defined in SEQ ID NO:1, wherein said isolated cellulase is derived from a fungal Family 6 cellulase and exhibits enhanced thermostability, alkalophilicity, thermophilicity or a combination thereof relative to a corresponding parental Family 6 cellulase, and wherein said isolated Family 6 cellulase has a catalytic domain comprising
an active site comprising a central β-barrel comprising seven parallel β-strands connected by five α-helices,
a C-terminal loop that forms a tunnel with an N-terminal loop that encloses the active site, and
said one or more mutations that enhance thermostability, alkophilicity or thermophilicity.

15. An isolated Family 6 cellulase comprising one or more mutations, including a non-native proline residue at position 413, said position determined from sequence alignment of said modified cellulase with a *Trichoderma reesei* Cel6A amino acid sequence as defined in SEQ ID NO:1, wherein said isolated cellulase is derived from a fungal Family 6 cellulase and exhibits enhanced thermostability, alkalophilicity, thermophilicity or a combination thereof relative to a corresponding parental Family 6 cellulase, and wherein said isolated Family 6 cellulase has at least 98% identity to amino acids 82-447 of the *Trichoderma reesei* Cel6A amino acid sequence as defined by SEQ ID NO: 1.

16. A method of treating a cellulosic substrate, comprising contacting said cellulosic substrate with the isolated Family 6 cellulase of any one of claims 1-5, 6, 7-12, 13, 14 or 15.

17. A process for producing an isolated Family 6 cellulase of any one of claims 1-5, 6, 7-12, 13, 14 or 15, the process comprising (i) transforming fungal host cells with a genetic construct comprising a DNA sequence encoding said isolated Family 6 cellulase, which DNA sequence is operably linked to DNA sequences regulating its expression and secretion from a host microbe, so as to produce recombinant fungal strains; (ii) selecting the recombinant fungal strains expressing the isolated Family 6 cellulase; and (iii) culturing selected recombinant strains in submerged liquid fermentations under conditions that induce the expression of the isolated Family 6 cellulase.

* * * * *

UNITED STATES PATENT AND TRADEMARK OFFICE
CERTIFICATE OF CORRECTION

PATENT NO. : 7,785,854 B2
APPLICATION NO. : 11/846663
DATED : August 31, 2010
INVENTOR(S) : Patrick St-Pierre et al.

It is certified that error appears in the above-identified patent and that said Letters Patent is hereby corrected as shown below:

COLUMN 1

Line 38, "hydrolyse" should read --hydrolyze--; and
    Line 61, "β-1,4-glucosidase," should read --β-1,4-glucosidases,--.

COLUMN 2

Line 5, "three dimensional" should read --three-dimensional--.

COLUMN 3

Line 22, "based" should read --based on--; and
    Line 67, "alkophilicity." should read --alkalophilicity.--.

COLUMN 6

Line 35, "sequences." should read --sequence.--; and
    Line 60, "pC/X—S413P-TV" should read --pC/X-S413P-TV--.

COLUMN 7

Line 6, "G231 S-N.305S-S413P," should read --G231S-N305S-S413P,--;
    Line 15, "sugars a" should read --sugars from a--; and
    Line 21, "TrCel6A-G2311S-N305S-R410Q-S413P" should read
      --TrCel6A-G231S-N305S-R410Q-S413P--.

COLUMN 9

Line 36, "here in" should read --herein--.

Signed and Sealed this

Thirtieth Day of November, 2010

David J. Kappos
*Director of the United States Patent and Trademark Office*

COLUMN 10

Line 12, "of" should be deleted;
    Line 28, "Tso" should read --$T_{50}$--; and
    Line 44, "$T_{50}$ so" should read --$T_{50}$--.

COLUMN 12

Line 63, "baggase," should read --bagasse,--.

COLUMN 13

Line 44, "then" should read --than--;
    Line 52, "shown" should read --showed--; and
    Line 56, "then" should read --than--.

COLUMN 15

Line 18, "($str^I$)" should read --($str^r$)--; and
    Line 66, "(C2STU 5" should read --(C2STU5--.

COLUMN 18

Line 14, "heat treated" should read --heat-treated--;
    Line 35, "YEpPLAG-1" should read --YEpFLAG-1--;
    Line 36, "operabling" should read --operably--; and "αmating" should read --α mating--; and
    Line 63, "fragments" should read --fragment--.

COLUMN 19

Line 14, "YEpFLAGΔKpn10-N305S" should read --YEpFLAGΔKpn10-N305S,--.

COLUMN 20

Line 6, "5'N305SGBH2" should read --5'N305SCBH2--;
    Line 24, "spreaded" should read --spread--; and
    Line 45, "clone" should read --cloned--.

COLUMN 21

Line 10, "Generation" should read --Generation of--;
    Line 12, "spreaded" should read --spread--;
    Line 42, "Clone" should read --cloned--; and "pGEMO-T Easy" should read --pGEM®-T Easy--; and
    Line 43, "TA-Cloning" should read --TA-cloning--.

COLUMN 22

Line 32, "600 m" should read --600 nm--; and
Line 60, "thermophilicity" should read --Thermophilicity--.

COLUMN 23

Line 29, "shown" should read --showed--;
Line 33, "then" should read --than--; and
Line 50, "where" should read --were--.

COLUMN 25

Line 1, "disclosed" should read --disclosed in--;
Line 7, "then" should read --than--;
Line 8, "Hicel6A-Y420P" should read --HiCel6A-Y420P--; and
Line 9, "TSO" should read --$T_{50}$--.

COLUMN 28

Line 38, "(2.6kb) the" should read --(2.6 kb) of the--.

COLUMN 31

Line 29, "5g/L $FeSO_4.7H_2O$; 6g/L $MnSO_4.H_2O$;" should read --5g/L $FeSO_4.7H_2O$; 6g/L $MnSO_4.H_2O$;--; and
Line 30, "g/L $ZnSO_4.7H_2O$." should read --g/L $ZnSO_4.7H_2O$.--.

COLUMN 97

Line 29, "substituted amino acid" should read --substituted non-native amino acid--.

COLUMN 100

Line 7, "claims 1-5, 6, 7-12, 13, 14 or 15." should read --claims 1-15.--; and
Line 9, "claims 1-5, 6, 7-12, 13, 14 or 15," should read --claims 1-15,--.